United States Patent
Parrag et al.

(10) Patent No.: US 11,612,567 B2
(45) Date of Patent: *Mar. 28, 2023

(54) OCULAR INSERTS COMPRISING A COVALENTLY LINKED STEROID DIMER

(71) Applicant: Ripple Therapeutics Corporation, Toronto (CA)

(72) Inventors: Ian Charles Parrag, Mississauga (CA); Matthew Alexander John Statham, Milton (CA); Kyle Battiston, Toronto (CA); Dimitra Louka, Toronto (CA); Wendy Alison Naimark, Tornto (CA); Hans Christian Fischer, Toronto (CA); Leonard Pinchuk, Miami, FL (US)

(73) Assignee: RIPPLE THERAPEUTICS CORPORATION, Toronto (CA)

( * ) Notice: Subject to any disclaimer, the term of this patent is extended or adjusted under 35 U.S.C. 154(b) by 118 days.

This patent is subject to a terminal disclaimer.

(21) Appl. No.: 16/966,453

(22) PCT Filed: Feb. 1, 2019

(86) PCT No.: PCT/CA2019/050133
§ 371 (c)(1),
(2) Date: Jul. 30, 2020

(87) PCT Pub. No.: WO2019/148291
PCT Pub. Date: Aug. 8, 2019

(65) Prior Publication Data
US 2021/0030667 A1    Feb. 4, 2021

Related U.S. Application Data

(60) Provisional application No. 62/758,234, filed on Nov. 9, 2018, provisional application No. 62/627,608, filed on Feb. 7, 2018, provisional application No. 62/625,460, filed on Feb. 2, 2018.

(51) Int. Cl.

| | |
|---|---|
| *A61K 9/16* | (2006.01) |
| *A61K 9/70* | (2006.01) |
| *A61K 9/00* | (2006.01) |
| *A61K 9/51* | (2006.01) |
| *A61K 31/573* | (2006.01) |
| *A61K 9/50* | (2006.01) |
| *A61K 47/55* | (2017.01) |
| *A61K 47/69* | (2017.01) |
| *A61P 29/00* | (2006.01) |
| *A61P 27/02* | (2006.01) |
| *A61K 47/54* | (2017.01) |

(52) U.S. Cl.
CPC ............ *A61K 9/167* (2013.01); *A61K 9/0048* (2013.01); *A61K 9/0051* (2013.01); *A61K 9/0092* (2013.01); *A61K 9/1682* (2013.01); *A61K 9/50* (2013.01); *A61K 9/5089* (2013.01); *A61K 9/51* (2013.01); *A61K 9/5192* (2013.01); *A61K 9/7007* (2013.01); *A61K 31/573* (2013.01); *A61K 47/54* (2017.08); *A61K 47/55* (2017.08); *A61K 47/6921* (2017.08); *A61K 47/6953* (2017.08); *A61P 27/02* (2018.01); *A61P 29/00* (2018.01)

(58) Field of Classification Search
CPC .... A61K 9/167; A61K 9/0048; A61K 9/0051; A61K 9/0092; A61K 9/1682; A61K 9/50; A61K 9/5089; A61K 9/51
See application file for complete search history.

(56) References Cited

U.S. PATENT DOCUMENTS

| | | |
|---|---|---|
| 3,591,612 A | 7/1971 | Allais et al. |
| 3,663,579 A | 5/1972 | Stache et al. |
| 4,024,871 A | 5/1977 | Stephenson |
| 4,532,316 A | 7/1985 | Henn |
| 4,833,215 A | 5/1989 | Jedlinski et al. |
| 4,916,193 A | 4/1990 | Tang et al. |
| 5,013,841 A | 5/1991 | Matsumoto et al. |
| 5,217,493 A | 6/1993 | Raad et al. |
| 5,250,524 A | 10/1993 | Kramer et al. |
| 5,321,099 A | 6/1994 | Goldwasser et al. |
| 5,387,598 A | 2/1995 | Rossignol |
| 5,512,558 A | 4/1996 | Enhsen et al. |
| 5,578,621 A | 11/1996 | Rossignol |
| 5,798,115 A | 8/1998 | Santerre et al. |
| 5,856,348 A | 1/1999 | Rossignol |
| 5,859,038 A | 1/1999 | Rossignol |
| 5,886,013 A | 3/1999 | Rossignol |
| 5,965,590 A | 10/1999 | Rossignol |
| 5,968,961 A | 10/1999 | Rossignol |

(Continued)

FOREIGN PATENT DOCUMENTS

| | | |
|---|---|---|
| CA | 2461099 A1 | 4/2003 |
| CA | 2467321 A1 | 11/2005 |

(Continued)

OTHER PUBLICATIONS

Saraiya DEX Ocular Inflamm. Expert Opinion Pharmaco. p. 1131, Apr. 2011.*
Bach et al., Retention of Antibacterial Activity and Bacterial Colonization of Antiseptic-Bonded Central Venous Catheters. J. Antimicrob. Chemother. 37:315-322 (1996).
Berge et al. Pharmaceutical Salts. Journal of Pharmaceutical Sciences 66(1):1-19 (Jan. 1977).

(Continued)

*Primary Examiner* — Matthew P Coughlin
*Assistant Examiner* — Thurman Wheeler
(74) *Attorney, Agent, or Firm* — Wilson Sonsini Goodrich & Rosati

(57) ABSTRACT

The disclosure relates to compounds and compositions for sustained release of ocular therapeutics.

15 Claims, 32 Drawing Sheets

(56) References Cited

U.S. PATENT DOCUMENTS

| | | |
|---|---|---|
| 6,020,353 A | 2/2000 | Rossignol |
| 6,051,576 A | 4/2000 | Ashton et al. |
| 6,096,525 A | 8/2000 | Patnaik |
| 6,117,894 A | 9/2000 | Rossignol |
| 6,127,507 A | 10/2000 | Santerre |
| 6,299,604 B1 | 10/2001 | Ragheb et al. |
| 6,344,035 B1 | 2/2002 | Chudzik et al. |
| 6,429,300 B1 | 8/2002 | Kurz et al. |
| 6,602,915 B2 | 8/2003 | Uhrich |
| 6,689,350 B2 | 2/2004 | Uhrich |
| 6,703,037 B1 | 3/2004 | Hubbell et al. |
| 6,770,725 B2 | 8/2004 | Santerre |
| 8,349,309 B2 | 1/2013 | Santerre et al. |
| 8,968,626 B2 | 3/2015 | Pham et al. |
| 9,056,048 B2 | 6/2015 | Diamond et al. |
| 10,588,862 B2 | 3/2020 | Parrag et al. |
| 10,632,075 B2 | 4/2020 | Parrag et al. |
| 2003/0035787 A1 | 2/2003 | Uhrich |
| 2003/0039689 A1 | 2/2003 | Chen et al. |
| 2003/0118528 A1 | 6/2003 | Walters et al. |
| 2003/0158598 A1 | 8/2003 | Ashton et al. |
| 2003/0203030 A1 | 10/2003 | Ashton et al. |
| 2004/0087664 A1 | 5/2004 | Marcus et al. |
| 2004/0180036 A1 | 9/2004 | Ashton et al. |
| 2005/0008695 A1 | 1/2005 | Ashton et al. |
| 2005/0031577 A1 | 2/2005 | Uhrich |
| 2005/0070470 A1 | 3/2005 | Coy et al. |
| 2005/0159609 A1 | 7/2005 | King et al. |
| 2005/0164994 A1 | 7/2005 | Ashton et al. |
| 2005/0220839 A1 | 10/2005 | DeWitt et al. |
| 2005/0255079 A1 | 11/2005 | Santerre et al. |
| 2007/0031472 A1 | 2/2007 | Huang et al. |
| 2010/0062974 A1 | 3/2010 | Laronde et al. |
| 2013/0289223 A1 | 10/2013 | Santerre et al. |
| 2014/0256696 A1 | 9/2014 | Sinha et al. |
| 2016/0038651 A1 | 2/2016 | Santerre et al. |
| 2019/0247311 A1 | 8/2019 | Parrag et al. |
| 2020/0113833 A1 | 4/2020 | Parrag et al. |
| 2020/0113834 A1 | 4/2020 | Parrag et al. |
| 2021/0113457 A1 | 4/2021 | Parrag et al. |
| 2021/0205222 A1 | 7/2021 | Parrag et al. |
| 2022/0089635 A1 | 3/2022 | Parrag et al. |
| 2022/0288277 A1 | 9/2022 | Parrag et al. |
| 2022/0289787 A1 | 9/2022 | Parrag et al. |

FOREIGN PATENT DOCUMENTS

| | | | |
|---|---|---|---|
| CA | 2571320 A1 | 11/2005 | |
| CA | 2906238 A1 | 9/2014 | |
| CH | 592687 A5 | 11/1977 | |
| CN | 1968715 B | 12/2010 | |
| CN | 105377319 A | 3/2016 | |
| FR | 2007815 A1 | 1/1970 | |
| JP | H07501470 A | 2/1995 | |
| JP | H0924093 A | 1/1997 | |
| JP | 2000501318 A | 2/2000 | |
| JP | 2007537168 A | 12/2007 | |
| WO | WO-9511907 A1 | 5/1995 | |
| WO | WO-9520567 A1 * | 8/1995 | ............ A61K 47/55 |
| WO | WO-9528393 A1 | 10/1995 | |
| WO | WO-9729778 A2 | 8/1997 | |
| WO | WO-9807458 A1 | 2/1998 | |
| WO | WO-9850035 A1 | 11/1998 | |
| WO | WO-9906430 A1 | 2/1999 | |
| WO | WO-9912990 A1 | 3/1999 | |
| WO | WO-0209768 A2 | 2/2002 | |
| WO | WO-03028527 A2 | 4/2003 | |
| WO | WO-03040104 A1 | 5/2003 | |
| WO | WO-03043657 A1 | 5/2003 | |
| WO | WO-2004016214 A2 | 2/2004 | |
| WO | WO-2005110485 A1 | 11/2005 | |
| WO | WO-2010062562 A1 | 6/2010 | |
| WO | WO-2011120044 A1 | 9/2011 | |
| WO | WO-2012109445 A1 | 8/2012 | |
| WO | WO-2013106528 A1 | 7/2013 | |
| WO | WO-2014139033 A1 | 9/2014 | |
| WO | WO-2015168014 A1 | 11/2015 | |
| WO | WO-2017083794 A1 | 5/2017 | |
| WO | WO-2019148291 A1 | 8/2019 | |
| WO | WO-2019148293 A1 | 8/2019 | |
| WO | WO-2019148294 A1 | 8/2019 | |
| WO | WO-2020154815 A1 | 8/2020 | |
| WO | WO-2021005417 A1 | 1/2021 | |
| WO | WO-2021014217 A1 | 1/2021 | |

OTHER PUBLICATIONS

Blondeau. Fluoroquinolones: mechanism of action, classification, and development of resistance. Surv Ophthalmol. 49 Suppl 2:S73-8 (2004).
Budavari. The Merck Index—Fourteenth Edition Merck Research Laboratories. Whitehouse Station, NJ, pp. 1306-1307 (2006).
Burger. Isosterism and Bioisosterism in Drug Design, in Progress in Drug Research 287-328 (Ernst Jucker, ed., Birkhauser Verlag) (1991).
Cheng et al., Intravitreal sustained-release dexamethasone device in the treatment of experimental uveitis. Invest Ophthalmol Vis Sci. 36(2):442-53 (1995).
Chirife et al., In vitro antibacterial activity of concentrated polyethylene glycol 400 solutions. Antimicrob Agents Chemother. 24(3):409-12 (1983).
Coessens et al., Synthesis and In Vitro Stability of Macromolecular Prodrugs of Norfloxacin. J. Cont. Release 47:283-291 (1997).
Ditizio et al., A Liposomal Hydrogel for the Prevention of Bacterial Adhesion to Catheters. Biomaterials 19:1877-1884 (1998).
Gaudana et al. Ocular drug delivery. AAPS J. 12(3):348-360 (2010).
Ghosh. Monomers and Polymers from Nalidixic Acid—Synthesis, Characterization, and Hydrolysis Study, in Progress in Biomedical Polymers, Ed. Gebekin et al., Plenum Press, New York, pp. 335-345 (1990).
Ghosh. Studies Directed Towards Polymeric Quinloone Antibiotics— Synthesis of Potential Monomers From Nalidixic Acid. Polymeric Mat. Sci. Engin. 59:790-793 (1988).
Gower et al. Drug discovery in ophthalmology: past success, present challenges, and future opportunities. BMC Ophthalmology 16:11 (Jan. 16, 2016).
Kanra et al., The short-term efficacy and safety of dexamethasone implant in a difficult-to-treat patient population with persistent diabetic macular edema. Ret Vit. 26(3):221-7 (2017) (English Abstract).
Kerns et al., Piperazinyl-linked fluoroquinolone dimers possessing potent antibacterial activity against drug-resistant strains of *Staphylococcus aureus*. Bioorg Med Chem Lett. 13(10):1745-9 (2003).
Li et al., Dimeric and Oligomeric Steroids. Chem Rev. 97(1):283-304 (1997).
Michael et al. Enhanced RNA binding of dimerized aminoglycosides. Bioorg Med Chem 7:1361-1371 (1999).
Modak et al., A New Method for the Direct Incorporation of Antibiotic in Prosthetic Vascular Grafts. Surg. Gynecol. Obstet. 164:143-147 (1987).
Nathan et al., Copolymers of Lysine and Polyethylene Glycol: A New Family of Functionalized Drug Carriers, Bioconjug. Chem. 4:54-62 (1993).
Nishida et al., Studies on synthesis of antibacterial agent (NM441). I. Kinetics and mechanism of the reaction of 4-(bromomethyl)-5-methyl-1,3-dioxo1-2-one with 1-substituted piperazine (NM394). Bull Chem Soc Jpn. 67:1419-26 (1994).
Nosova et al., Synthesis of new fluorinated derivatives of quinolinecarboxylic acids. Chem Heterocycl Compd 38(8):922-8 (2002).
Odian (Principles of Polymerization, 4th ed.(2004).
Paryze et al., A new approach to steroid dimers and macrocycles by the reaction of 3-chlorocarbonyl derivatives of bile acids with 0,0-, N,N-, and S,S-dinucleophiles. Tetrahedron Lett. 53(46):6212-5 (2012).
Patani et al. Bioisosterism: A Rational Approach in Drug Design. Chem. Rev. 96:3147-3176 (1996).
PCT/CA2014/050284 International Search Report and Written Opinion dated Jun. 2, 2014.

(56) References Cited

OTHER PUBLICATIONS

PCT/CA2019/050133 International Search Report and Written Opinion dated Apr. 29, 2019.
PCT/CA2019/050135 International Search Report and Written Opinion dated Apr. 29, 2019.
PCT/CA2019/050136 International Search Report and Written Opinion dated Apr. 29, 2019.
PCT/CA2020/050117 International Search Report and Written Opinion dated Apr. 15, 2020.
Ren et al., Macromolecular prodrug of dexamethasone prevents particle-induced peri-implant osteolysis with reduced systemic side effects. J Control Release. 175:1-9 (2014) (24 pages).
Roseeuw et al., Polymeric Prodrugs of Antibiotics with Improved Efficiency. J. Mater. Sci. Mater. Med. 10:743-746 (1999).
Step-growth Polymerization. http://en.wikipedia.org/wiki/Step-growth_polymerization, retrieved on Jan. 12, 2012 (11 pages).
U.S. Appl. No. 16/396,400 Office Action dated Jun. 24, 2019.
U.S. Appl. No. 16/396,400 Office Action dated Oct. 15, 2019.
U.S. Appl. No. 16/396,400 Response to Non-Final Office Action dated Sep. 24, 2019.
U.S. Appl. No. 16/698,372 Office Action dated Jan. 21, 2020.
U.S. Appl. No. 16/698,372 Office Action dated May 26, 2020.
U.S. Appl. No. 16/699,305 Office Action dated Feb. 3, 2020.
U.S. Appl. No. 16/699,305 Office Action dated May 26, 2020.
Woo et al., Biological characterization of a novel biodegradable antimicrobial polymer synthesized with fluoroquinolones, J. Biomat. Res., 59(1):35-45 (2002).
Woo et al., Synthesis and characterization of a novel biodegradable antimicrobial polymer, Biomaterials, 21:1235-1246 (2000).
Xue et al., New dimeric cholesteryl-based A(LS)2 gelators with remarkable gelling abilities: organogel formation at room temperature. J Colloid Interface Sci. 361(2):556-64 (2011).
Yang et al. Utilization of quinolone drugs as monomers: characterization of the synthesis reaction products for poly(norfloxacin diisocyanatododecane polycaprolactone). Biomacromolecules 2(1):134-41 (2001).
Howard-Sparks et al. A Novel Chemical Delivery System Comprising an Ocular Sustained Re-lease Formulation of a 3a-17a-21-trihydroxy-5B-pregnan-20-one-BIS-5-Fluorouracil Coding. Drug Dev Ind Pharm 33:677-682 (2007).
Morimoto et al. New dimeric morphine from opium poppy (*Papaver somuniferum*) and its physiological function. J Nat Prod 66(7):987-989 (2003).
PCT/IB2020/000656 International Search Report and Written Opinion dated Nov. 16, 2020.
PCT/IB2020/000663 International Search Report and Written Opinion dated Dec. 1, 2020.
Peng et al. Pharmacological properties of bivalent ligands containing butorphan linked to nalbuphine, naltrexone, and naloxone at mu, delta, and kappa opioid receptors. J Med Chem 50(9):2254-2258 (2007).
Chanphai et al. Conjugation of steroids with PAMAM nanoparticles. Colloids and Surfaces B: Biointerfaces 136:1035-1041 (2015).
Janout et al., Bioconjugate-Based Molecular Umbrellas. Bioconjugate Chemistry, 20(2):183-192 (E-Pub Nov. 20, 2008).
Janout et al. Molecular umbrella-amphotercin B conjugates. Bioconjugate Chemistry 25:1408-1411 (2014).
Nahar et al. A review on steroid dimers: 2011-2019. Steroids 164:108736 (2020).
Nahar et al. A review on synthetic and natural steroid dimers: 1997-2006. Current Medicinal Chemistry 14:1349-1370 (2007).
PCT/IB2020/000620 International Search Report and Written Opinion dated Oct. 30, 2020.
Sarker et al. Chapter 6: Applications of Steroid Dimers, in Steroid Dimer: Chemistry and Applications in Drug Design and Delivery, John Wiley & Sons Ltd. pp. 379-407 (2012).
Svobodova et al. Recent advances in steroidal supramolecular gels. RSC Advances 2:4985-5007 (2012).
Sinha. New findings on biological factors predicting addiction relapse vulnerability. Curr Psychiatry Rep 13(5):398-405 (2011).
U.S. Appl. No. 17/145,093 Office Action dated Mar. 14, 2022.
Carrilho et al. A new facile synthesis of steroid dimers containing 17,17'-dicarboxamide spacers. Tetrahedron Letters 54:2763-2765 (2013).

* cited by examiner

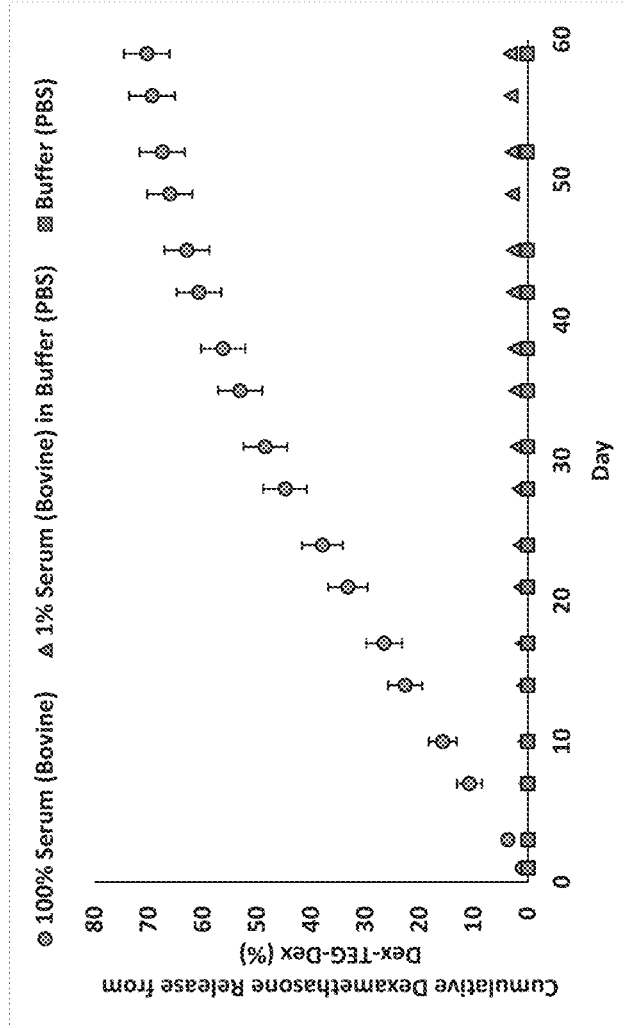

Compound 1

Negative Control

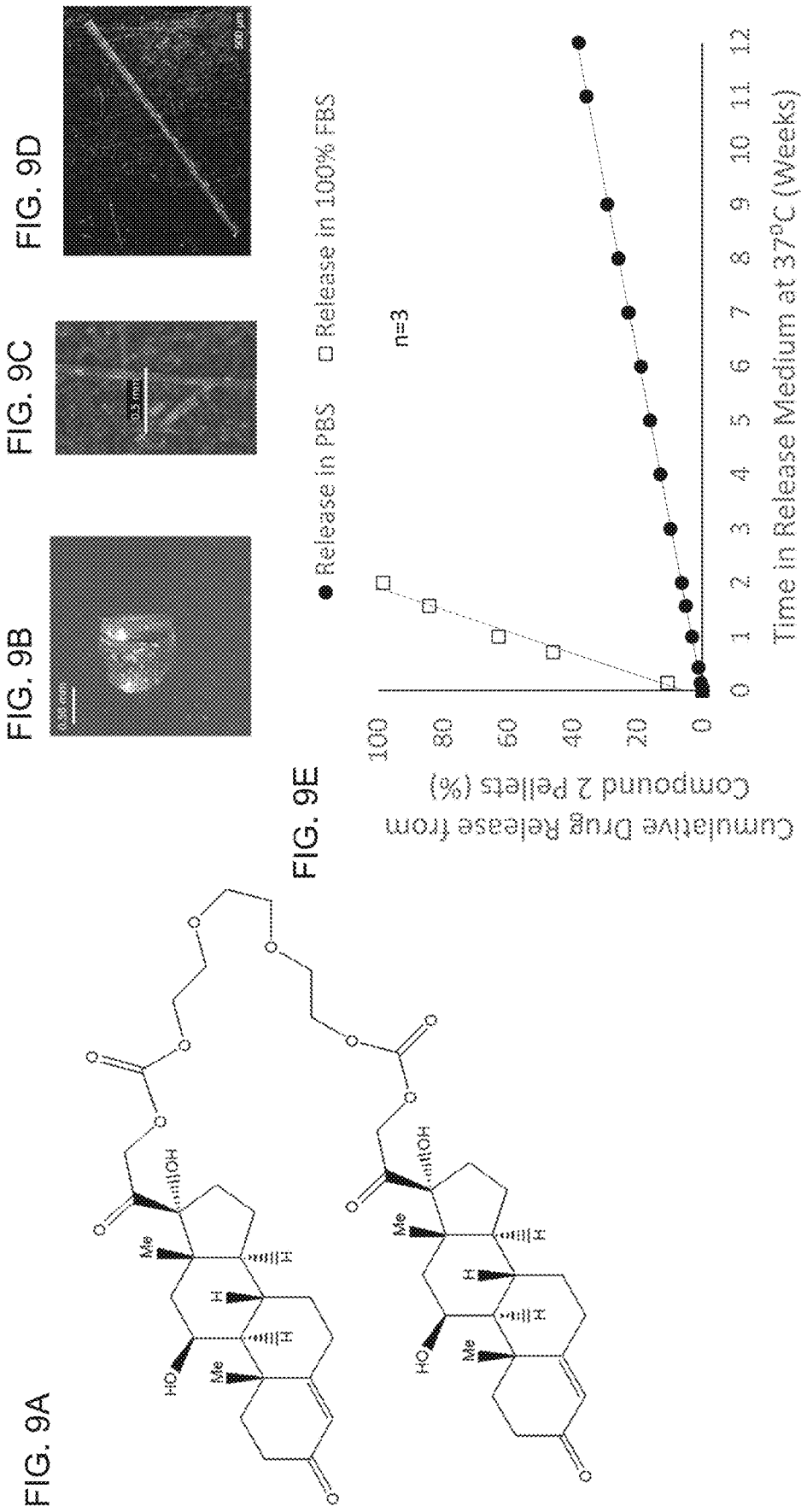

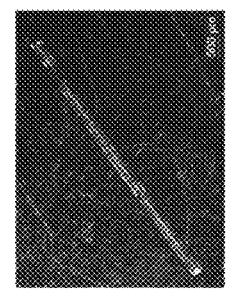
FIG. 12B
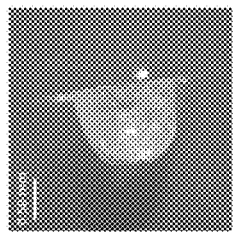
FIG. 12C
FIG. 12D
FIG. 12E
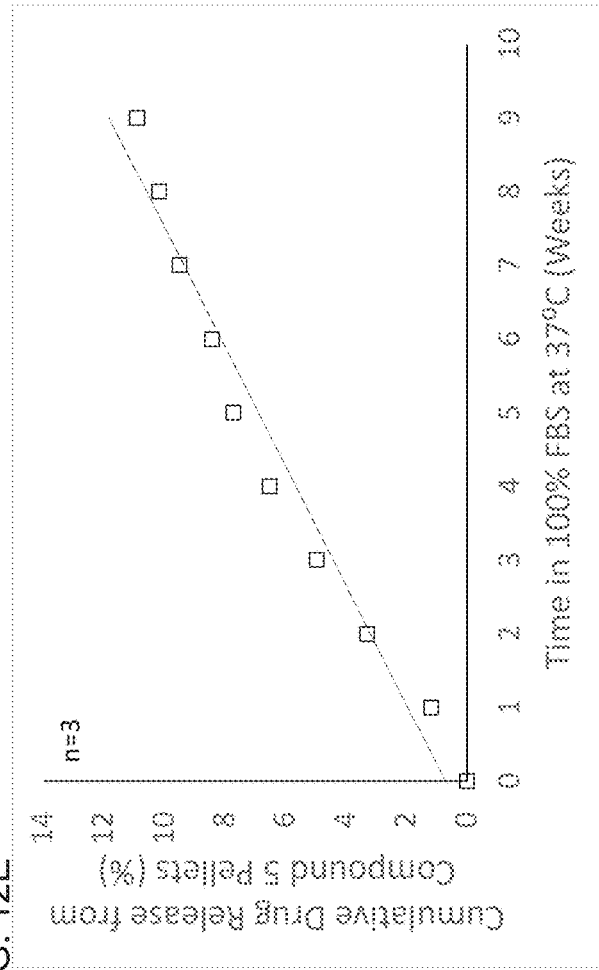
FIG. 12A
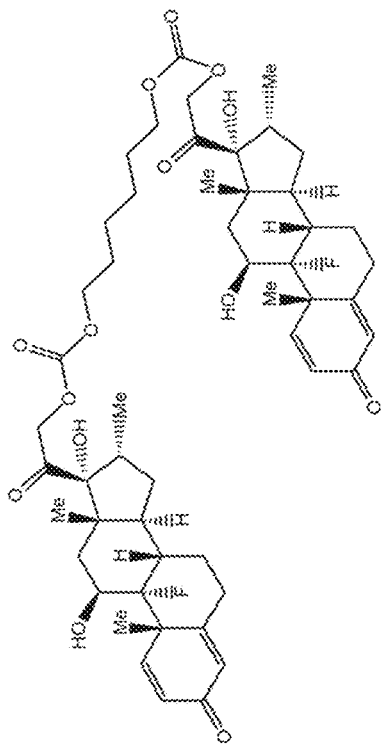

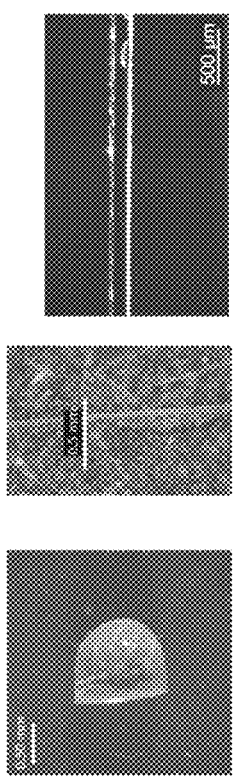
FIG. 13B
FIG. 13C
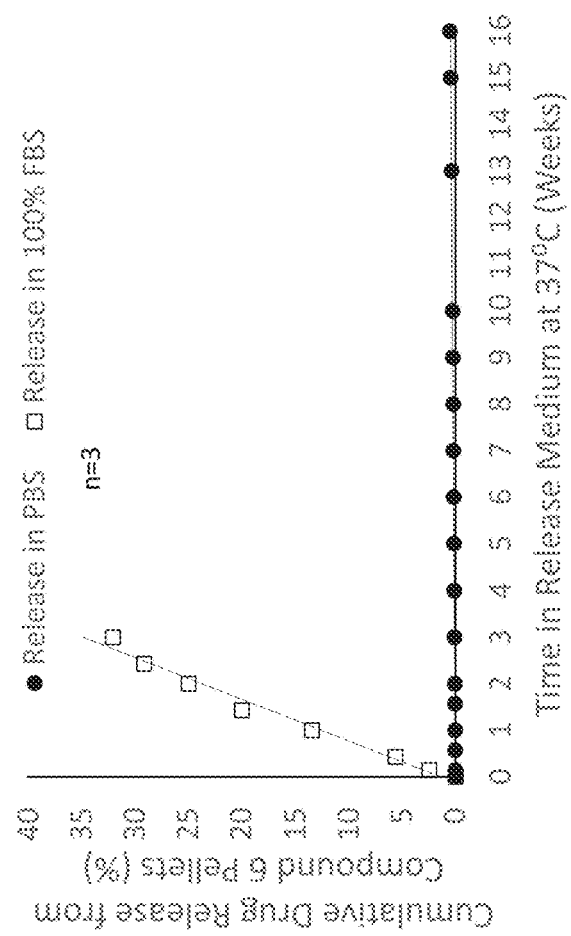
FIG. 13D
FIG. 13E
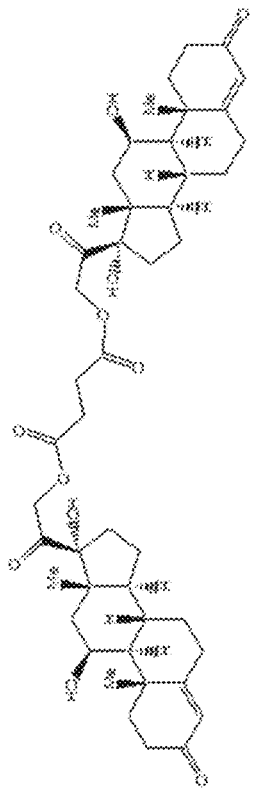
FIG. 13A

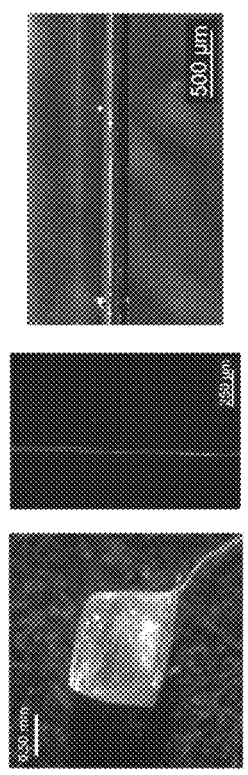
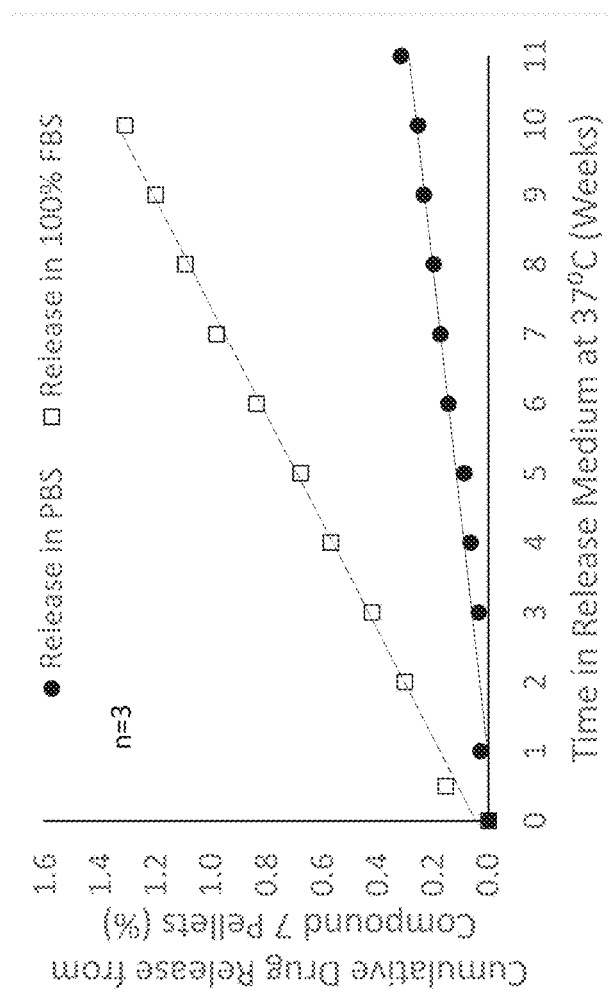
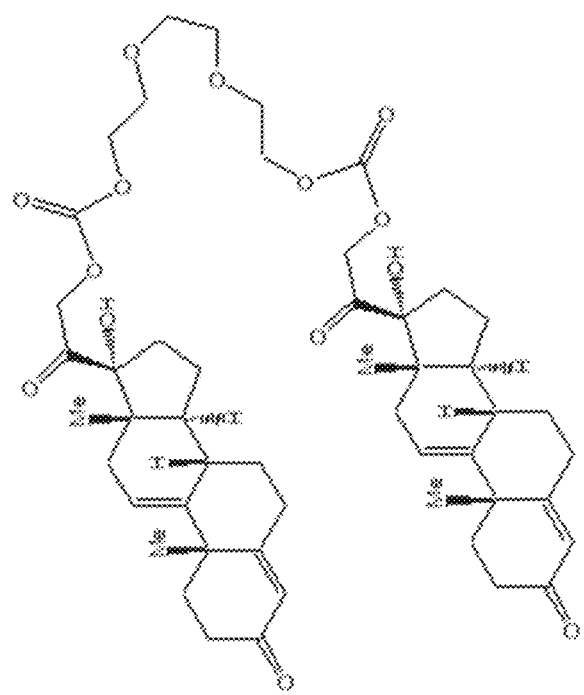

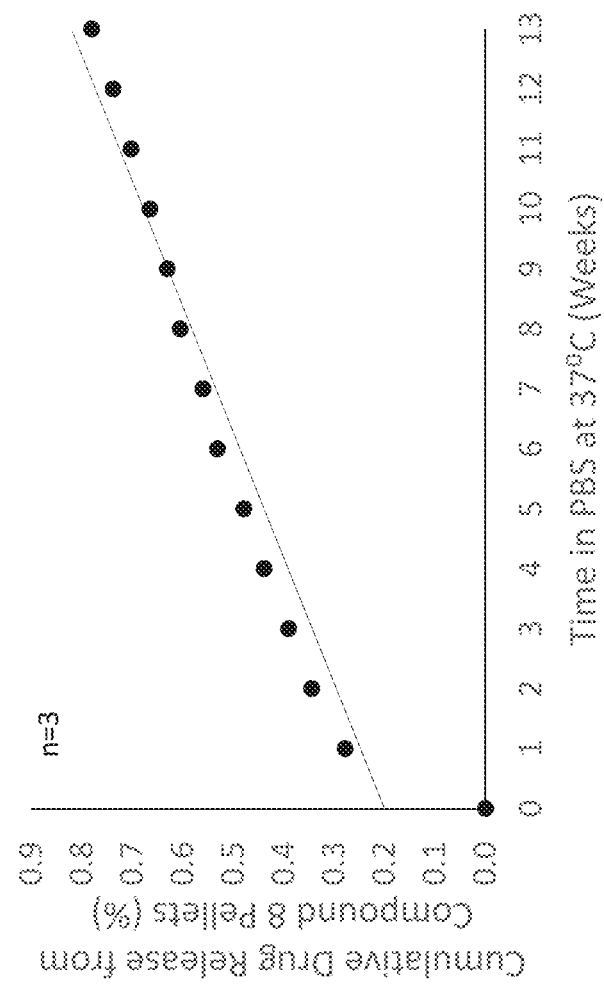
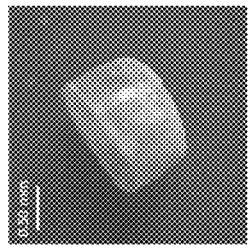
FIG. 15B
FIG. 15C
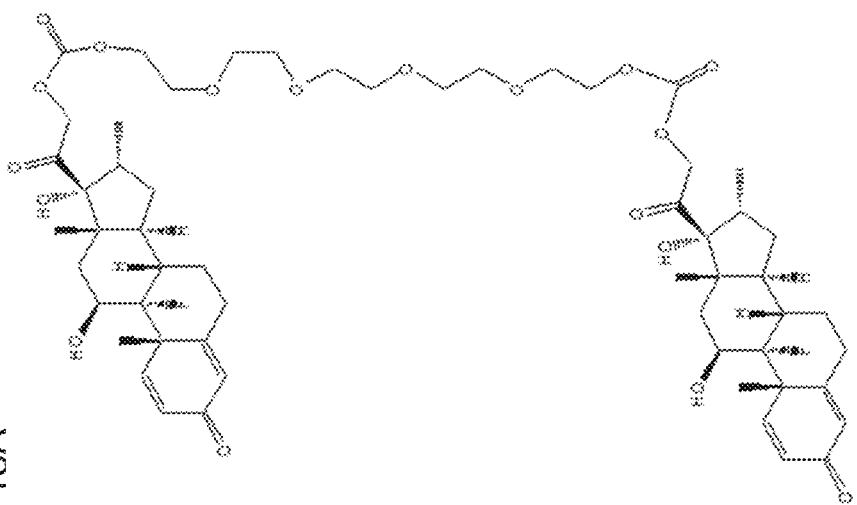
FIG. 15A

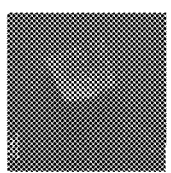
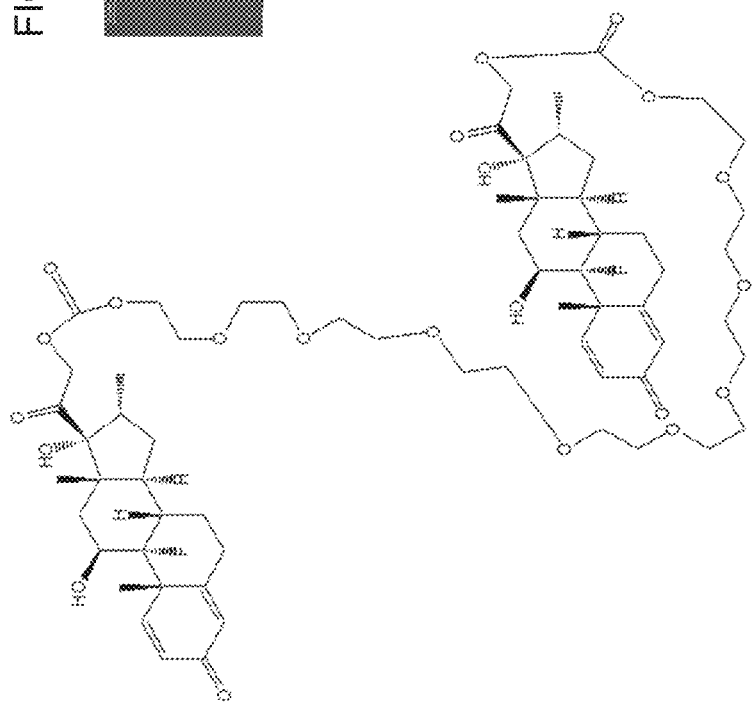
FIG. 19A    FIG. 19B
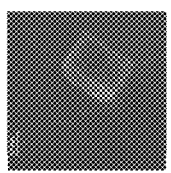
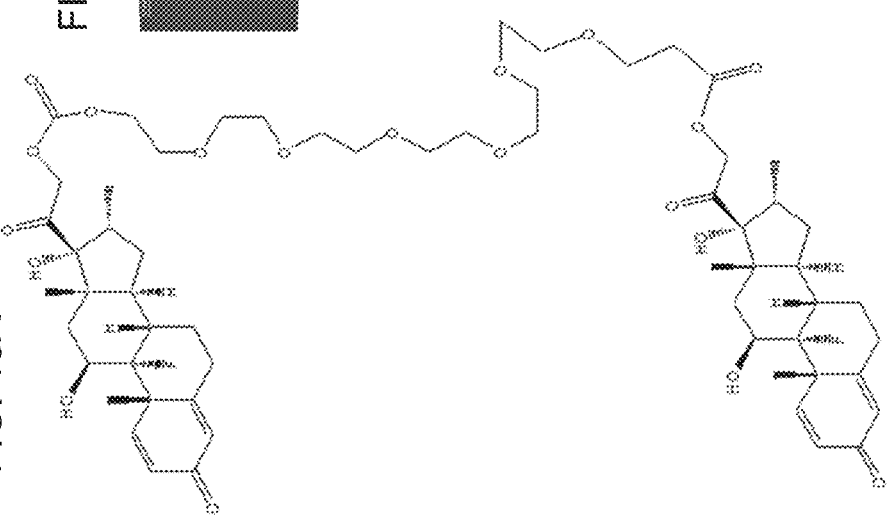
FIG. 18A    FIG. 18B

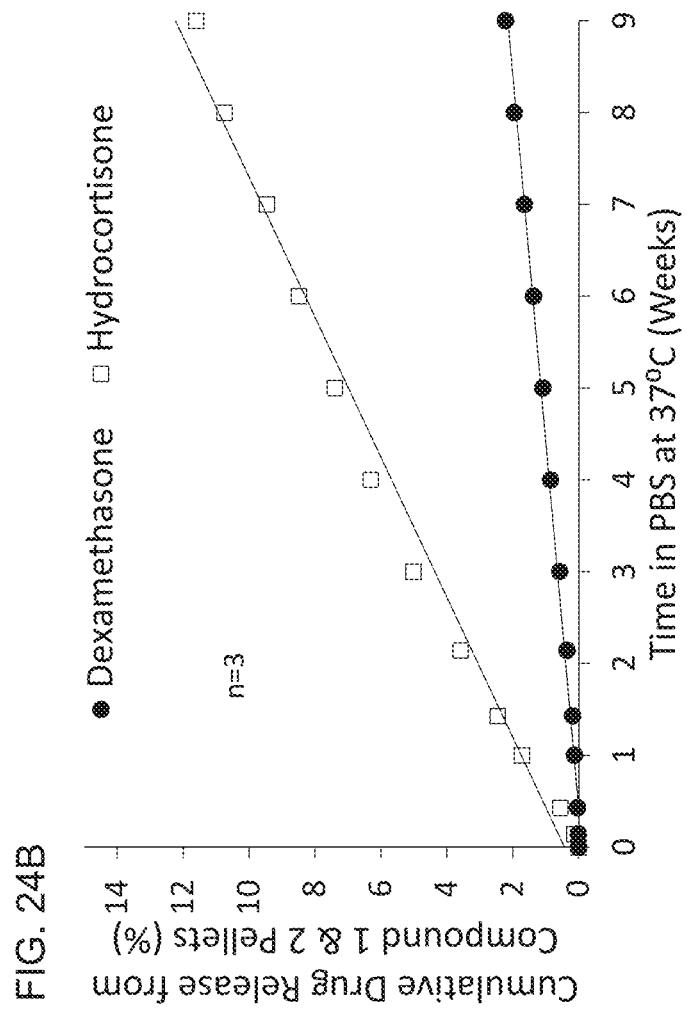
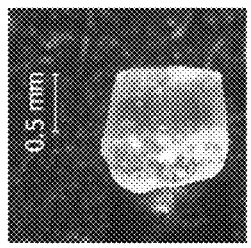
FIG. 24A
FIG. 24B

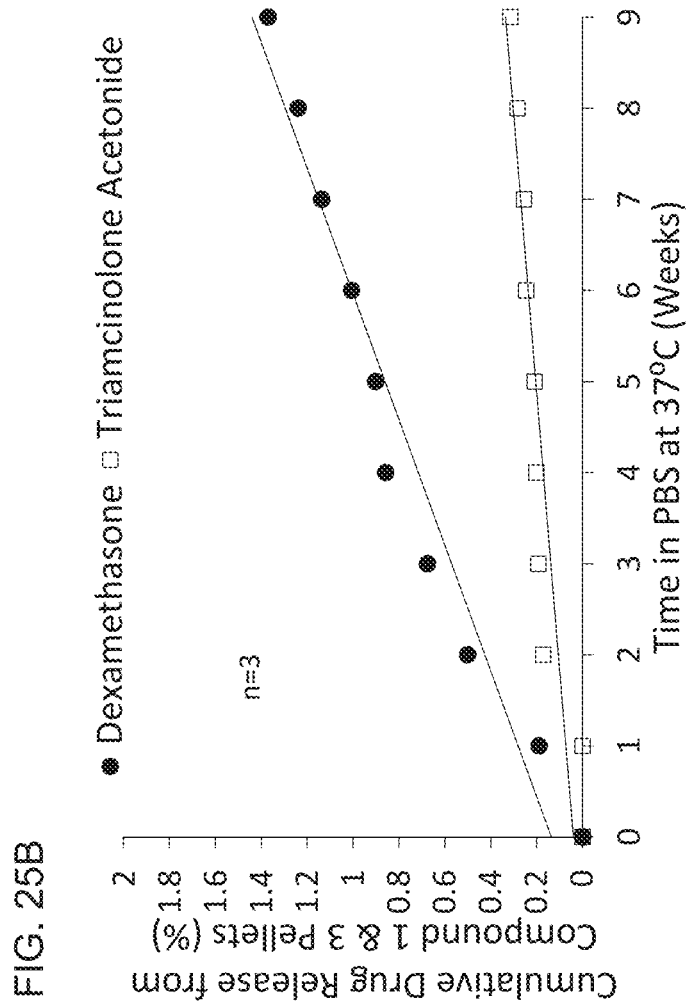
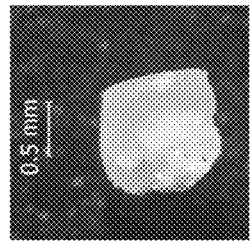
FIG. 25A
FIG. 25B

OCULAR INSERTS COMPRISING A COVALENTLY LINKED STEROID DIMER

RELATED APPLICATIONS

This application is US National Stage entry of PCT application PCT/CA2019/050133, filed Feb. 1, 2019, which claims the benefit of Provisional Patent Application No. 62/627,608, filed Feb. 7, 2018, Provisional Patent Application No. 62/625,460, filed Feb. 2, 2018; and Provisional Patent Application No. 62/758,234, filed Nov. 9, 2018, each of these applications being incorporated herein in their entirety by reference.

BACKGROUND OF THE DISCLOSURE

Steroids are useful drugs in ophthalmology, for example corticosteroids are used in the treatment of ocular inflammation associated with inflammatory diseases or following ocular surgery.

SUMMARY OF THE DISCLOSURE

The disclosure features ocular inserts that enable sustained release of ocular therapeutics, e.g., steroids.

In a first aspect, the disclosure features a method of treating an ocular condition in an eye of a subject in need thereof, said method including contacting the eye with an article formed from a compound of formula (A-I):

$$D1-L-D2 \quad (A-I),$$

or a pharmaceutically acceptable salt thereof, in which each of D1 and D2 is, independently, a radical formed from a steroid selected from an antibiotic steroid, a glucocorticoid steroid, an anti-angiogenic steroid, an intraocular pressure (TOP) lowering steroid, and a corticosteroid; and L is a linker covalently linking D1 to D2. In particular embodiments, the article is free of controlled release excipient, free of a crystallization inhibiting excipient, free of a mechanical integrity enhancing excipient, and/or free of a binding excipient; or the article optionally has a glassy state.

In certain embodiments, L is covalently linked to D1 and to D2 via one or more ester, carbonate, carbonate ester, or anhydride linkages.

In other embodiments, L is covalently linked to D1 and to D2 via one or more carbonate linkages.

In some embodiments, L includes the radical —C(O)—($R^A$)—C(O)— or —O—($R^A$)—O—; $R^A$ is a radical of a polyol and includes at least one free hydroxyl group or $R^A$ is selected from $C_{1-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—,
—(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and q, r, and s are integers from 1 to 10.

In certain embodiments, D1 and D2 are formed from the same steroid and the compound is further described by one of formulas (II-a)-(II-r). In other embodiments, D1 and D2 are formed from different steroids and each of D1 and D2 are, independently, further described by one of formulas (I-a)-(I-r).

In some embodiments, at least 70% (w/w) of the article is a compound of formula (A-I), e.g., at least 75% (w/w), at least 80% (w/w), at least 85% (w/w), at least 90% (w/w), at least 95% (w/w), or at least 99% (w/w). In particular embodiments, at least 90% (w/w) of the article is a compound of formula (A-I).

In other embodiments, the compound, D1, or D2 are released from the article through surface erosion.

In another embodiment of the methods of the disclosure, the compound is released from the article through surface erosion. In certain embodiments, the surface erosion releases less than 20% (e.g., less than 18%, 15%, 12%, 10%, or 5%) of D1 or D2 (as a percentage of the total drug, D1 or D2, present in the article in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments, the surface erosion releases less than 2.0% (e.g., less than 1.8%, 1.5%, 1.2%, 1.0%, or 0.5%) of D1 or D2 (as a percentage of the total drug, D1 or D2, present in the article in prodrug form) at 37° C. in PBS over 5 days, 7 days, 10 days, or 14 days (e.g., less than 2% of D1 or D2 at 37° C. in PBS over 5 days). In still other embodiments, the surface erosion releases greater than 20% (e.g., greater than 22%, 24%, 26%, 28%, or 30%) of D1 or D2 (as a percentage of the total drug, D1 or D2, present in the article in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments, the surface erosion releases greater than 5.0% (e.g., greater than 6.0%, 8.0%, 10%, 12%, or 15%) of D1 or D2 (as a percentage of the total drug, D1 or D2, present in the article in prodrug form) at 37° C. in PBS over not fewer than 6 days, 8 days, 10 days, or 12 days (e.g., greater than 5% of D1 or D2 at 37° C. in PBS over 10 days). The compound (D1 and/or D2) can be released from the article at a rate such that t10 is greater than or equal to ⅒ of t50.

In still another embodiment of any of the above articles, the article further includes from 0.1% to 10% (e.g., from 0.1 to 5%, from 0.1 to 2%, from 0.5 to 2%, from 1 to 10%) (w/w) of one or more additives, in which the one or more additives are plasticizers (e.g., glycerol, triacetin, isopropyl alcohol, ethanol, or ethylene glycol), antioxidants (e.g., ascorbic acid, vitamin E, sodium metabisulfite, butylated hydroxytoluene, p-hydroxybenxyl alcohol, or butylated hydroxy anisole), binders (e.g., polyvinyl pyrrolidone, carboxymethyl cellulose, hydroxypropyl cellulose, or hydroxypropyl methyl cellulose), lubricants, dyes, and mixtures thereof. In certain embodiments, the article further includes from 0.1% to 10% (w/w) of one or more additives, wherein the one or more additives are selected from plasticizers, antioxidants, binders, lubricants, dyes, and mixtures thereof.

In particular embodiments, the article is a fiber, fiber mesh, woven fabric, non-woven fabric, pellet, cylinder, microparticle (e.g., a microbead), nanoparticle (e.g., a nanobead), or shaped article.

In other embodiments, the article is in the form of glassy state fibers having a mean diameter of from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. In some embodiments, a mean length of the fiber can range from about 20 mm to 20 meters, e.g., 20 to 100 mm, 75 to 300 mm, 100 mm to 1 meter, 0.5 meters to 6 meters, or 1.0 meters to 20 meters.

In certain embodiments, the article is in the form of glassy state pellets having a mean diameter of from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

In some embodiments, the article is in the form of glassy state cylinders of from about 0.01 to 1 mm in diameter (e.g., about 0.01 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm) and 0.5 to 20 mm in length (e.g., about to 0.5 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm). In some embodiments, the length of the cylinder is about 0.5 to 10 mm, or about 1 to 10 mm.

In other embodiments, the article is in the form of glassy state microparticles, e.g., microbeads having a mean diameter of from about 1 to 1000 µm, e.g., about 10 to 1000 µm, about 100 to 1000 µm, about 200 to 1000 µm, about 500 to 1000 µm, about 700 to 1000 µm, or about 900 to 1000 µm.

In certain embodiments, the article is in the form of glassy state nanoparticles, e.g., nanobeads having a mean diameter of from about 0.01 to 1 µm, e.g., about 0.05 to 1 µm, about 0.1 to 1 µm, about 0.2 to 1 µm, about 0.3 to 1 µm, about 0.4 to 1 µm, about 0.5 to 1 µm, about 0.6 to 1 µm, about 0.7 to 1 µm, about 0.8 to 1 µm, or about 0.9 to 1 µm.

In certain embodiments, the article is in the form of a punctal plug, a stent, or a tube.

In particular embodiments of the claimed methods, the article is a fiber, a cylinder, a stent, or a tube.

In particular embodiments of any of the above methods, the article is administered by intravitreal, subretinal, or suprachoroidal injection into the eye of a subject. In some embodiments of the claimed methods, the article is a cylinder and the method further includes intravitreal, subretinal, or suprachoroidal injection of the article into the eye.

The ocular condition to be treated can be an inflammatory condition or a condition associated with a risk of developing inflammation. For example, the methods of the disclosure can be useful for the treatment of macular edema from retinal vein occlusion, diabetic macular edema, uveitis, diabetic retinopathy, or age-related macular degeneration (AMD).

For the treatment of ocular inflammation the compound of formula (A-1) can be selected such that, upon hydrolysis, D1 and D2 form a corticosteroid or a glucocorticoid steroid. For example, the compound can be a compound further described by the formula (III):

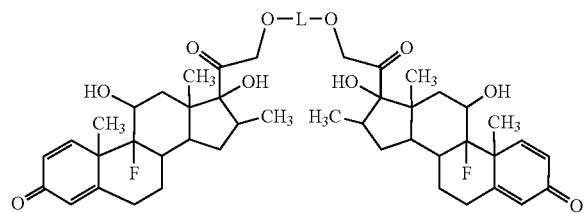

or a pharmaceutically acceptable salt thereof, wherein L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

The ocular condition can be a bacterial infection or a condition associated with a risk of developing a bacterial infection. For example, the methods of the disclosure can be useful for the treatment of conjunctivitis, keratitis, trachoma, or endophthalmitis.

For the treatment of bacterial infection the compound of formula (A-1) can be selected such that, upon hydrolysis, at least one of D1 and D2 form fusidic acid.

In particular embodiments, upon hydrolysis D1 and D2 form an anti-angiogenic steroid or an intraocular pressure (TOP) lowering steroid. For example, upon hydrolysis D1 and D2 form anecortave acetate, anecortave, 11-epicortisol, 17α-hydroxyprogesterone, tetrahydrocortexolone, or tetrahydrocortisol. The compound of formula (A-I) can be administered intravitreally to the eye of the subject, or can be administered to the suprachoroidal space of an eye of the subject. In some embodiments, the subject has age related macular degeneration, and upon hydrolysis D1 and D2 form an anti-angiogenic steroid, a corticosteroid, or a glucocorticosteroid. In certain embodiments, the subject has glaucoma, and upon hydrolysis D1 and D2 form an intraocular pressure (TOP) lowering steroid.

In an embodiment of any of the above aspects, O—(R$^A$)—O is a radical of a polyol formed from a cyclitol (e.g., bornesitol, conduritol, inositol, ononitol, pinitol, pinpollitol, quebrachitol, quinic acid, shikimic acid, valienol, or viscumitol), a sugar alcohol (e.g., sorbitol, mannitol, xylitol, maltitol, lactitol, erythritol, isomalt), or glycerin. In particular embodiments, the linker L is formed from a polyol and includes 1, 2, 3, or 4 hydroxyl groups. In another embodiment, O—(R$^A$)—O is a radical formed from an alkane diol (e.g., a C$_{1-10}$ diol), diethylene glycol, triethylene glycol, tetraethylene glycol, or pentaethylene glycol.

In other embodiments, the article is formed by a process including the steps of: (a) heating the compound, or a pharmaceutically acceptable salt thereof, to form a melt; and (b) heat molding the melt to form the article.

In particular embodiments, the article is formed by a process including the steps of: (a) heating the compound, or a pharmaceutically acceptable salt thereof, to form a melt; and (b) injection molding the melt to form the article.

In some embodiments, the article is formed by a process including the steps of: (a) heating the compound, or a pharmaceutically acceptable salt thereof, to form a melt; and (b) blow molding the melt to form the article.

In other embodiments, the article is formed by a process including the steps of: (a) dissolving the compound, or a pharmaceutically acceptable salt thereof, to form a solution; and (b) evaporating the solvent to form the article.

In certain embodiments, the article is formed by a process including the steps of: (a) dissolving the compound, or a pharmaceutically acceptable salt thereof, to form a solution; and (b) electrospinning, dry spinning, wet spinning, gel spinning, or electrospraying the solution to form the article.

In some embodiments, the article is formed by a process including the steps of: (a) heating the compound, or a pharmaceutically acceptable salt thereof, to form a melt; and (b) electrospinning or electrospraying the melt to form the article.

In particular embodiments, the article is formed by a process including the steps of: (a) heating the compound, or a pharmaceutically acceptable salt thereof, to form a melt; (b) extruding the melt to form the article.

Articles of the disclosure can be formed by the steps of (a) heating a compound of formula (A-I) above its melting point (e.g., depending upon the compound, heating to 110-145° C., 130-185° C., 150-215° C., or 180-240° C.) to form a melt, and (b) cooling the melt to form an article. The article can be shaped during step (a), prior to cooling, by pressing the melt into a mold, by extruding the melt from an orifice (e.g., to form a cylinder, stent, tube, or another shape), or by forming droplets of the melt and allowing the droplets to cool into glassy state droplets. Fibers can be formed by spinning (e.g. melt spinning), or pulling the melt (e.g., with tweezers) at different rates to yield glassy state fibers of different diameters.

Alternatively, articles of the disclosure can be formed by the steps of (a) dissolving a compound of formula (A-I) in a volatile organic solvent (e.g., acetone, methanol, dichloromethane, tetrahydrofuran, chloroform, or mixtures thereof) to form a solution, and (b) removing the organic solvent to form an article. The article can be shaped during step (b), prior to completely removing the organic solvent, by electrospraying, electrospinning, or fiber spinning the solution. For example, a 50:50 v/v mixture of dichloromethane/tetrahydrofuran at 100% wt/v solution of the compound can be loaded at a rate of 0.5 mL/h and electrospun onto a cylindrical mandrel rotating at 1150 rpm, forming aligned glassy state fibers. Fibers can be also formed by wet, dry, or gel spinning, or pulling the solution (e.g., with tweezers or other capture devices) at different rates, to form glassy state fibers of different diameters. Microparticles can be prepared by electrospraying a solution containing the compound at a concentration of about 20% to 40% w/v or 25% to 50% w/v of the solution. Nanoparticles can be prepared by electrospraying a solution containing the compound at a concentration of about 3% to 15% w/v or 5% to 18% w/v of the solution. Alternatively, a shaped article can be formed by placing the solution in a mold and evaporating the volatile organic solvent to form a shaped article.

The methods of the disclosure can include forming the article by a process including the steps of: (a) heating the compound, or a pharmaceutically acceptable salt thereof, to form a melt; (b) cooling the melt to form a glassy state composition; and (c) heating the glass state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article.

The methods of the disclosure can include forming the article by a process including the steps of: (a) dissolving the compound, or a pharmaceutically acceptable salt thereof, in a solvent to form a solution; (b) evaporating the solvent to form a glassy state composition; and (c) heating the glassy state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article.

The methods of the disclosure can further include forming the article by a process including the steps of: (a) dissolving the compound, or a pharmaceutically acceptable salt thereof, in a solvent to form a solution; (b) electrospraying or electrospinning the solution to form a glassy state composition; and (c) heating the glassy state composition to a temperature above the glass transition temperature of the glassy state composition and shaping the glassy state composition to form a coating.

In some embodiments of the methods of the disclosure, the compound is processed as described herein (e.g., melt processed or solvent processed) to form a glassy state solid. The glassy state solid is subsequently heated above its glass transition temperature, Tg, and molded or extruded to form a shaped article (e.g., a fiber, cylinder, stent, tube, microparticle (e.g., a microbead), or nanoparticle (e.g., a nanobead), or another shaped article).

In some embodiments of the methods and compositions of the disclosure, the article is free of controlled release excipient.

In particular embodiments of the methods and compositions of the disclosure, the article is free of a crystallization inhibiting excipient In certain embodiments of the methods and compositions of the disclosure, the article is free of a mechanical integrity enhancing excipient.

In particular embodiments of the methods and compositions of the disclosure, the article is free of a binding excipient.

In further embodiments of the methods and compositions of the disclosure, the article optionally has a glassy state.

The disclosure further features a compound of formula (II-n):

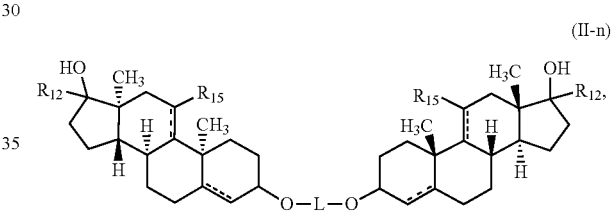

wherein $R_{12}$ represents —C(=O)CH$_2$OC(=O)CH$_3$, —C(=O)CH$_2$OH, or —C(=O)CH$_3$; $R_{15}$ represents H or OH; and L is —C(O)O—(R$^A$)—OC(O)— or —C(O)—OC(O)—(R$^A$)—C(O)O—C(O)—, and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. In particular embodiments, the compound is formed from anecortave acetate, anecortave, 11-epicortisol, 17α-hydroxyprogesterone, tetrahydrocortexolone, or tetrahydrocortisol.

The disclosure features a compound of formula (II-o):

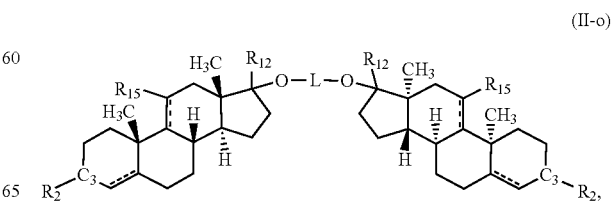

wherein the bond between $C_3$ and $R_2$ is a single or a double bond; $R_2$ represents OH or =O; $R_{12}$ represents —C(=O)CH$_2$OC(=O)CH$_3$, —C(=O)CH$_2$OH, or —C(=O)CH$_3$; $R_{15}$ represents H or OH; and L is —C(O)O—($R^A$)—OC(O)— or —C(O)—OC(O)—($R^A$)—C(O)O—C(O)—, and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_m$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. In particular embodiments, the compound is formed from anecortave acetate, anecortave, 11-epicortisol, 17α-hydroxyprogesterone, tetrahydrocortexolone, or tetrahydrocortisol.

The disclosure further features a compound of formula (II-p):

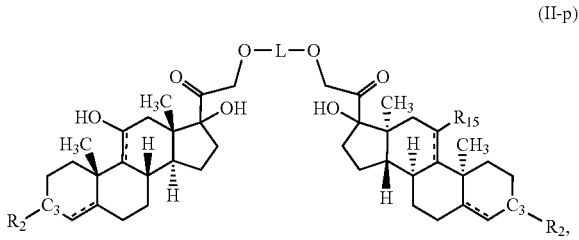

(II-p)

wherein the bond between $C_3$ and $R_2$ is a single or a double bond; $R_2$ represents OH or =O; $R_{15}$ represents H or OH; and L is —C(O)O—($R^A$)—OC(O)— or —C(O)—OC(O)—($R^A$)—C(O)O—C(O)—; and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. In particular embodiments, the compound is formed from anecortave, 11-epicortisol, tetrahydrocortexolone, or tetrahydrocortisol.

The disclosure further features a compound of formula (II-r):

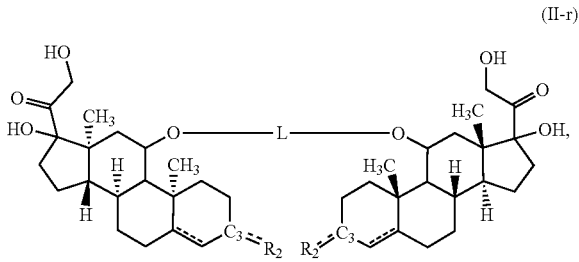

(II-r)

wherein the bond between $C_3$ and $R_2$ is a single or a double bond; $R_2$ represents OH or =O; and L is —C(O)O—($R^A$)—OC(O)— or —C(O)—OC(O)—($R^A$)—C(O)O—C(O)—; and $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. In particular embodiments, the compound is formed from 11-epicortisol or tetrahydrocortisol.

In another aspect, the disclosure features a method of treating the eye of a subject in need thereof, the method including:

(i) providing an article formed from a compound of formula (A-I):

$$D1\text{-}L\text{-}D2 \quad\quad (A\text{-}I),$$

or a pharmaceutically acceptable salt thereof, wherein each of D1 and D2 is, independently, a radical formed from a steroid selected from an antibiotic steroid, a glucocorticoid steroid, an IOP lowering steroid, and a corticosteroid; and L is a linker covalently linking D1 to D2, wherein the article is sized to provide a fluid passageway between the suprachoroidal space and the anterior chamber thereby reducing intraocular pressure in the eye; and (ii) inserting the article into a suprachoroidal space of the eye, wherein the article is positioned to extend from the suprachoroidal space to the anterior chamber of the eye to provide the fluid passageway, wherein the article is free of controlled release polymer (i.e., non-drug carrier), free of a crystallization inhibiting excipient, free of a mechanical integrity enhancing excipient, and/or free of a binding excipient; or wherein the article optionally has a glassy state. In particular embodiments, the article does not itself physically compromise flow in the canal with its presence.

In certain embodiments, L is covalently linked to D1 and to D2 via one or more ester, carbonate, carbonate ester, or anhydride linkages.

In other embodiments, L is covalently linked to D1 and to D2 via one or more carbonate linkages.

In some embodiments, L includes the radical —C(O)—($R^A$)—C(O)— or —O—($R^A$)—O—; $R^A$ is a radical of a polyol and includes at least one free hydroxyl group or $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and q, r, and s are integers from 1 to 10.

In certain embodiments, D1 and D2 are formed from the same steroid and the compound is further described by one of formulas (II-a)-(II-m). In other embodiments, D1 and D2 are formed from different steroids and each of D1 and D2 are, independently, further described by one of formulas (I-a)-(I-k).

In some embodiments, at least 70% (w/w) of the article is a compound of formula (A-I), e.g., at least 75% (w/w), at least 80% (w/w), at least 85% (w/w), at least 90% (w/w), at least 95% (w/w), at least 98% (w/w), or at least 99% (w/w). In particular embodiments, at least 90% (w/w) of the article is a compound of formula (A-I).

In other embodiments, the compound, D1, or D2 are released from the article through surface erosion.

In another embodiment of the methods of the disclosure, the compound is released from the article through surface erosion. In certain embodiments, the surface erosion releases less than 20% (e.g., less than 18%, 15%, 12%, 10%, or 5%) of D1 or D2 (as a percentage of the total drug, D1 or D2, present in the article in prodrug form) at 37° C. in 100% bovine serum over 5 days, 6 days, 7 days, 8 days, 9 days, 10 days, or 12 days (e.g., less than 10% of D1 or D2 at 37° C. in 100% bovine serum over 5 days). In other embodiments, the surface erosion releases less than 2.0% (e.g., less than 1.8%, 1.5%, 1.2%, 1.0%, or 0.5%) of D1 or D2 (as a percentage of the total drug, D1 or D2, present in the article in prodrug form) at 37° C. in PBS over 5 days, 7 days, 10 days, or 14 days (e.g., less than 2% of D1 or D2 at 37° C. in PBS over 5 days). In still other embodiments, the surface erosion releases greater than 20% (e.g., greater than 22%, 24%, 26%, 28%, or 30%) of D1 or D2 (as a percentage of the total drug, D1 or D2, present in the article in prodrug form) at 37° C. in 100% bovine serum over not fewer than 6 days, 8 days, 10 days, or 12 days (e.g., greater than 24% of D1 or D2 at 37° C. in 100% bovine serum over 10 days). In other embodiments, the surface erosion releases greater than 5.0% (e.g., greater than 6.0%, 8.0%, 10%, 12%, or 15%) of D1 or D2 (as a percentage of the total drug, D1 or D2, present in the article in prodrug form) at 37° C. in PBS over not fewer than 6 days, 8 days, 10 days, or 12 days (e.g., greater than 5% of D1 or D2 at 37° C. in PBS over 10 days). The compound (D1 and/or D2) can be released from the article at a rate such that $t_{10}$ is greater than or equal to $\frac{1}{10}$ of $t_{50}$.

In still another embodiment of any of the above articles, the article further includes from 0.1% to 10% (e.g., from 0.1 to 5%, from 0.1 to 2%, from 0.5 to 2%, from 1 to 10%) (w/w) of one or more additives, in which the one or more additives are plasticizers (e.g., glycerol, triacetin, isopropyl alcohol, ethanol, or ethylene glycol), antioxidants (e.g., ascorbic acid, vitamin E, sodium metabisulfite, butylated hydroxytoluene, p-hydroxybenxyl alcohol, or butylated hydroxy anisole), binders (e.g., polyvinyl pyrrolidone, carboxymethyl cellulose, hydroxypropyl cellulose, or hydroxypropyl methyl cellulose, optionally polymers having an average size of less than 50 kDa, 25 kDa, 15 kDa, or less than 10 kDa), lubricants, dyes, and mixtures thereof. In certain embodiments, the article further includes from 0.1% to 10% (w/w) of one or more additives, wherein the one or more additives are selected from plasticizers, antioxidants, binders, lubricants, dyes, and mixtures thereof.

In particular embodiments of any of the above methods, the article is a fiber, a cylinder, a stent, or a tube.

In other embodiments, the article is in the form of glassy state fibers having a mean diameter of from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. In some embodiments, a mean length of the fiber can range from about 20 mm to 20 meters, e.g., 20 to 100 mm, 75 to 300 mm, 100 mm to 1 meter, 0.5 meters to 6 meters, or 1.0 meters to 20 meters.

In particular embodiments of any of the above methods, the article is positioned and sized to support the Schlemm's canal and keep the Schlemm's canal open.

In other embodiments of any of the above methods, the ocular condition is an inflammatory condition. For example, the methods of the disclosure can be performed to reduce inflammation associated with cataract surgery or inflammation associated with glaucoma surgery.

For the treatment of ocular inflammation the compound of formula (A-1) can be selected such that, upon hydrolysis, D1 and D2 form a corticosteroid or a glucocorticoid steroid. For example, the compound can be a compound further described by the formula (III):

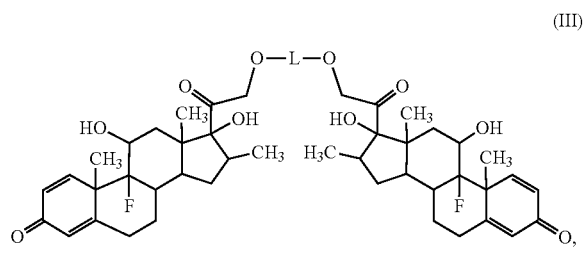

or a pharmaceutically acceptable salt thereof, wherein L is —C(O)O—(R$^4$)—OC(O)—, —C(O)—OC(O)—(R$^4$)—C(O)O—C(O)—; R$^4$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^4$)—O is a radical of a polyol and includes at least one free hydroxyl group or O—(R$^4$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

The ocular condition can be a bacterial infection or a condition associated with a risk of developing a bacterial infection. For example, the methods of the disclosure can be useful for the treatment of conjunctivitis, keratitis, trachoma, or endophthalmitis.

For the treatment of bacterial infection the compound of formula (A-1) can be selected such that, upon hydrolysis, at least one of D1 and D2 form fusidic acid.

In an embodiment of any of the above aspects, O—(R$^4$)—O is a radical of a polyol formed from a cyclitol (e.g., bornesitol, conduritol, inositol, ononitol, pinitol, pinpollitol, quebrachitol, quinic acid, shikimic acid, valienol, or viscumitol), a sugar alcohol (e.g., sorbitol, mannitol, xylitol, maltitol, lactitol, erythritol, isomalt), or glycerin. In particular embodiments, the linker L is formed from a polyol and includes 1, 2, 3, or 4 hydroxyl groups. In another embodiment, O—(R$^4$)—O is a radical formed from an alkane diol (e.g., a C1-10 diol), diethylene glycol, triethylene glycol, tetraethylene glycol, or pentaethylene glycol.

In other embodiments, the article is formed by a process including the steps of: (a) heating the compound, or a pharmaceutically acceptable salt thereof, to form a melt; and (b) heat molding the melt to form the article.

In particular embodiments, the article is formed by a process including the steps of: (a) heating the compound, or a pharmaceutically acceptable salt thereof, to form a melt; and (b) injection molding the melt to form the article.

In some embodiments, the article is formed by a process including the steps of: (a) heating the compound, or a pharmaceutically acceptable salt thereof, to form a melt; and (b) blow molding the melt to form the article.

In other embodiments, the article is formed by a process including the steps of: (a) dissolving the compound, or a pharmaceutically acceptable salt thereof, to form a solution; and (b) evaporating the solvent to form the article.

In certain embodiments, the article is formed by a process including the steps of: (a) dissolving the compound, or a pharmaceutically acceptable salt thereof, to form a solution; and (b) electrospinning, dry spinning, wet spinning, gel spinning, or electrospraying the solution to form the article.

In some embodiments, the article is formed by a process including the steps of: (a) heating the compound, or a pharmaceutically acceptable salt thereof, to form a melt; and (b) electrospinning or electrospraying the melt to form the article.

In particular embodiments, the article is formed by a process including the steps of: (a) heating the compound, or a pharmaceutically acceptable salt thereof, to form a melt; (b) extruding the melt to form the article.

Articles of the disclosure can be formed by the steps of (a) heating a compound of formula (A-I) above its melting point (e.g., depending upon the compound, heating to 110-145° C., 130-185° C., 150-215° C., or 180-240° C.) to form a melt, and (b) cooling the melt to form an article. The article can be shaped during step (a), prior to cooling, by pressing the melt into a mold, by extruding the melt from an orifice (e.g., to form a cylinder, stent, tube, or another shape), or by forming droplets of the melt and allowing the droplets to cool into glassy state droplets. Fibers can be formed by spinning (e.g. melt spinning, or electrospinning), or pulling the melt (e.g., with tweezers) at different rates to yield glassy state fibers of different diameters.

Alternatively, articles of the disclosure can be formed by the steps of (a) dissolving a compound of formula (A-I) in a volatile organic solvent (e.g., acetone, methanol, dichloromethane, tetrahydrofuran, chloroform, or mixtures thereof) to form a solution, and (b) removing the organic solvent to form an article. The article can be shaped during step (b), prior to completely removing the organic solvent, by electrospraying, electrospinning, or fiber spinning the solution. For example, a 50:50 v/v mixture of dichloromethane/tetrahydrofuran at 100% wt/v solution of the compound can be loaded at a rate of 0.5 mL/h and electrospun onto a cylindrical mandrel rotating at 1150 rpm, forming aligned glassy state fibers. Fibers can be also formed by wet, dry, or gel spinning, or pulling the solution (e.g., with tweezers) at different rates, to form glassy state fibers of different diameters. Microparticles can be prepared by electrospraying a solution containing the compound at a concentration of about 20% to 40% w/v or 25% to 50% w/v of the solution. Nanoparticles can be prepared by electrospraying a solution containing the compound at a concentration of about 3% to 15% w/v or 5% to 18% w/v of the solution. Alternatively, a shaped article can be formed by placing the solution in a mold and evaporating the volatile organic solvent to form a shaped article.

The methods of the disclosure can include forming the article by a process including the steps of: (a) heating the compound, or a pharmaceutically acceptable salt thereof, to form a melt; (b) cooling the melt to form a glassy state composition; and (c) heating the glassy state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article.

The methods of the disclosure can include forming the article by a process including the steps of: (a) dissolving the compound, or a pharmaceutically acceptable salt thereof, in a solvent to form a solution; (b) evaporating the solvent to form a glassy state composition; and (c) heating the glassy state composition to a temperature above the glass transition temperature of the glassy state composition and shaping the glassy state composition to form a shaped article. Step (c) can include extruding, molding, blow molding, heat spinning, electrospinning, or electrospraying the glassy state composition to form the shaped article.

The methods of the disclosure can further include forming the article by a process including the steps of: (a) dissolving the compound, or a pharmaceutically acceptable salt thereof, in a solvent to form a solution; (b) electrospraying or electrospinning the solution to form a glassy state composition; and (c) heating the glassy state composition to a temperature above the glass transition temperature of the glassy state composition and shaping the glassy state composition to form a coating.

In some embodiments of the methods of the disclosure, the compound is processed as described herein (e.g., melt processed or solvent processed) to form a glassy state solid. The glassy state solid is subsequently heated above its glass transition temperature, Tg, and molded or extruded to form a shaped article (e.g., a fiber, cylinder, stent, or tube).

In some embodiments of the methods of the disclosure, the article comprises less than 5% (e.g., less than 4%, less than 3%, less than 2%, or less than 1%) (w/w) of polymeric material of greater than 5 kDa.

In some embodiments of the methods of the disclosure, the article is free of controlled release polymer.

In particular embodiments of the methods of the disclosure, the article is free of a crystallization inhibiting excipient In certain embodiments of the methods of the disclosure, the article is free of a mechanical integrity enhancing excipient.

In further embodiments of the methods of the disclosure, the article is free of a binding excipient.

In some embodiments of the methods of the disclosure, the article is a glassy state composition. In further embodiments, drug release from the article exhibits a $t_{10}$ that is equal to or greater than ⅒ of $t_{50}$ when the drug release from the article is measured at 37° C. in phosphate buffered saline or in bovine serum.

Definitions

The term "free of controlled release polymer," as used herein, refers to the absence of an amount of a polymeric material of greater than 10 KDa in the articles of the disclosure that is sufficient to delay or slow the release of the steroid dimer from the article in comparison to the release profile observed for an otherwise identical article containing none of the polymeric material, where the release profile is measured at 37° C. in 100% fetal bovine serum (FBS).

The term "free of a crystallization inhibiting excipient," as used herein, refers to the absence of an amount of an excipient in the articles of the disclosure that is sufficient to reduce the amount of crystalline steroid dimer in the article in comparison to the amount of crystalline steroid dimer observed in an otherwise identical article containing none of the excipient. The level of crystallinity can be measured using DSC or XRD. In particular embodiments, the articles of the disclosure are free of a crystallization inhibiting excipient that is a polymeric material of greater than 10 KDa.

The term "free of a mechanical integrity enhancing excipient," as used herein, refers to the absence of an amount of an excipient in the articles of the disclosure that is sufficient to increase the mechanical integrity of the article in comparison to the mechanical integrity of an otherwise identical article containing none of the excipient. The mechanical integrity of an article can be tested using a 3- or 4-point mechanical bend test (ASTM C1684-18) on the formulation with or without the excipient with the article in the shape of a rod either in the dry state (prior to drug release) or after 15-30% drug release. For articles with a rectangular shape, the mechanical integrity can be tested using a 3-point mechanical bend test (ASTM D790-17) or 4-point mechanical bend test (ASTM D6272) on the formulation with or without excipient either in the dry state (prior to drug release) or after 15-30% drug release. A reduction in mechanical integrity causes the articles to break apart sooner, increasing the total surface area of the quantity of articles, and resulting in a more rapid release profile, where the release profile is measured at 37° C. in 100% FBS. In particular embodiments, the articles of the disclosure are free of a mechanical integrity enhancing excipient that is a polymeric material of greater than 10 KDa.

The term "free of a binding excipient," as used herein, refers to the absence of an amount of an excipient in the articles of the disclosure that is sufficient to delay or slow the release of the steroid dimer from the article in comparison to the release profile observed for an otherwise identical article containing none of the binding excipient, where the release profile is measured at 37° C. in 100% FBS.

The term "anti-angiogenic steroid" refers to a steroid that is capable of inhibiting the growth of new blood vessels (i.e., angiogenesis). Examples of anti-angiogenic steroids include anecortave acetate, anecortave, 11-epicortisol, 17α-hydroxyprogesterone, tetrahydrocortexolone, and tetrahydrocortisol.

The term "glassy state," as used herein, refers to an amorphous solid including greater than 70%, 80%, 90%, 95%, 98%, or 99% (w/w) of one or more drug dimers of the disclosure and exhibiting a glass transition temperature in the range of from 38 to 150° C. In the glassy state, as measured by DSC or XRD, the level of crystallinity is low, ranging from 0-15%, e.g., 0-1%, 0-3%, 0-5%, 0-7%, 0-9%, 0-10%, or 0-13%. Glass formulations of the disclosure can be formed using heat processing or solvent processing one or more drug dimers.

The term "cylinder," as used herein, refers to the shape of the pharmaceutical compositions of the disclosure that has parallel sides and a circular or oval cross section, or a shaped cross section (e.g., a star shaped cross section). A mean diameter of the cylinder can range from about 0.01 to 1 mm diameter, e.g., about 0.01 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm. A mean length of the cylinder can range from about 0.05 to 20 mm, e.g., about 0.05 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm. In some embodiments, the mean diameter of the cylinder is in the range of about 0.01 to 1 mm and the mean length of the cylinder is about 0.1 mm to 4.0 mm. In some embodiments, the mean length of the cylinder is about 0.5 to 10 mm, or about 1 to 10 mm.

The term "fiber," as used herein, refers to the shape of the pharmaceutical compositions of the disclosure that is elongated or threadlike. A mean diameter of the fiber can range from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. In some embodiments, a mean length of the fiber can range from about 20 mm to 20 meters, e.g., about 20 to 1000 mm, about 20 to 2,000 mm, about 100 to 2,000 mm, about 100 to 5,000 mm, about 1,000 to 8,000 mm, about 2,000 to 8,000 mm, about 2,000 to 10,000 mm, about 2,000 to 12,000 mm, about 2,000 to 15,000 mm, or about 5,000 to 18,000 mm.

The term "fiber mesh," as used herein, refers to a web or a net in having many attached or woven fibers. The fiber mesh can have aligned and unaligned morphologies.

The term "intraocular pressure (TOP) lowering steroid" refers to a steroid that is capable of lowering intraocular pressure following administration to the eye of a subject. Examples of intraocular pressure (TOP) lowering steroids include anecortave acetate, anecortave, 11-epicortisol, 17α-hydroxyprogesterone, tetrahydrocortexolone, and tetrahydrocortisol.

The term "microparticle," as used herein, refers to the shape of the pharmaceutical compositions of the disclosure, which can be regularly or irregularly shaped. A mean diameter of the microparticle can range from about 1 to 1000 μm, e.g., about 10 to 1000 μm, about 100 to 1000 μm, about 200 to 1000 μm, about 500 to 1000 μm, about 700 to 1000 μm, or about 900 to 1000 μm. As used herein, a "microbead" refers to a microparticle that is spherical.

The term "nanoparticle," as used herein, refers to the shape of the pharmaceutical compositions of the disclosure, which can be regularly or irregularly shaped. A mean diameter of the nanoparticle can range from about 0.01 to 1 μm, e.g., about 0.05 to 1 μm, about 0.1 to 1 μm, about 0.2 to 1 μm, about 0.3 to 1 μm, about 0.4 to 1 μm, about 0.5 to 1 μm, about 0.6 to 1 μm, about 0.7 to 1 μm, about 0.8 to 1 μm, or about 0.9 to 1 μm. As used herein, a "nanobead" refers to a nanoparticle that is spherical.

The term "non-woven fabric," as used herein, refers to a web structure bonded together by entangling fibers.

An "ocular disease or condition" as used herein is a disease or condition that affects or involves the eye or one or more parts of the eye. The parts of the eye are known to those of skill in the art and, broadly speaking, include the eyeball and the tissues and fluids which constitute the eyeball, the periocular muscles and the portion of the optic nerve which is within or adjacent to the eyeball.

The term "pellet," as used herein, refers to the shape of the pharmaceutical compositions of the disclosure that is rounded, spherical, or cylindrical, or a combination thereof. A mean diameter of the pellet can range from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

The term "pharmaceutically acceptable salt" as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in J. Pharm. Sci. 66:1-19, 1977. The salts can be prepared in situ during the final isolation and purification of the compounds of the disclosure or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, carbonate, chloride, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "stent," as used herein refers to a tubular support in which the walls of the tube are optionally porous and wherein the stent has a mean diameter in its shortest dimension ranging from about 120 to 350 µm, e.g., 120 to 140 µm, 120 to 160 µm, 120 to 180 µm, 120 to 200 µm, 120 to 220 µm, 120 to 240 µm, 120 to 260 µm, 120 to 280 µm, 120 to 300 µm, 120 to 320 µm, or 120 to 340 µm. In some embodiments, the mean length of the stent is in the range of about 0.05 to 10 mm, e.g., 0.5 to 10 mm, 1.0 to 8.0 mm, 0.5 to 6.0 mm, or 2.5 to 8.0 mm. In some embodiments, the mean diameter of the stent is in the range of about 0.01 to 1 mm and the mean length of the stent is about 0.5 to 10 mm.

The term "surface erosion," as used herein refers to a process of a gradual disintegration of the pharmaceutical compositions of the disclosure and release of a free drug from the drug dimer. Surface erosion can be tailored to achieve desired drug release rates. Surface erosion can depend on the drug composition of the drug dimer, and can be modulated by the cleavage of drug-linker bond through hydrolysis and/or enzymatic degradation. The rate of surface erosion and release of a given drug from a drug dimer can also depend on the quantity of the loaded drug dimer as a percent of the final drug dimer formulation, article size, solubility of drug dimer (e.g., through selection of appropriate drug and/or linker), and/or surface area of the article. For example, surface erosion mechanism of drug release allows drug delivery articles to be tailored with specific physical features (dimensions, diameters, surface areas, total mass, etc.) to achieve desired drug release rates, and drug release can be designed to be initiated within minutes or hours, and may continue to occur over days, weeks, months, or years.

As used herein, "$t_{50}$" is the time at which 50% of the releasable drug has been released from an article of the disclosure. Time $t_{10}$ is, correspondingly, the time at which 10% of the releasable drug has been released from an article of the disclosure. When the release curve is perfectly linear, $t_{10}=\frac{1}{5}$ of $t_{50}$. When there is an initial burst of released drug, $t_{10}$ is much less than $\frac{1}{5}$ of t50. In the compositions and methods of the disclosure $t_{10}$ can be equal to or greater than $\frac{1}{10}$ of $t_{50}$. Drug release from an article or compound of the disclosure can be measured at 37° C. in 100% bovine serum, or at 37° C. in PBS, as described in Example 1.

The term "tube" refers to a hollow, cylindrical body with a mean diameter ranging from about 120 to 350 µm, e.g., 120 to 140 µm, 120 to 160 µm, 120 to 180 µm, 120 to 200 µm, 120 to 220 µm, 120 to 240 µm, 120 to 260 µm, 120 to 280 µm, 120 to 300 µm, 120 to 320 µm, or 120 to 340 µm. In some embodiments, the mean length of the tube is in the range of about 0.05 to 10 mm, e.g., 0.5 to 10 mm, 1.0 to 8.0 mm, 0.5 to 6.0 mm, or 2.5 to 8.0 mm. In some embodiments, the mean diameter of the tube is in the range of about 0.01 to 1 mm and the mean length of the tube is about 0.5 to 10 mm.

The term "woven fabric," as used herein, refers to pharmaceutical compositions that resemble materials that are formed by weaving of fibers.

As used herein, "treating" refers to administering a compound or composition as described herein, for prophylactic, adjunctive, and/or therapeutic purposes. A "prophylactic" use refers to reducing the likelihood or severity of a condition or disease in a subject who is not yet ill, but who is susceptible to, or otherwise at risk of, a particular disease by administering treatment to the subject. To "treat disease" refers to administering treatment to a subject already suffering from a disease to improve or stabilize the subject's condition. Thus, in the claims and embodiments, treating is the administration to a subject either for therapeutic or prophylactic purposes.

Chemical Definitions

By "acyl" is meant a chemical moiety with the formula —C(O)R', where R' is selected from the group consisting of $C_{1-10}$ alkyl, $C_{2-20}$ alkene, heteroalkyl, $C_{2-20}$ alkyne, $C_{5-10}$ aryl, and cyclic system. Examples of acyl groups include, without limitation, acetyl, propanoyl, butanoyl, pentanoyl, and tetrahydrofuran-2-oyl.

By "aliphatic" is meant a non-aromatic chemical moiety of hydrocarbons. Aliphatics may be cyclic, straight, or branched chains, and may be saturated or unsaturated, and may have single, double, or triple bonds.

By "alkoxy" is meant a chemical substituent of the formula —OR, wherein R is an alkyl group. By "aryloxy" is meant a chemical substituent of the formula —OR, wherein R is a $C_{5-10}$ aryl group.

As used herein, the terms "alkylene," "alkenylene," "alkynylene," and the prefix "alk" refer to divalent groups having a specified size, typically $C_{1-10}$ or $C_{1-20}$ for the saturated groups (e.g., alkylene or alk) and $C_{2-20}$ or $C_{2-20}$ for the unsaturated groups (e.g., alkenylene or alkynylene). They include straight-chain, branched-chain, and cyclic forms as well as combinations of these, containing only C and H when unsubstituted. Because they are divalent, they can link together two parts of a molecule. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example.

By "alkylthio" is meant a chemical substituent of the formula —SR, wherein R is an alkyl group.

By "arylthio" is meant a chemical substituent of the formula —SR, wherein R is a $C_{5-10}$ aryl group.

By "$C_{1-20}$ alkyl" is meant a branched or unbranched saturated hydrocarbon group, having 1 to 20 carbon atoms, inclusive. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{2-20}$ alkene" is meant a branched or unbranched hydrocarbon group containing one or more double bonds, desirably having from 2 to 10 carbon atoms. A $C_{2-20}$ alkene may optionally include monocyclic, bicyclic, or tricyclic rings, in which each ring desirably has five or six members. The $C_{2-20}$ alkene group may be substituted or unsubstituted.

Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "$C_{2-20}$ alkyne" is meant a branched or unbranched hydrocarbon group containing one or more triple bonds, desirably having from 2 to 10 carbon atoms. A $C_{2-20}$ alkyne may optionally include monocyclic, bicyclic, or tricyclic rings, in which each ring desirably has five or six members. The $C_{2-20}$ alkyne group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "carbonate ester" is meant a linkage group having the formula —C(O)O—C(O)—O—.

By "carboxyalkyl" is meant a chemical moiety with the formula —(R)—COOH, wherein R is an alkyl group.

By "cyclic acetal" is meant a ring structure including two oxygen atoms separated by a carbon atom which is optionally substituted (e.g., 1,3-dioxolane). Exemplary substituents include, without limitation, alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, phosphodiester, phosphoramidate, phosphate, phosphonate, phosphonate ester, sulfonate, sulfate, sulfhydryl, phenol, amidine, guanidine, and imidazole groups.

The term "cyclic system" refers to a compound that contains one or more covalently closed ring structures, in which the atoms forming the backbone of the ring are composed of any combination of the following: carbon, oxygen, nitrogen, sulfur, and phosphorous. The cyclic system may be substituted or unsubstituted. Exemplary substituents include, without limitation, alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "fluoroalkyl" is meant an alkyl group that is substituted with a fluorine.

By "heteroalkyl" is meant a branched or unbranched alkyl group in which one or more methylenes (—$CH_2$—) are replaced by nitrogen, oxygen, sulfur, carbonyl, thiocarbonyl, phosphoryl, or sulfonyl moieties. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "hydroxyalkyl" is meant a chemical moiety with the formula —(R)—OH, wherein R is an alkyl group.

BRIEF DESCRIPTION OF THE DRAWINGS

FIG. 1A to FIG. 1F are a series of images and a graph showing Compound 1 (Dexamethasone-Triethylene Glycol-Dexamethasone, Dex-TEG-Dex) formed into pellets in the glassy state and drug release through surface erosion from an intact pellet.

FIG. 9A to FIG. 9E are a series of images and a graph showing Compound 2 (Hydrocortisone-Triethylene Glycol-Hydrocortisone, HC-TEG-HC) formed into heat-molded pellets, fibers, and extruded cylinders, as well as drug release over time.

FIG. 12A to FIG. 12E are a series of images and a graph showing Compound 5 (Dexamethasone-Hexane-Dexamethasone, Dex-Hex-Dex) formed into heat-molded pellets, fibers, and extruded cylinders, as well as drug release over time.

FIG. 13A to FIG. 13E are a series of images and a graph showing Compound 6 (Hydrocortisone-Succinate-Hydrocortisone, HC-SUCC-HC) formed into heat-molded pellets and fibers, as well as drug release over time.

FIG. 14A to FIG. 14E are an image and a graph showing Compound 7 (Anecortave-Triethylene Glycol-Anecortave, Anec-TEG-Anec) formed into heat molded pellets and drug release over time.

FIG. 15A to FIG. 15C are an image and a graph showing Compound 8 (Dexamethasone-Pentaethylene Glycol-Dexamethasone, Dex-EGS-Dex) formed into heat-molded pellets and drug release over time.

FIG. 18A and FIG. 18B are a series of images showing Compound 11 (Dexamethasone-Heptaethylene Glycol-Dexamethasone, Dex-EG7-Dex) formed into heat-molded pellets.

FIG. 19A and FIG. 19B are a series of images showing Compound 12 (Dexamethasone-Nonaethylene Glycol-Dexamethasone, Dex-EG9-Dex) formed into heat-molded pellets.

FIG. 24A and FIG. 24B are a series of an image and a graph showing a mixture of Compound 1 (Dex-TEG-Dex) and Compound 2 (HC-TEG-HC) formed into heat-molded pellets and drug release.

FIG. 25A and FIG. 25B are a series of an image and a graph showing a mixture of Compound 1 (Dex-TEG-Dex) and Compound 3 (TA-TEG-TA) formed into heat-molded pellets and drug release.

DETAILED DESCRIPTION

Figure 1C:
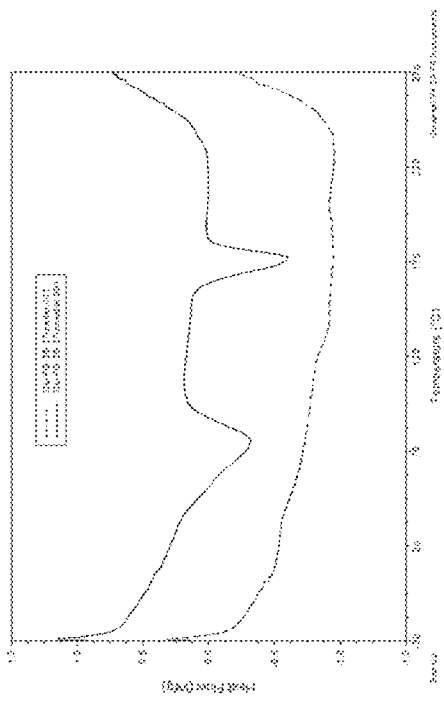

The release of drugs into the eye to treat ocular diseases has until recently been limited to eye drops and injections which lack sustained release profiles. This may be in part due to the unique anatomical and physiological features of the eye that can present challenges to drug delivery; ocular barriers include tear dilution, blood flow, lymphatic clearance and blood-ocular barriers that impede drug transport and lower the efficacy of many drugs [see e.g., Gower et al. Drug discovery in ophthalmology: past success, present challenges, and future opportunities, *BMC Ophthalmology*, 16:11, (Jan. 16, 2016).]. In particular, static barriers (different layers of cornea, sclera, and retina including blood aqueous and bloodretinal barriers), dynamic barriers (choroidal and conjunctival blood flow, lymphatic clearance, and tear dilution), and efflux pumps in conjunction pose a significant challenge for delivery of a drug alone or in a dosage form, especially to the back of the eye, e.g., the posterior segment [AAPS J. 2010 September; 12(3); 348-360].

It is recognized in this disclosure that there is a need for drug delivery platforms that address one or more of these challenges and enable sustained release of ocular therapeutics.

This disclosure features compositions and methods for the treatment of the eye and amelioration of ophthalmic diseases and conditions therewith. Also featured in this disclosure are treatments of the eye including a Schlemm's canal insert or a suprachoroidal insert. The treatment includes insertion of an article formed from therapeutic steroid prodrug dimers that are formed by conjugation of two steroids with a short chain linker. The prodrug dimers disclosed have properties that differ from that of the corresponding stand-alone drugs allowing them to be processed in various forms (e.g. fibers, cylinders, microparticles, etc.) in the glassy state and leading to sustained release of drug in the eye.

This disclosure also features ocular inserts made of steroid drug dimers (e.g., anti-inflammatory steroid drug dimers or antibiotic steroid drug dimers). The ocular inserts can be in a form of fibers or cylinders, e.g., stents or tubes. The ocular inserts can provide a controlled rate of drug release over days, weeks, months, or even years. Alternatively, the ocular inserts can be in the form of cylinders or fibrous meshes (woven or non-woven) implanted intravitreally, subretinally, or suprachoroidally. The ocular insert of the disclosure can minimize inflammation associated with cataract or glaucoma surgery. Further, the Schlemm's canal and suprachoroidal inserts can provide a controlled rate of drug release over days, weeks, months, or even years. In particular embodiments, the Schlemm's canal inserts are inserted into the Schlemm's canal during cataract or glaucoma surgery to facilitate keeping the canal open, and functioning as a scaffold. In particular embodiments the article does not include non-therapeutic materials that could contribute to obstructing the passage of fluids. The Schlemm's canal insert of the disclosure can minimize inflammation of the canal and the surgical insertion point associated with cataract or glaucoma surgery. Alternatively, a suprachoroidal insert is used to reduce intraocular pressure.

Drug Dimers

The disclosure features articles formed from compounds of formula (A-I):

$$D1-L-D2 \quad (A-I)$$

or a pharmaceutically acceptable salt thereof, wherein each of D1 and D2 is, independently, a radical formed from a steroid; and L is a linker covalently linking D1 to D2. Each of D1 and D2 can be, independently, selected from a steroid (e.g., a glucocorticoid steroid, a corticosteroid, an IOP lowering steroid, or fusidic acid). L can be covalently linked to D1 and to D2 via one or more ester, carbonate, carbonate ester, or anhydride linkages. Ester, carbonate, carbonate ester, or anhydride linkages formed from a functional group on D1 and D2 can be selected from, e.g., hydroxyl or carboxy. For example, L can include the radical —C(O)—($R^A$)—C(O)—, —C(O)—OC(O)—($R^A$)—C(O)O—C(O)—, or —O—($R^A$)—O—, where $R^A$ is a radical of a polyol and includes at least one free hydroxyl group or $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —($CH_2CH_2O$)$_q CH_2CH_2$—, —($CH_2CH_2CH_2CH_2O$)$_r CH_2CH_2CH_2CH_2$—, or —($CH_2CH(CH_3)O$)$_s CH_2CH(CH_3)$—, and q, r, and s are integers from 1 to 10 (e.g., 1 to 10, 1 to 5, or 5 to 10). The articles of the disclosure can be machined, molded, emulsion-processed, electrospun, electrosprayed, blow molded, dry spun, heat spun, melt spun, gel spun, or extruded to form a fiber, fiber mesh, woven fabric, non-woven fabric, pellet, cylinder, microparticle (e.g., a microbead), nanoparticle (e.g., a nanobead), tube, stent, or another shaped article sized and shaped for insertion adjacent to, or within, an eye.

The compound can be further described by the formula (A-II):

(A-II), or a pharmaceutically acceptable salt thereof, wherein each of D1-0 and D2-O is, independently, a radical formed from a steroid (e.g., a glucocorticoid steroid, a corticosteroid, an IOP lowering steroid, or fusidic acid).

In some embodiments, each of D1-0 and D2-O is, independently, described by any one of formulas (I-a) to (I-r):

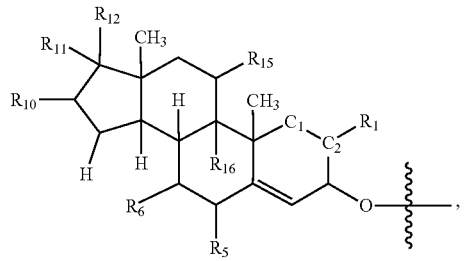
(I-a)

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =$CH_2$; $R_{11}$ represents H, OH, $C_{1-6}$ alkyl, optionally substituted —C(O)$C_{1-6}$ alkyl, —C(O)$CH_2$OC(O)$C_{1-6}$ alkyl, optionally substituted —OC(O)$C_{1-6}$ alkyl, —OC(O)Ph, —OC(O)heterocyclyl, —$CH_2$C(O)$CH_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —$CH_2$C(O)$CH_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; $R_{15}$ represents H, OH, =O, or a halogen atom; and $R_{16}$ represents H or a halogen atom;

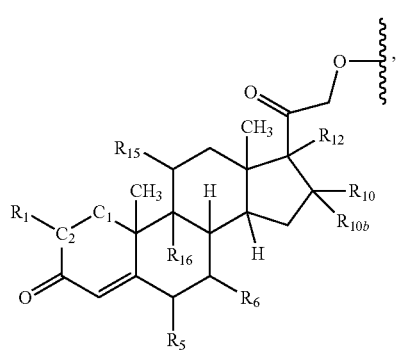
(I-b)

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =$CH_2$; $R_{10b}$ represents H, $C_{1-6}$ alkyl, OH, =$CH_2$, or be absent; $R_{12}$ represents H, OH, optionally substituted —C(O)$C_{1-6}$ alkyl, —C(O)CH$_2$OC(O)$C_{1-6}$ alkyl, optionally substituted —OC(O)$C_{1-6}$ alkyl, or —OC(O)Ph; or $R_{10}$ and $R_{11}$ taken together with carbons to which they are attached form an optionally substituted cyclic acetal or optionally substituted heterocyclyl; $R_{15}$ represents H, OH, =O, or a halogen atom; and $R_{16}$ represents H or a halogen atom;

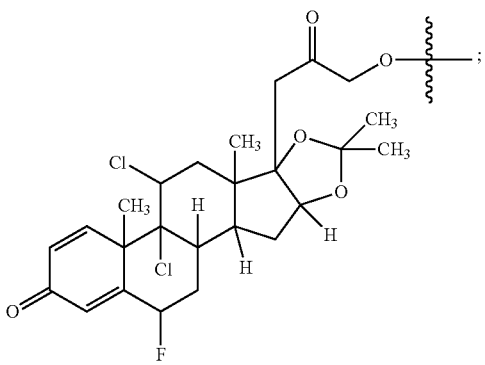
(I-c)

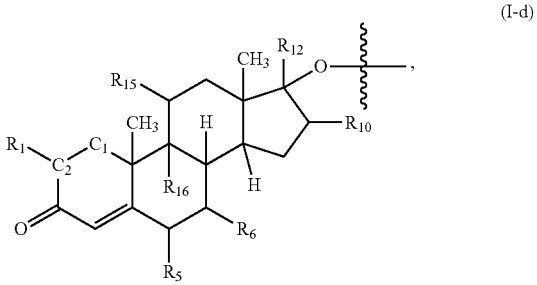
(I-d)

where the bond between $C_1$ and $C_2$ is a single or a double bond; $R_1$ represents H or a halogen atom; $R_5$ represents H, a halogen atom, or $CH_3$; $R_6$ represents H, a halogen atom; $R_{10}$ represents H, OH, $CH_3$, or =$CH_2$; $R_{12}$ represents optionally substituted —C(O)$C_{1-6}$ alkyl, —C(O)CH$_2$OC(O)$C_{1-6}$ alkyl, or —C(O)SCH$_2$F; $R_{15}$ represents OH or =O; and $R_{16}$ represents H or a halogen atom;

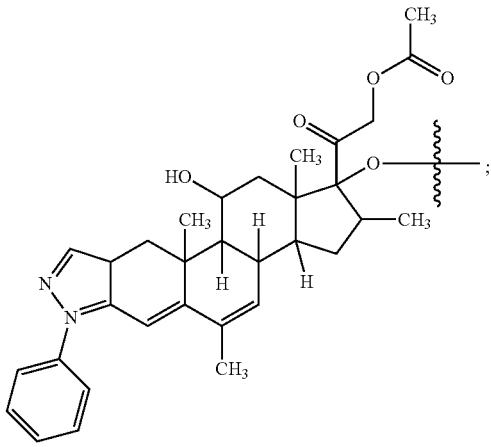
(I-e)

-continued (I-f)

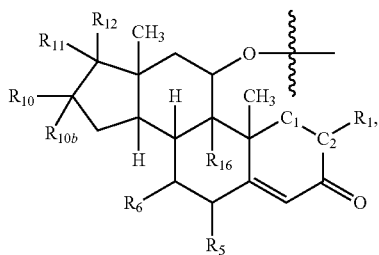

where the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or =CH$_2$; $R_{10b}$ represents H, $C_{1-6}$ alkyl, OH, or =CH$_2$, or is absent; $R_{11}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or $R_{10}$ and $R_{12}$ taken together with carbons to which they are attached form an optionally substituted cyclic acetal or optionally substituted heterocyclyl; and $R_{16}$ represents H or a halogen atom;

(I-g)

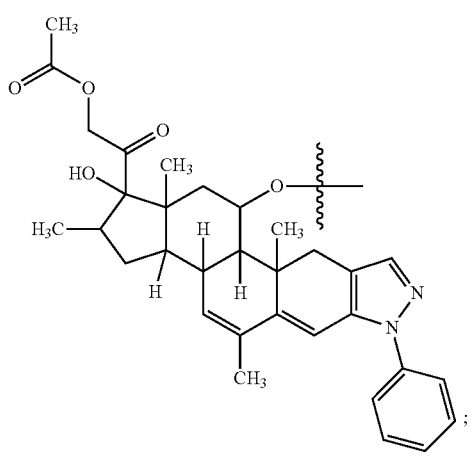

(I-h)

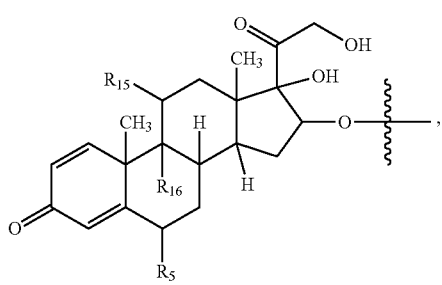

where $R_5$ represents H or a halogen atom; $R_{15}$ represents a halogen atom or OH; and $R_{16}$ represents H or a halogen atom;

(I-i)

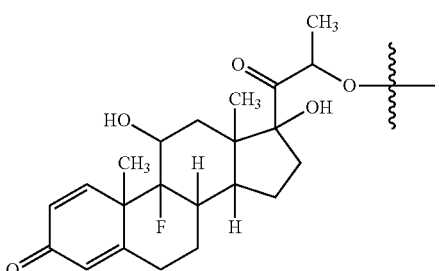

(I-j)

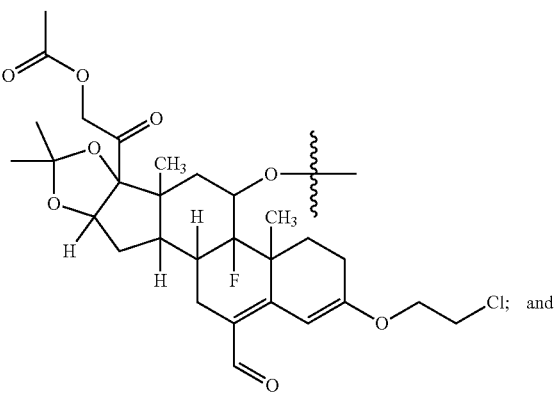

(I-k)

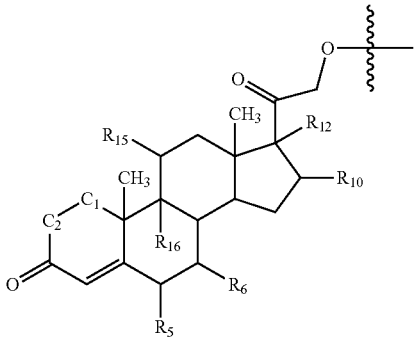

where the bond between $C_1$ and $C_2$ is a double or a single bond; $R_{16}$ represents H or a halogen atom; $R_5$ represents H, CH$_3$, or a halogen atom; $R_{12}$ represents H or a halogen atom; $R_{15}$ represents =O or OH; $R_{12}$ and $R_{10}$ each, independently, represent —H, $C_{1-10}$ alkyl, —OH, —O-acyl, or $R_{12}$ and $R_{10}$ combine to form a cyclic acetal of formula (XVIII-a) where:

(I-m)

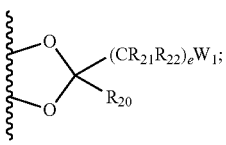

e is an integer from 0 to 6; $R_{20}$, $R_{21}$, and $R_{22}$ each, independently, represent H or $C_{1-10}$ alkyl; and $W_1$ represents H or CH$_3$;

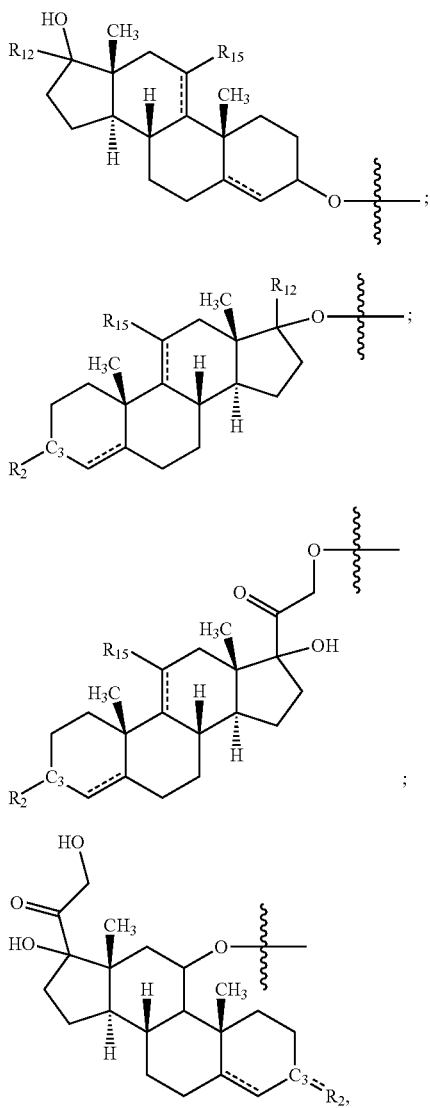

where the bond between $C_3$ and $R_2$ is a single or a double bond; $R^2$ represents OH or =O; $R_{12}$ represents —C(=O)CH$_2$OC(=O)CH$_3$, —C(=O)CH$_2$OH, or —C(=O)CH$_3$; $R_{15}$ represents H or OH.

Drug dimers useful in the methods and compositions of the disclosure include homodimers (e.g., where D1 and D2 are the same) and heterodimers (e.g., where D1 and D2 differ). Glucocorticoids, anti-angiogenic steroids, intraocular pressure (IOP) lowering steroids, and corticosteroids that can be used in the methods and articles of the disclosure include, for example, medrysone, alclometasone, alclometasone dipropionate, amcinonide, beclometasone, beclometasone dipropionate, betamethasone, betamethasone benzoate, betamethasone valerate, budesonide, ciclesonide, clobetasol, clobetasol butyrate, clobetasol propionate, clobetasone, clocortolone, loprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, ulobetasol, anecortave acetate, anecortave, 11-epicortisol, 17α-hydroxyprogesterone, tetrahydrocortexolone, and tetrahydrocortisol.

The disclosure features homodimers of the formula (A-I), or a pharmaceutically acceptable salt thereof, wherein D1 and D2 are radicals formed from the same steroid. L can be covalently linked to D1 and to D2 via one or more ester, carbonate, carbonate ester, or anhydride linkages. Ester, carbonate, carbonate ester, or anhydride linkages formed from a functional group on D1 and D2 can be selected from, e.g., hydroxyl or carboxy. For example, L can include the radical —C(O)—(R$^A$)—C(O)—, —C(O)—OC(O)—(R$^A$)—C(O)O—C(O)—, or —O—(R$^A$)—O—, where R$^A$ is a radical of a polyol and includes at least one free hydroxyl group or R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—, and q, r, and s are integers from 1 to 10 (e.g., 1 to 10, 1 to 5, or 5 to 10). The homodimer can be further described by one of formulas (II-a) to (II-r), below.

In particular embodiments, the steroid is a glucocorticoid steroid and the drug dimer is further described by the formula (II):

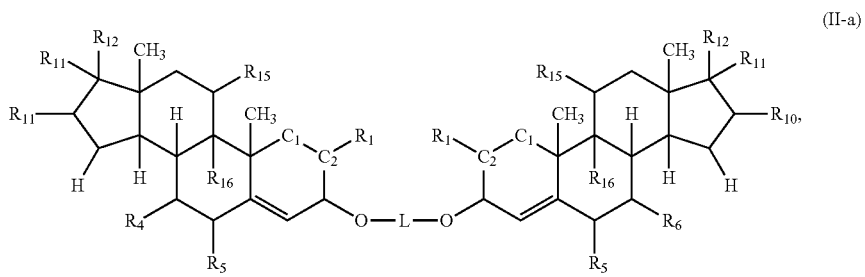

wherein the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or $=CH_2$; $R_{11}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)O$C_{1-6}$ alkyl, —C(O)SCH$_2$F, or —OC(O)O$C_{1-6}$ alkyl; or $R_{10}$ and $R_{11}$ taken together with carbons to which they are attached form an optionally substituted cyclic acetal or optionally substituted heterocyclyl; $R_{12}$ represents H, OH, $C_{1-6}$ alkyl, optionally substituted —C(O)$C_{1-6}$ alkyl, —C(O)CH$_2$OC(O)$C_{1-6}$ alkyl, optionally substituted —OC(O)$C_{1-6}$ alkyl, —OC(O)Ph, —OC(O)heterocyclyl, —CH$_2$C(O)CH$_2$OH, —C(O)C(O)OH, —C(O)C(O)O$C_{1-6}$ alkyl, —C(O)SCH$_2$F, or —OC(O)O$C_{1-6}$ alkyl; or $R_{10}$ and $R_{12}$ taken together with carbons to which they are attached form an optionally substituted cyclic acetal or optionally substituted heterocyclyl; $R_{15}$ represents H, OH, =O, or a halogen atom; $R_{16}$ represents H or a halogen atom; L is —C(O)O—(R$^A$)—OC(O)—, —C(O)—OC(O)—(R$^A$)—C(O)O—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-a) can be formed from a glucocorticoid steroid selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cortisol, cortisone, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol.

In some embodiments, the steroid is a glucocorticoid steroid and the drug dimer is further described by the formula (II-b):

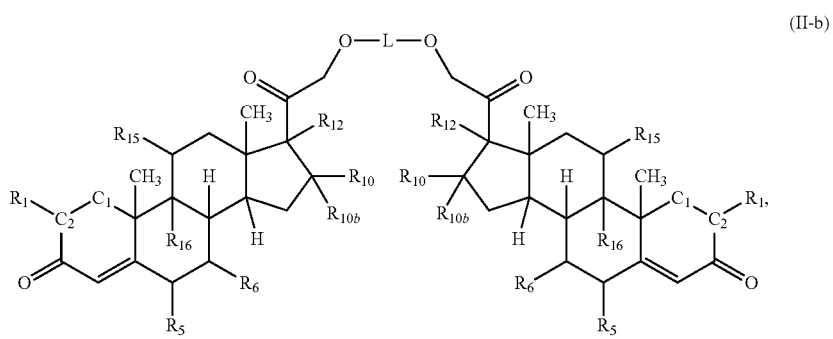

(II-b)

wherein the bond between $C_1$ and $C_2$ is a single or a double bond; $R_1$ represents H or a halogen atom; $R_5$ represents H, $C_{1-6}$ alkyl, or a halogen atom; $R_6$ represents H or a halogen atom; $R_{10}$ represents H, $C_{1-6}$ alkyl, OH, or $=CH_2$; $R_{10b}$ represents H, $C_{1-6}$ alkyl, OH, $=CH_2$, or be absent; $R_{12}$ represents H, OH, optionally substituted —C(O)$C_{1-6}$ alkyl, —C(O)CH$_2$OC(O)$C_{1-6}$alkyl, optionally substituted —OC(O)$C_{1-6}$ alkyl, or —OC(O)Ph; or $R_{10}$ and $R_{11}$ taken together with carbons to which they are attached form an optionally substituted cyclic acetal or optionally substituted heterocyclyl; $R_{15}$ represents H, OH, =O, or a halogen atom; $R_{16}$ represents H or a halogen atom; L is —C(O)O—(R$^A$)—OC(O)—, —C(O)—OC(O)—(R$^A$)—C(O)O—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-b) can be formed from a glucocorticoid steroid selected from the group consisting of alclometasone, beclometasone, betamethasone, betamethasone benzoate, betamethasone valerate, budesonide, cortisol, cortisone, desonide, desoximetasone, desoxycortone, desoxymethasone, dexamethasone, diflorasone, diflucortolone, difluorocortolone, fluclorolone, fluclorolone acetonide, fludroxycortide, flumetasone, flumethasone, flunisolide, flunisolide, fluocinolone, fluocinolone acetonide, fluocortolone, fluorocortisone, fluprednidene, fluprednisolone, halometasone, hydrocortisone, hydrocortisone butyrate, meprednisone, 6a-methylprednisolone, methylprednisolone, paramethasone, prednisolone, prednisone, prednylidene, triamcinolone, and triamcinolone acetonide.

In particular embodiments, the steroid is a glucocorticoid steroid and the drug dimer is further described by the formula (II-c):

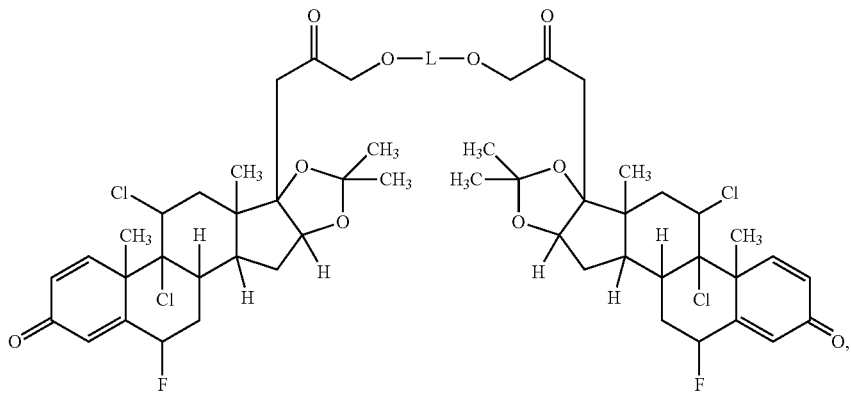

wherein L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; and n, m, and p are integers from 1 to 10. The drug dimer of formula (II-c) can be formed from the glucocorticoid steroid fluclorolone acetonide.

In some embodiments, the steroid is a glucocorticoid steroid and the drug dimer is further described by the formula (II-d):

$C_{1-6}$ alkyl, or —C(O)$SCH_2F$; $R_{15}$ represents OH or =O; $R_{16}$ represents H or a halogen atom; L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; and n, m, and p are integers from 1 to 10. The drug dimer of formula (II-d) can be formed from a glucocorticoid steroid selected from the group consisting of alclometasone, beclometasone, betamethasone, clobetasol, clobetasone, cortisol, cortisone, dexamethasone, diflorasone, fluclorolone, flumetasone, flumethasone, flumethasone pivalate, fluocinolone, fluorocortisone, fluorometholone, fluperolone, fluprednidene, fluprednidene

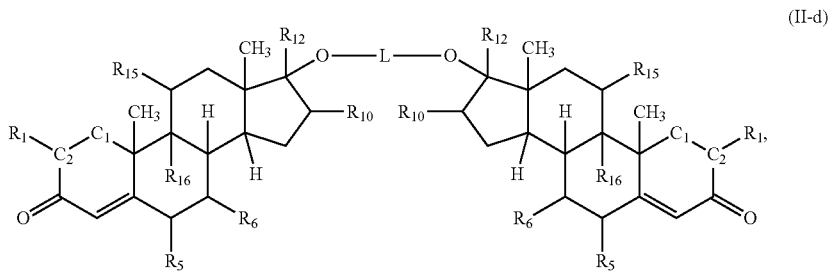

wherein the bond between $C_1$ and $C_2$ is a single or a double bond; $R_1$ represents H or a halogen atom; $R_5$ represents H, a halogen atom, or $CH_3$; $R_6$ represents H, a halogen atom; $R_{10}$ represents H, OH, $CH_3$, or =$CH_2$; $R_{12}$ represents optionally substituted —C(O)$C_{1-6}$ alkyl, —C(O)$CH_2$OC(O)

acetate, fluprednisolone, fluticasone, halometasone, hydrocortisone, hydrocortisone acetate, hydrocortisone butyrate, meprednisone, 6a-methylprednisolone, methylprednisolone, methylprednisolone acetate, mometasone, paramethasone, prednisolone, prednisone, prednylidene, tixocortol, triamcinolone, and ulobetasol.

In particular embodiments, the steroid is a glucocorticoid steroid and the drug dimer is further described by the formula (II-e):

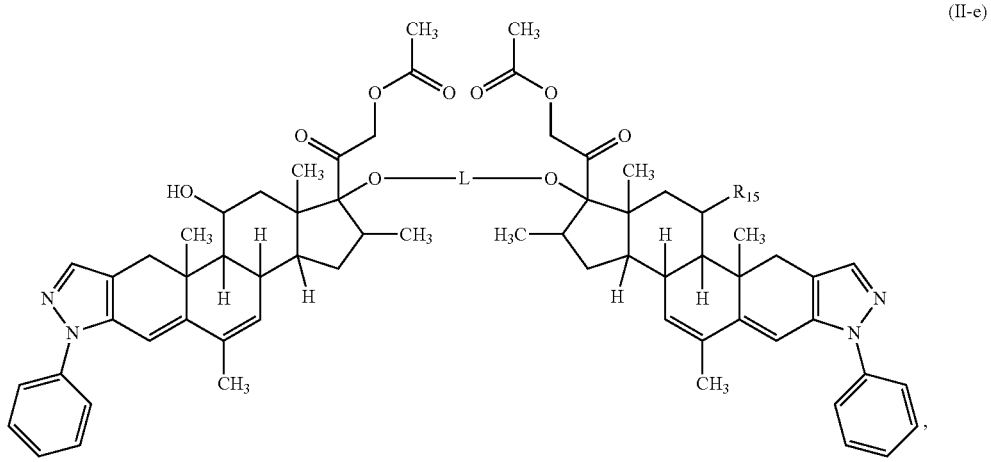

wherein L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-e) can be formed from the glucocorticoid steroid cortivazol.

In some embodiments, the steroid is a glucocorticoid steroid and the drug dimer is further described by the formula (II-f):

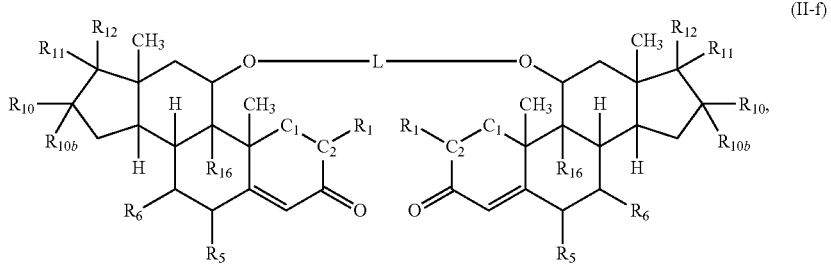

wherein the bond between C$_1$ and C$_2$ is a single or a double bond; R$_1$ represents H or a halogen atom; R$_5$ represents H, C$_{1-6}$ alkyl, or a halogen atom; R$_6$ represents H or a halogen atom; R$_{10}$ represents H, C$_{1-6}$ alkyl, OH, or =CH$_2$; R$_{10b}$ represents H, C$_{1-6}$ alkyl, OH, or =CH$_2$, or is absent; R$_{11}$ represents H, OH, C$_{1-6}$ alkyl, optionally substituted —C(O)C$_{1-6}$ alkyl, —C(O)CH$_2$OC(O)C$_{1-6}$ alkyl, optionally substituted —OC(O)C$_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or R$_{10}$ and R$_{12}$ taken together with carbons to which they are attached form an optionally substituted cyclic acetal or optionally substituted heterocyclyl; R$_{12}$ represents H, OH, C$_{1-6}$ alkyl, optionally substituted —C(O)C$_{1-6}$ alkyl, —C(O)CH$_2$OC(O)C$_{1-6}$ alkyl, optionally substituted —OC(O)C$_{1-6}$ alkyl, —OC(O)Ph, —OC(O)heterocyclyl, —CH$_2$C(O)CH$_2$OH, —C(O)C(O)OH, —C(O)C(O)OC$_{1-6}$ alkyl, —C(O)SCH$_2$F, or —OC(O)OC$_{1-6}$ alkyl; or R$_{10}$ and R$_{12}$ taken together with carbons to which they are attached form an optionally substituted cyclic acetal or optionally substituted heterocyclyl; R$_{16}$ represents H or a halogen atom; L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-f) can be formed from a glucocorticoid steroid selected from the group consisting of medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cortisol, cortisone, cortivazol, deflazacort, desonide, desoximetasone, desoxymethasone, dexamethasone, diflorasone, diflorasone diacetate, diflucortolone, diflucortolone valerate, difluorocortolone, difluprednate, fludroxycortide, flumetasone, flumethasone, flumethasone pivalate, flunisolide, flunisolide, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide, and ulobetasol.

In particular embodiments, the steroid is a glucocorticoid steroid and the drug dimer is further described by the formula (II-g):

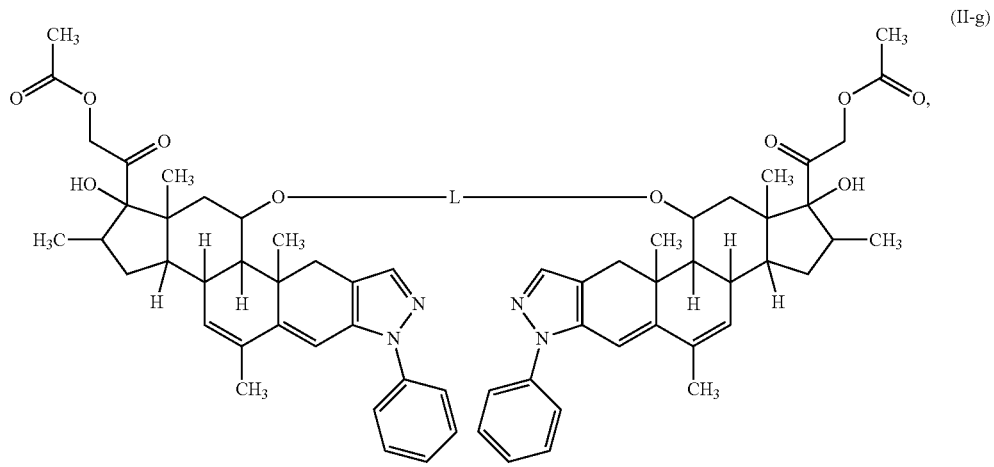

Wherein L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-g) can be formed from the glucocorticoid steroid cortivazol.

In some embodiments, the steroid is a glucocorticoid steroid and the drug dimer is further described by the formula (II-h):

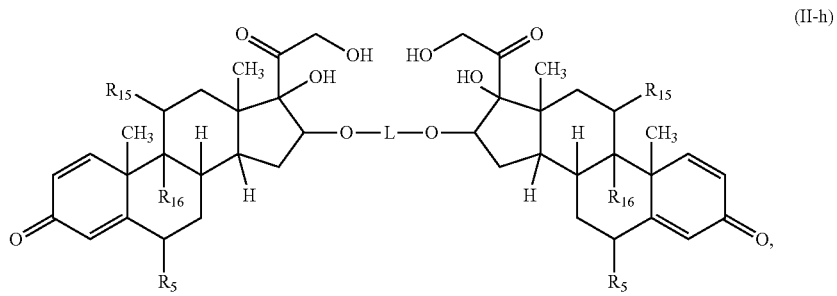

wherein $R_5$ represents H or a halogen atom; $R_{15}$ represents a halogen atom or OH; $R_{16}$ represents H or a halogen atom; L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_n$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; and n, m, and p are integers from 1 to 10. The drug dimer of formula (II-h) can be formed from a glucocorticoid steroid selected from the group consisting of fluclorolone, fluocinolone, and triamcinolone.

In particular embodiments, the steroid is a glucocorticoid steroid and the drug dimer is further described by the formula

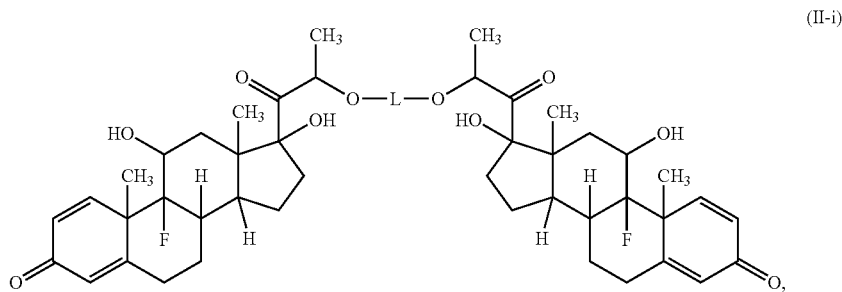

(II-i)

wherein L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O$)$_m$$CH_2CH_2O$—, —O($CH_2CH_2CH_2CH_2O$)$_m$$CH_2CH_2CH_2CH_2O$—, or —O($CH_2CH(CH_3)O$)$_p$$CH_2CH(CH_3)O$—; and n, m, and p are integers from 1 to 10. The drug dimer of formula can be formed from fluperolone.

In some embodiments, the steroid is a glucocorticoid steroid and the drug dimer is further described by the formula (II-j):

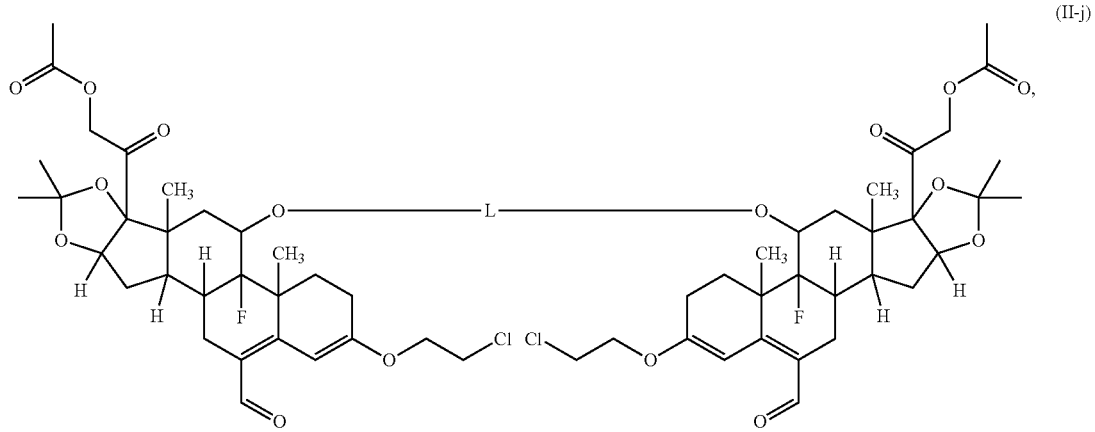

(II-j)

wherein L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; and n, m, and p are integers from 1 to 10. The drug dimer of formula (II j) can be formed from formocortal.

In particular embodiments, the steroid is a corticosteroid and the drug dimer is further described by the formula (II-k):

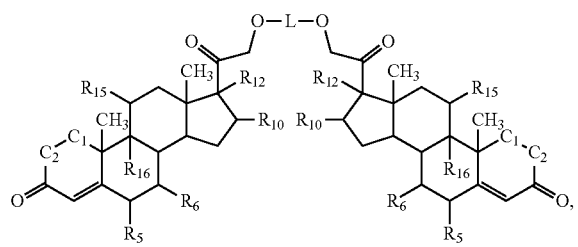

(II-k)

wherein the bond between $C_1$ and $C_2$ is a double or a single bond; $R_{16}$ represents H or a halogen atom; $R_5$ represents H, $CH_3$, or a halogen atom; $R_{12}$ represents H or a halogen atom; $R_{15}$ represents =O or OH; $R_{12}$ and $R_{10}$ each, independently, represent —H, $C_{1-10}$ alkyl, —OH, —O-acyl, or $R_{12}$ and $R_{10}$ combine to form a cyclic acetal of formula (II-ka) wherein:

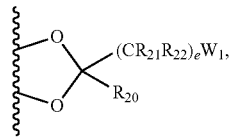

(II-ka)

e is an integer from 0 to 6; $R_{20}$, $R_{21}$, and $R_{22}$ each, independently, represent H or $C_{1-10}$ alkyl; $W_1$ represents H or $CH_3$; L is —C(O)O—($R^A$)—OC(O)—, —C(O)—OC(O)—($R^A$)—C(O)O—C(O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O($CH_2CH_2O)_nCH_2CH_2O$—, —O($CH_2CH_2CH_2CH_2O)_mCH_2CH_2CH_2CH_2O$—, or —O($CH_2CH(CH_3)O)_pCH_2CH(CH_3)O$—; and n, m, and p are integers from 1 to 10. The drug dimer of formula (II-k) can be formed from a corticosteroid selected from the group consisting of alclometasone, beclomethasone, betamethasone, betamethasone valerate, budesonide, chloroprednisone, cloprednol, corticosterone, cortisone, desonide, desoximerasone, dexamethasone, diflorasone, diflucortolone, enoxolone, flucloronide, flumethasone, flunisolide, fluocinolone acetonide, fluocortolone, fluprednisolone, flurandrenolide, halometasone, hydrocortisone, hydrocortisone butyrate, meprednisone, methylprednicolone, paramethasone, prednisolone, prednisone, prednival, prednylidene, triamcinolone, and triamcinolone acetonide.

In any of the above formulas (II-a)-(II-k), O—($R^A$)—O can be a radical of a polyol formed from a cyclitol, and sugar alcohol, or glycerin; or O—($R^A$)—O can be a radical formed from an alkane diol (e.g., a $C_{1-10}$ alkane diol), diethylene glycol, triethylene glycol, tetraethylene glycol, or pentaethylene glycol.

In particular embodiments, the steroid is an antibiotic steroid and the drug dimer is further described by the formula (II-m):

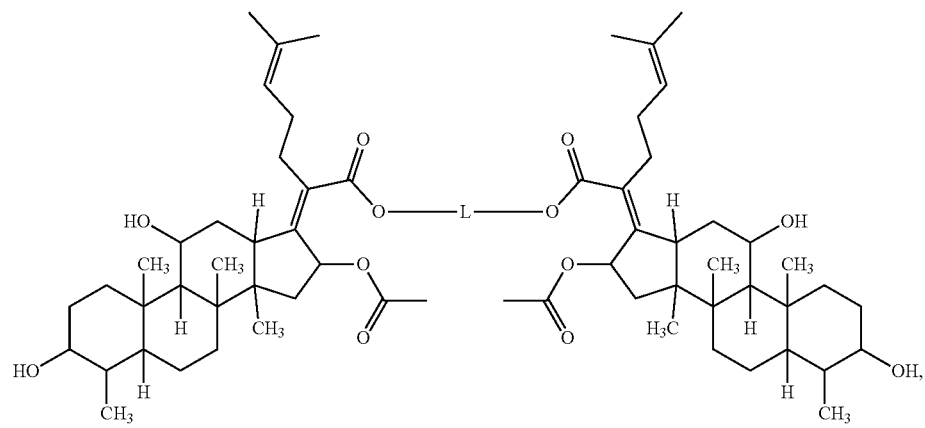

(II-m)

wherein L is —C(O)—(R$^A$)—C(O)—, —(R$^A$)—, or —C(O)—O—(R$^A$)—O—C(O)— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms; or L is —O—(R$^A$)—O— and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, and —O(CH$_2$CH(CH$_3$)O)$_p$CH$_2$CH(CH$_3$)O—; and n, m, and p are integers from 1 to 10. The drug dimer of formula (II-m) can be formed from fusidic acid.

In particular embodiments, the steroid is an anti-angiogenic steroid or an intraocular pressure (TOP) lowering steroid, and the drug dimer is further described by the formula (II-n):

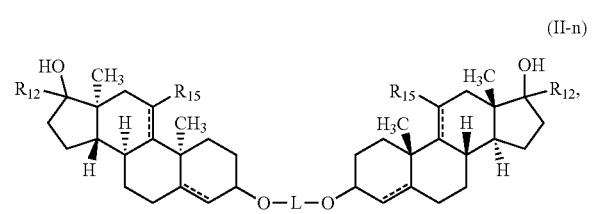

(II-n)

wherein R$_{12}$ represents —C(=O)CH$_2$OC(=O)CH$_3$, —C(=O)CH$_2$OH, or —C(=O)CH$_3$; R$_{15}$ represents H or OH; and L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-n) can be formed from anecortave acetate, anecortave, 11-epicortisol, 17α-hydroxyprogesterone, tetrahydrocortexolone, or tetrahydrocortisol.

In particular embodiments, the steroid is an anti-angiogenic steroid or an intraocular pressure (TOP) lowering steroid, and the drug dimer is further described by the formula (II-o):

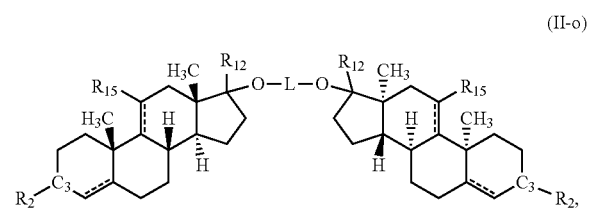

(II-o)

wherein the bond between C$_3$ and R$_2$ is a single or a double bond; R$_2$ represents OH or =O; R$_{12}$ represents —C(=O)CH$_2$OC(=O)CH$_3$, —C(=O)CH$_2$OH, or —C(=O)CH$_3$, R$_{15}$ represents H or OH; and L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-o) can be formed from anecortave acetate, anecortave, 11-epicortisol, 17α-hydroxyprogesterone, tetrahydrocortexolone, or tetrahydrocortisol.

In particular embodiments, the steroid is an anti-angiogenic steroid or an intraocular pressure (TOP) lowering steroid, and the drug dimer is further described by the formula (II-p):

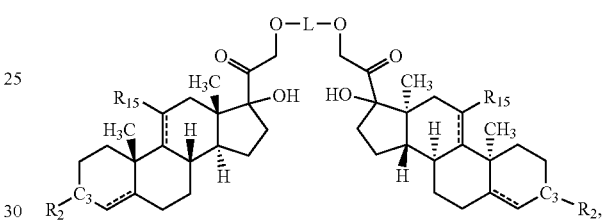

(II-p)

wherein the bond between C$_3$ and R$_2$ is a single or a double bond; R$_2$ represents OH or =O; R$_{15}$ represents H or OH; and L is —C(O)O—(R$^A$)—OC(O)—, —C(O)—OC(O)—(R$^A$)—C(O)O—C(O)—; R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-p) can be formed from anecortave, 11-epicortisol, tetrahydrocortexolone, or tetrahydrocortisol.

In particular embodiments, the steroid is an anti-angiogenic steroid or an intraocular pressure (TOP) lowering steroid, and the drug dimer is further described by the formula (II-r):

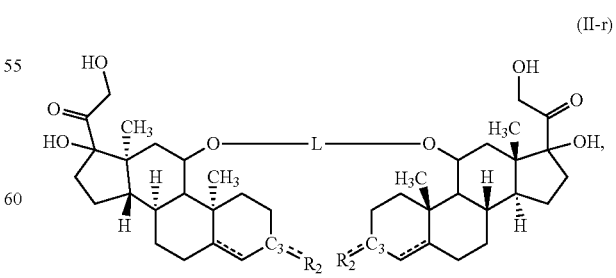

(II-r)

wherein the bond between C$_3$ and R$_2$ is a single or a double bond; R$_2$ represents OH or =O; and L is —C(O)O—(R$^A$)—OC(O)—, —C(O)—OC(O)—(R$^A$)—C(O)O—C (O)—; $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^A$)—O is a radical of a polyol and includes at least one free hydroxyl group or O—($R^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10. The drug dimer of formula (II-r) can be formed from 11-epicortisol or tetrahydrocortisol.

Shaped Articles

The pharmaceutical compositions of the disclosure can include an article in the form of fibers, fiber meshes, woven fabrics, non-woven fabrics, pellets, cylinders, microparticles (e.g., microbeads), nanoparticles (e.g., nanobeads), or other shaped articles, such as stents/tubes suitable for ophthalmology including contact lenses, sutures, microshunt devices, optical rings, punctal plugs, and ocular inserts. Additionally, the pharmaceutical compositions of the disclosure can include an article in the form of fibers, cylinders, or other shaped articles, such as stents/tubes sized for insertion into the Schlemm's canal of an eye. Alternatively, the pharmaceutical compositions of the disclosure can include an article in the form of pellets or cylinders sized for insertion into the suprachoroidal space of an eye. The articles can achieve desired drug loading and long term release profile relative to the corresponding stand-alone glucocorticoid or corticosteroid drug therapy. Alternatively, the articles of the disclosure may be injected intraocularly (e.g., for the treatment of inflammation occurring at the back of the eye).

Processing Methods

Articles of the disclosure can be formed using any number of the methods, for example, heat processing or solvent processing of the drug dimer of formula (I). Heat processing can include heat molding, injection molding, extrusion, 3D printing, melt electrospinning, fiber spinning, fiber extrusion, and/or blow molding. Solvent processing may include coating, micro printing, emulsion processing, dot printing, micropatterning, fiber spinning, solvent blow molding, electrospraying, and electrospinning.

Electrospraying Method

In some embodiments, the pharmaceutical compositions of the disclosure are dissolved in a solvent (e.g., acetone) at concentrations ranging from, e.g., 10-30% w/v, and are electrosprayed to form micro- and nanobeads. The solutions can be loaded into a syringe and can be injected at a particular rate, e.g., 0.5 mL/h, onto a stationary collection plate. Between the needle and collecting surface, a potential difference of, e.g., 18 kV, can be maintained. Exemplary concentration of 10% w/v is used to obtain nanoparticles. In other embodiments, a concentration of 30% w/v is used to obtain microbeads.

Fiber Spinning Methods

In some embodiments, the pharmaceutical compositions of the disclosure, e.g., fibers or fibrous meshes with aligned and unaligned morphologies are prepared by electrospinning. The pharmaceutical compositions of the disclosure are dissolved in a solvent (e.g., THF, or 1:1 ratio of DCM/THF). The solutions may be injected from a syringe at a particular rate, e.g., 0.5 mL/h, onto a cylindrical mandrel rotating at a particular rotational speed, e.g., 1150 rpm, to obtain aligned fibers, or onto a stationary collector surface to obtain unaligned fibers. A potential difference (e.g., 18 kV or 17 kV) can be maintained between the needle and collecting surface for aligned and random fibers.

In other embodiments, fibers are prepared either from the melt at elevated temperatures, the glassy state intermediate, or from solution by dissolving the pharmaceutical compositions of the disclosure in a solvent (e.g., DCM, THF, or chloroform). As used herein, melt spinning describes heat processing from the melt state, heat spinning describes heat processing from the glassy state, and wet, dry, and gel spinning describe solution processing.

The viscous melt, intermediate, or solution can be fed through a spinneret and fibers may be formed upon cooling (melt or heat spinning) or following solvent evaporation with warm air as the compound exits the spinneret (dry spinning). Wet spinning and gel spinning, performed according to methods known in the art, may also be used to produce the fibers of the disclosure. Heat spinning describes a process that is essentially the same as the melt spinning process, but performed with the glassy state intermediate and heated above the glass transition temperature (Tg) to get the viscous fluid to extrude/spin instead of the melt. Alternatively, tweezers may be dipped into melted material or concentrated solutions and retracted slowly in order to pull fibers. The rate of pulling and distance pulled may be varied to yield fibers and columnar structures of different thickness.

Emulsion Method

In some embodiments, microparticles or nanoparticles made from the pharmaceutical composition can be formed using an emulsion process. The pharmaceutical composition may be dissolved in an organic solvent (e.g., DCM, THF, etc.) and a surfactant (e.g., SDS, PVA, etc.) may be added to the solution/mixture at a low percentage (e.g., 1%). The resulting mixture may be stirred for the appropriate time at room temperature to form an emulsion. The emulsion may be subsequently added to Milli-Q water under stirring for an appropriate time (e.g., 1 h) to remove residual solvent. The resulting micro- or nanoparticles may be collected by centrifugation and dried to obtain the desired form.

Extrusion Method

In some embodiments, injectable cylinders made from the pharmaceutical composition may be formed by heat extrusion. The pharmaceutical composition may be loaded into a hot melt extruder, heated to a temperature above the melting point (for crystalline compositions) or glass transition temperature (for pre-melted or amorphous compositions), and extruded using a light compressive force to push the material through the nozzle and a light tensile force to pull the material out of the extruder. The extrudate may be cut to the desired length for appropriate drug dosing for the indication of interest.

Bead Sizing and Milling

In some embodiments, a milling process may be used to reduce the size of an article of the disclosure to form sized particles, e.g., beads, in the micrometer (microbeads) to nanometer size range (nanobeads). The milling process may be performed using a mill or other suitable apparatus. Dry and wet milling processes such as jet milling, cryo-milling, ball milling, media milling, sonication, and homogenization are known and can be used in methods described herein. Generally, in a wet milling process, a suspension of the material to be used as the core is agitated with or without excipients to reduce particle size. Dry milling is a process wherein the material to be used as the article core is mixed with milling media with or without excipients to reduce particle size. In a cyro-milling process, a suspension of the material to be used as the core is mixed with milling media with or without excipients under cooled temperatures. In some embodiments, subsequent heating of the milled microparticle above the Tg is needed to achieve a spherical shape, or particles with non-spherical shapes can be used as milled.

Low Temperature Processing Using Intermediate Glassy State Articles

In certain embodiments, the prodrug dimer has a limited window (e.g., short timeframe of seconds to minutes) of thermal stability, whereby the purity of the dimer is minimally affected at elevated temperatures. In some embodiments, it is beneficial to make an intermediate glassy state form (e.g., film, pellet, micro-particles, or other shaped article). This can be accomplished by heat or solvent processing to remove or reduce the crystallinity of the material to form a glassy state composition. The glassy state composition is subsequently heat processed at a lower temperature (e.g., processing just above the glass transition temperature (Tg), and below the melt temperature (Tm)). This can provide a longer timeframe for heat processing the glassy state material into the final shaped article, while reducing the impact of processing conditions on the purity of the prodrug dimer in the article. The process can include shaping the article by extrusion, or any other process described herein.

Formulations

The formulations of the disclosure provide optimal delivery of a drug as they release the drug from an article of the disclosure in a controlled manner, for example, by surface erosion. The surface erosion mechanism of drug release may allow the shaped article to maintain its physical form (shape), while gradually decreasing in size as the surface erodes (e.g., like a bar of soap), rather than bulk erosion that is characteristic of some polymer-based drug release vehicles (e.g., polylactic/glycolic acid). This can inhibit burst release and reduce the formation of inflammatory particulates (e.g., no crystalline particulates are formed when drug is released in the manner described herein). The drug can be controlled to be delivered over a desired period of time to a desired site of the eye. A slower and steadier rate of delivery (e.g., release of less than 10% of D1 or D2 (as a percentage of the total drug, D1 or D2, present in the fiber in prodrug form) at 37° C. in 100% bovine serum over 5 days) can in turn result in a reduction in the frequency with which the pharmaceutical composition must be administered to a subject, and improve the safety profile of the drug and improving patient compliance with dosing regimens. Drug release can also be tailored to avoid side effects of slower and longer release of the drug by engineering the article to provide steady release over a comparatively shorter period of time. Depending on the indication and the drug, the drug release can be tailored for dose and duration appropriate to the indication of interest.

The rate of release of a drug can depend on many factors, for example, the drug composition of the drug dimer. Drug release rate from the drug dimer can be modulated by the cleavage of drug-linker bond through hydrolysis or enzymatic degradation. Therefore, the selection of linking moiety can affect drug release rate. Further, the drug release rate can be controlled by the selection of the functional group on the drug to conjugate through to the linker, for example, a primary vs. a secondary steroid hydroxyl group. The rate of release of a given drug from a drug dimer can also depend on the quantity of the loaded drug dimer as a percent of the final drug dimer formulation, e.g., by using an appropriate pharmaceutical excipient (e.g., bulking agent/excipient). Another factor that can affect the release rate of a drug from the article is size or surface area. In some embodiments, drug release is tailored based on the solubility of drug dimer (e.g., through selection of appropriate drug and/or linker) that will influence the rate of surface erosion (e.g., dissolution/degradation) from the article. In other embodiments, drug release is affected by changes in surface area of the formulation, e.g., by changing the diameter of the articles. By adjusting the vide supra factors, dissolution, degradation, diffusion, and controlled release may be varied over wide ranges. For example, release can be designed to be initiated over minutes to hours, and may extend over the course of days, weeks, months, or years.

In some embodiments, the drug dimers of the disclosure are used as a drug delivery device (or, e.g., a drug depot) with a minimal need for additives. This can achieve a local, sustained release and a local biological effect, while minimizing a systemic response. In some embodiments, when present, the additives are in small amounts and do not affect the physical or bulk properties. In some embodiments, when present, the additives do not alter the drug release properties from the pharmaceutical composition but rather act to improve processing of the prodrug dimer into the shaped article. In some embodiments, the pharmaceutical compositions contain additives such as a plasticizer (e.g., to reduce thermal transition temperatures), an antioxidant (e.g., to increase stability during heat processing), a binder (e.g., to add flexibility to the fibers), a bulking agent (e.g., to reduce total drug content), a lubricant, dyes, or mixtures thereof. The additives may be present at 30% (w/w), e.g., 20% (w/w), 10% (w/w), 7% (w/w), 5% (w/w), 3% (w/w), 1% (w/w), 0.5% (w/w), or 0.1% (w/w). Examples of plasticizers are polyols, e.g., glycerol, ethylene glycol, diethylene glycol, triethylene glycol, tetraethylene glycol, polyethylene glycol, propylene glycol, triacetin, sorbitol, mannitol, xylitol, fatty acids, monosaccharides (e.g., glucose, mannose, fructose, sucrose), ethanolamine, urea, triethanolamine, vegetable oils, lecithin, or waxes. Exemplary antioxidants are glutathione, ascorbic acid, cysteine, or tocopherol. The binders and bulking agents can be, e.g., polyvvinylpyrrolidone (PVP), starch paste, pregelatinized starch, hydroxypropyl methyl cellulose (HPMC), carboxymethyl cellulose (CMC), or polyethylene glycol (PEG) 6000.

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, articles of the disclosure may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Treatment

In one embodiment, there is provided a method of treating a subject for an ocular disease or condition including administering to the subject a compound, article, or ocular insert described herein. Also provided is a method of treating a subject for an ocular disease or condition including inserting into the Schlemm's canal or suprachoroidal space in the eye of a subject a compound, article, or Schlemm's canal or suprachoroidal insert described herein. In one embodiment, the "subject" can be any animal, while in certain embodiments, the "subject" is a mammal and, in a preferred embodiment, a human.

Diseases and conditions that can be treated using compounds, compositions and dosage forms as described herein include, but are not limited to, disorders of the eyelid, lacrimal system and orbit; inflammatory disorders of the conjunctiva; disorders of the sclera, iris and ciliary body; disorders of the lens; disorders of the choroid and retina, including disorders and conditions associated with chorioretinal inflammation or infection; disorders of the vitreous body and globe; disorders of the optic nerve and visual pathways; and disorders of the ocular muscles.

An anterior ocular inflammatory disease or condition, or an infection, primarily affects or involves an anterior ocular region or site (i.e. front of the eye), such as a periocular muscle, an eye lid or an eye ball tissue or fluid which is located anterior to the posterior wall of the lens capsule or ciliary muscles. A posterior ocular disease or condition primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. As discussed in the Background, drug delivery to the posterior segment presents particular challenges and, in one embodiment, compounds, compositions and dosage forms as described herein may be used to treat a posterior ocular disease or condition by placement of an article of the disclosure adjacent to or within a structure of the eye.

The articles of the disclosure may be used to treat, prevent, or manage inflammation or infection in the eye of a subject. For example, the ocular condition to be treated may be at the front of the eye. A front of the eye ocular condition includes a disease, ailment or condition, such as for example, post-surgical inflammation; uveitis; infections; aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; corneal neovascularization; refractive disorders and strabismus. In some embodiments, articles of the disclosure may be used to treat, prevent, or manage an ocular condition at the back of the eye of a subject. A posterior ocular condition can include a disease, ailment, or condition, such as intraocular melanoma; acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema (e.g., cystoid macular edema (CME), diabetic macular edema (DME), and macular edema from retinal vein occlusion); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. In some embodiments, the articles of the disclosure may be used to treat, prevent, or manage dry eye in a subject.

In some embodiments, the articles of the disclosure may be used to treat, prevent, or manage inflammation in the eye of a subject (e.g., where the drug dimer is formed from one or more corticosteroids). Inflammation is associated with a variety of ocular disorders. Inflammation may also result from a number of ophthalmic surgical procedures, including cataract surgery and glaucoma surgery. In some embodiments, the pharmaceutical agent that is delivered into the eye by the articles of the disclosure and/or methods described herein may be a corticosteroid.

In certain embodiments, the pharmaceutical agent includes one or more of hydrocortisone, cortisone, tixocortol, prednisolone, methylprednisolone, prednisone, triamcinolone acetonide, mometasone, amcinonide, budesonide, desonide, fluocinonide, fluocinolone, halcinonide, betamethasone, dexamethasone, fluocortolone, hydrocortisone, aclometasone, prednicarbate, clobetasone, clobetasol, fluprednidene, glucocorticoid, mineralocorticoid, aldosterone, deoxycorticosterone, fludrocortisone, halobetasol, diflorasone, desoximetasone, fluticasone, flurandrenolide, alclometasone, diflucortolone, flunisolide, and beclomethasone. In some embodiments, the drug dimer of the disclosure are used as adjunctive therapy to reduce inflammation and fibrosis associated with devices (e.g., minimally invasive glaucoma surgery (MIGS) devices). In some embodiments, articles of the disclosure may be used to treat, prevent, or manage age-related macular degeneration (AMD) in a subject.

In some embodiments, the articles of the disclosure may be used to treat, prevent, or manage infection in the eye of a subject (e.g., where the drug dimer is formed from an antibiotic steroid). In some embodiments, the pharmaceutical agent that is delivered into the eye by the articles of the disclosure and/or methods described herein may be fusidic acid.

Ocular Inserts

In some embodiments, the ocular inserts are shaped as fibers, rods, tubes, or stents. In some embodiments, the fibers have diameters in the range of 0.01-0.15 mm, e.g., 0.01-0.10 mm, 0.04-0.09 mm, 0.05-0.08 mm, or 0.05-0.15 mm. In some embodiments, the fibers have lengths sized for placement within the ocular space. In some embodiments, the ocular inserts are smaller than the canal diameter which ranges between 120 and 350 µm.

The ocular inserts may have a blunt tip with a rounded shape. For example, the blunt tip may have a hemispherical shape.

Some ocular inserts, such as tubes or stents, may include an inlet portion that is shaped and sized to extend through the trabecular meshwork of the eye. In some embodiments, the ocular insert is a hollow tube and can facilitate the flow of aqueous humor through its structure.

Schlemm's Canal Inserts

Schlemm's canal is located approximately in the apex of the angle of the junction of the cornea and the sclera and runs parallel to the margin of the cornea. The canal is lined with a single layer of vascular-derived endothelial cells and transports 2 to 3 µL per minute of aqueous humor from the anterior chamber to the venous plexus. The canal diameter ranges between 170 and 350 µm.

Schlemm's canal inserts may be placed into Schlemm's canal of an eye to facilitate the flow of aqueous humor out of the anterior chamber of the eye by, e.g., supporting tissue in the trabecular meshwork and in Schlemm's canal. The flow facilitated by the presence of the Schlemm's canal insert may include axial flow along Schlemm's canal, flow into Schlemm's canal from the anterior chamber of the eye, and flow leaving Schlemm's canal via the outlets that communicate with the canal.

After exiting Schlemm's canal via the outlets, aqueous humor enters the venous blood stream and is carried along with the venous blood leaving the eye. The pressure of the venous system tends to be around 5-10 mmHg above atmospheric pressure. Accordingly, the venous system provides a pressure backstop which assures that the pressure in the anterior chamber of the eye remains above atmospheric pressure.

In some embodiments, the Schlemm's canal inserts act as reinforcing structures that hold the walls of Schlemm's canal in a patent state so that the walls of the canal provide a flow channel or fistula. The Schlemm's canal inserts may be sized and shaped to reinforce Schlemm's canal while occupying a relatively small portion of the total lateral cross sectional area of Schlemm's canal. In some embodiments, the Schlemm's canal insert provides minimal obstruction to aqueous humor flowing along the length of Schlemm's canal. Reinforcing Schlemm's canal with the Schlemm's canal insert of the disclosure may also encourage a safe healing response over time.

Schlemm's canal inserts of the disclosure may be sized and shaped to facilitate the lateral flow of aqueous humor across and/or through the body of the Schlemm's canal insert. The lateral flow of aqueous humor may include the flow of aqueous humor through the trabecular mesh and into Schlemm's canal. The lateral flow of aqueous humor may also include the flow of aqueous humor through outlets that communicate with Schlemm's canal.

In some patients, Schlemm's canal may have become compartmentalized. When this is the case, Schlemm's canal becomes a series of small compartments separated by discontinuities or partitions. In some embodiments, as the Schlemm's canal insert is advanced into Schlemm's canal, the distal tip of the Schlemm's canal insert penetrates the discontinuities/partitions. This penetrating action re-establishes fluid communication between adjacent compartments. The body of the Schlemm's canal insert facilitates flow across the partitions by remaining in Schlemm's canal after fluid communication has been re-established.

In a diseased eye, Schlemm's canal and/or the upstream tissue can become closed in a way that the outflow of the aqueous humor is less than the inflow and thus the pressure inside the eye increases so that the optic nerve is correspondingly pinched. This visual disturbance, which is known as glaucoma, often leads to blindness of the affected eye or of both eyes. In some embodiments, the Schlemm's canal inserts are used in the treatment of glaucoma arising from local inflammation of the Schlemm's canal and/or the upstream tissue.

The Schlemm's canal inserts can be shaped as fibers, rods, tubes, or stents and are capable of reducing local inflammation. In some embodiments, the fibers have diameters in the range of 0.01-0.15 mm, e.g., 0.01-0.10 mm, 0.04-0.09 mm, 0.05-0.08 mm, or 0.05-0.15 mm. In some embodiments, the fibers have lengths sized for placement within the Schlemm's canal. In other embodiments, the Schlemm's canal inserts are stiff and do not occupy the whole space of the Schlemm's canal. In some embodiments, the Schlemm's canal inserts are smaller than the canal diameter which ranges between 120 and 350 μm.

The Schlemm's canal inserts may have a blunt tip with a rounded shape. For example, the blunt tip may have a hemispherical shape. The rounded shape of the blunt tip may increase the likelihood that the body of the Schlemm's canal implant will track Schlemm's canal as the Schlemm's canal insert is advanced into the canal during insertion of the article of the disclosure.

Some Schlemm's canal inserts, such as tubes or stents, may include an inlet portion that is shaped and sized to extend through the trabecular meshwork of the eye. This inlet portion may provide a flow path between the anterior chamber and Schlemm's canal. In some embodiments, the Schlemm's canal insert is a hollow tube and can facilitate the flow of aqueous humor through its structure.

Insertion of Schlemm's Canal Insert

The Schlemm's canal insert can be introduced into the Schlemm's canal using a syringe or a surgical instrument specifically configured for the injection of the insert into the trabecular formations. This instrument may be a surgical probe that is introduced into Schlemm's canal during the procedure, and subsequently removed completely from the canal after the treatment. In some embodiments, the curved probe is connected to an injection introduced into Schlemm's canal.

In some embodiments, the Schlemm's canal insert is placed into the Schlemm's canal using a Y-shaped tube that has a dual-bonded end and is small enough to fit inside Schlemm's canal. The procedure, similar to a nonpenetrating sclerostomy, begins with the creation of a deep scleral flap and the unroofing of a portion of Schlemm's canal. After Schlemm's canal is defined, the two legs of the tube are inserted in opposite directions down the canal, and the main stem is inserted through a small incision into the anterior chamber. In some embodiments, the Schlemm's canal insert is delivered to the canal and bypasses the juxtacanalicular portion of the trabecular meshwork.

In some embodiments, the Schlemm's canal insert is a stent used in a bypass procedure that reestablishes normal outflow by stenting open the trabecular meshwork and Schlemm's canal. The stent may be inserted into Schlemm's canal internally through a clear corneal incision. This may allow aqueous to flow directly into the canal toward the episcleral drainage system, thus avoiding the trabecular meshwork.

Suprachoroidal Inserts

The suprachoroidal inserts can be introduced into the suprachoroidal space using a syringe or a surgical instrument specifically configured for the implantation of the insert to relieve intraocular pressure. The inserts of the disclosure can create a permanent conduit from the anterior chamber to the suprachoroidal space, draining the aqueous internally rather than accessing Schlemm's canal or the conventional aqueous outflow pathway. Implanted into the supraciliary space through a clear corneal incision, the insert may prevent the formation of a filtering bleb and spare the conjunctiva. The insert of the disclosure can be used for treatment of primary open-angle glaucoma. In an eye with glaucoma, the trabecular outflow pathway may be compromised. The insert of the disclosure can enhance fluid outflow from the anterior chamber of the eye.

For example, the insert can be implanted in conjunction with phacoemulsification cataract surgery. The insert may be implanted through the phaco incision. Intracameral pupil-constricting and viscoelastic agents may be administered to aid in angle visualization and access. The insert can be placed onto a guide instrument that facilities the procedure. In some embodiments, the insert is introduced through paracentesis and guided to the implantation site across the anterior chamber using magnified visualization. The insert may be positioned toward the angle and introduced posterior to the scleral spur at the iris root. In some embodiments, the insert is introduced between ciliary body and the adjacent sclera, through which the insert is advanced. The insert may then be released from the guide instrument. The suprachoroidal insert can enhance the outflow through its structure into the superciliary or suprachoroidal space, and can also release an anti-inflammatory steroid, an antibiotic steroid, or an IOP lowering steroid.

Intravitreal, Subretinal, or Suprachoroidal Injections

Articles of the disclosure may be administered to the eye by intravitreal, subretinal, or suprachoroidal injection. For example, the article (e.g., a small cylinder sized for injection into the eye) can be placed directly into the space in the back of the eye, i.e., the vitreous cavity, which is filled with the vitreous humor gel. Intravitreal injections may be used to administer medications to treat a variety of conditions, including, without limitation, macular edema from retinal vein occlusion, diabetic macular edema, age-related macular degeneration (AMD), diabetic retinopathy, retinal vein occlusion, and uveitis. Alternatively, the articles can be implanted subretinally or suprachoroidally.

EXAMPLES

The following examples, as set forth below, are put forth so as to provide those of ordinary skill in the art with a complete disclosure and description of how the methods and compounds claimed herein are performed, made, and evaluated, and are intended to be purely exemplary of the disclosure and are not intended to limit the scope of what the inventors regard as their disclosure.

Compounds 1-17 can be used in the methods, compositions, and articles of the disclosure.

TABLE 1

Compounds of the disclosure

| Compound | Dimer | Abbreviation |
| --- | --- | --- |
| 1 | Dexamethasone-Triethylene Glycol-Dexamethasone | Dex-TEG-Dex |
| 2 | Hydrocortisone-Triethylene Glycol-Hydrocortisone | HC-TEG-HC |
| 3 | Triamcinolone Acetonide-Triethylene Glycol-Triamcinolone Acetonide | TA-TEG-TA |
| 4 | Dexamethasone-Triethylene Glycol-Hydrocortisone | Dex-TEG-HC |
| 5 | Dexamethasone-Hexane-Dexamethasone | Dex-HEX-Dex |
| 6 | Hydrocortisone-Succinate-Hydrocortisone | HC-SUCC-HC |
| 7 | Anecortave-Triethylene Glycol-Anecortave | Anec-TEG-Anec |
| 8 | Dexamethasone-Pentaethylene Glycol-Dexamethasone | Dex-EG5-Dex |
| 9 | Fusidic Acid-Triethylene Glycol-Fusidic Acid (carbonate ester) | FA-TEG-FA (CE) |
| 10 | Dexamethasone-Polyethylene Glycol (MW = 200)-Dexamethasone | Dex-PEG200-Dex |
| 11 | Dexamethasone-Heptaethylene Glycol-Dexamethasone | Dex-EG7-Dex |
| 12 | Dexamethasone-Nonaethylene Glycol-Dexamethasone | Dex-EG9-Dex |
| 13 | Dexamethasone-Polyethylene Glycol (MW = 300)-Dexamethasone | Dex-PEG300-Dex |
| 14 | Cholesterol-Triethylene Glycol-Cholesterol | CHS-TEG-CHS |
| 15 | Fusidic Acid-Triethylene Glycol-Fusidic Acid (ester) | FA-TEG-FA (E) |
| 16 | Ethinylestradiol-Triethylene Glycol-Ethinylestradiol | Ethin-TEG-Ethin |
| 17 | Prednisolone-Triethylene Glycol-Prednisolone | Pred-TEG-Pred |

Example 1: Compound 1 (Dexamethasone-Triethylene Glycol-Dexamethasone) can be Synthesized, Processed into Pellets in the Glassy State by Heat Molding, and Release Drug Through Surface Erosion from an Intact Pellet Dexamethasone (1 mol equivalent) was suspended in dichloromethane on an ice bath and triethylamine (2 mol equivalent) and triethylene glycol bis(chloroformate) (0.6 mol equivalent) were added to the mixture. The ice bath was allowed to warm to room temperature and the reaction was stirred overnight. The solvent was removed and the solid residue was purified by column chromatography. Product was recrystallized twice from acetonitrile to give Compound 1 (FIG. 1A) as an off-white crystalline solid.

Compound 1: HPLC (mobile phase: $H_2O$/TFA and MeCN/TFA) 31.7 min; Elemental analysis: Anal. Calcd for $C_{52}H_{68}F_2O_{16}$: C, 63.27; H, 6.94; N, 0.00; Cl, 0.00 Found: C, 62.62; H, 6.84; N, <0.50; Cl<100 ppm. $^1$H NMR (400 MHz, DMSO-$d_6$) δ (ppm) 0.80 (d, J=7 Hz, 6H, 2×C16 α-$CH_3$); 0.90 (s, 6H, 2×C18-$CH_3$); 1.08 (m, 2H, 2×C16-H); 1.35 (m, 2H, 2×C14-H); 1.49 (s, 6H, 2×C19-$CH_3$); 1.54 (q, J=13 Hz, 2H, 2×C13-H); 1.64 (q, J=11 Hz, 2H, 2×C15-$CH_2$); 1.77 (m, 2H, 2×C15-$CH_2$); 2.15 (m, 4H, 2×C6-$CH_2$); 2.32 (m, 4H, 2×C7-$CH_2$); 2.62 (m, 2H, 2×C12-$CH_2$); 2.89 (m, 2H, 2×C12-$CH_2$); 3.57 (s, 4H, 2×TEG O$CH_2$); 3.65 (m, 4H, 2×TEG O$CH_2$); 4.15 (m, 2H, 2×OCH); 4.22 (m, 4H, 2×TEG O$CH_2$); 4.79 (d, 2H, AB, J=18.5 Hz, 2H, C21-$CH_2$O—); 5.09 (d, 2H, AB, J=18.5 Hz, 2H, C21-$CH_2$O—); 5.18 (s, 2H, C17-OH); 5.40 (d, 2H, J=4.5 Hz, C11-OH); 6.01 (d, 2H, J=1.9 Hz, 2×alkene C4-CH); 6.23 (dd, 2H, J=10.1 and 1.9 Hz, CH, 2×alkene C2-CH); 7.29 (d, 2H, C1-CH 2×alkene CH, 10.1 Hz, 2H). MS (ESI+) m/z: [M+H]+ Calcd for $C_{52}H_{69}F_2O_{16}$ 987.46; Found 987.46.

Figure 1D:
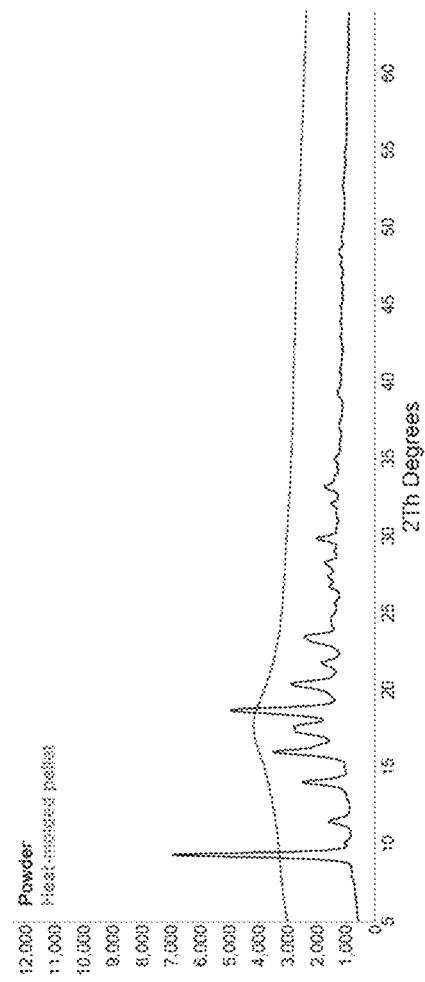
Figure 1A:
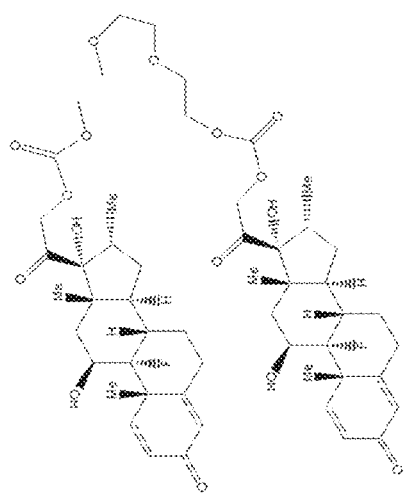
Figure 1B:
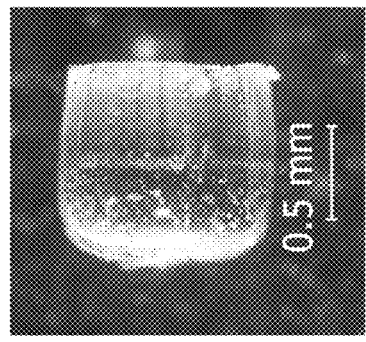

Compound 1 was formed into pellets in the glassy state by heat molding (FIG. 1B). Crystalline powder was melted at 185° C. and pellets were formed from 1 mm×1 mm cylindrical molds. The starting powder and heat-processed pellets were tested by differential scanning calorimetry (DSC; FIG. 1C) and powder x-ray diffraction (PXRD; FIG. 1D) to confirm heat-processing converted compound 1 from the crystalline state to the glassy state.

Figure 1F:
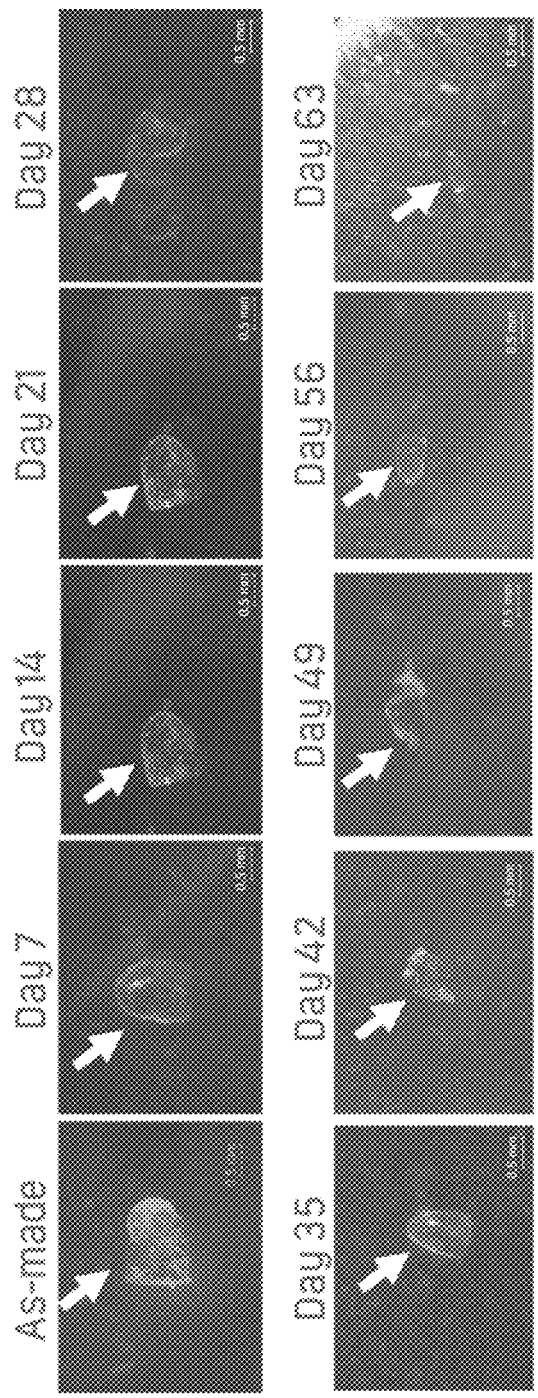

Heat-molded pellets from Compound 1 (~1 mm×1 mm) were placed in 20 mL glass vials and 2 mL of release buffer (either 100% phosphate buffered saline (PBS), 1% fetal bovine serum (FBS) in PBS, or 100% FBS) was added. Samples were incubated at 37° C. on a shaker rotating at 115 rpm. After 1 day, 3 days, 7 days, and subsequently in alternating 3 and 4 day intervals (i.e., 1, 3, 7, 10, 14 days etc.), release buffer was sampled directly (PBS) or syringe filtered, proteins were precipitated with acetonitrile, and drug release products were extracted. The samples were analyzed by high performance liquid chromatography (HPLC) to quantify drug products. Cumulative drug release was calculated and plotted as a percentage of the total drug in each pellet released over time (FIG. 1E). Representative images of the pellets confirm surface erosion over time in 100% FBS (FIG. 1F).

Figure 2D:
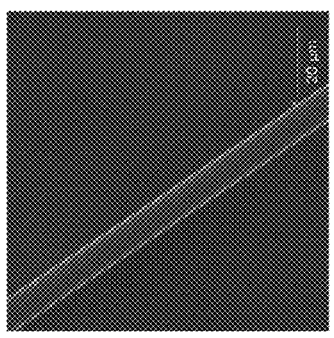
FIG. 2A to FIG. 2G are a series of images showing Compound 1 (Dex-TEG-Dex) processed into different glassy state forms by multiple processing methods from the melt state.
Figure 2G:
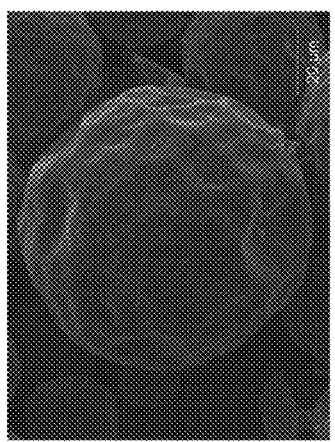
Figure 2C:
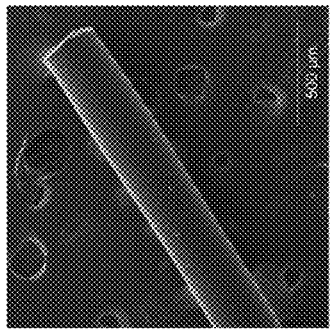
Figure 2F:
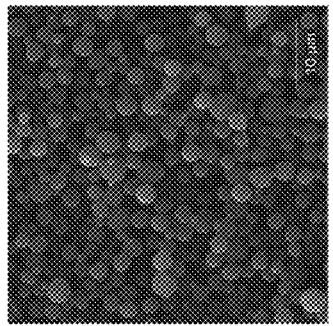
Figure 2B:
Figure 2E:
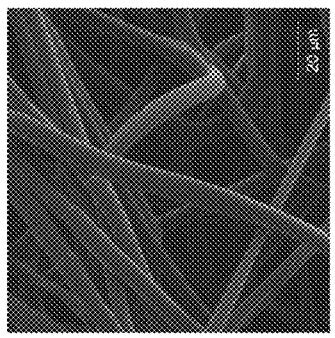
Figure 2A:
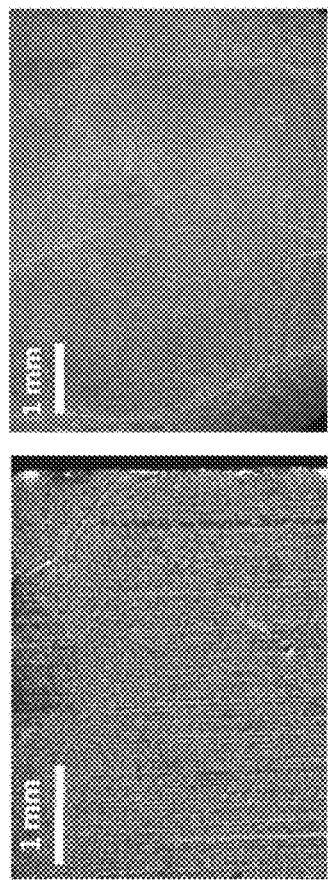

Example 2: Compound 1 (Dex-TEG-Dex) can be Processed into Different Forms in the Glassy State by Multiple Processing Methods from the Melt and Solution States Compound 1 was processed into different forms in the glassy state from the melt and solution states. Compound 1 was coated onto different surfaces from the solution state by dissolving in an organic solvent and applying on a surface using common coating techniques (e.g., dip-coating, spray coating, drop-coating, electrospraying, etc.). FIGS. 2A and 2B show Compound 1 coated on titanium and poly(styrene-block-isobutylene-block-styrene) (SIBS) surfaces, respectively, from acetone. Extruded cylinders were prepared by adding Compound 1 as a crystalline powder into a micro-extruder with different nozzles to form extruded material of different diameters. The micro-extruder was heated to 185° C. to melt the powder and form the extrudate. FIG. 2C shows an extruded cylinder with a 23 G diameter nozzle. Fibers of Compound 1 (FIG. 2D) were prepared by heat extrusion at 185° C. using a small diameter nozzle (e.g., 30-32 G) combined with a tensile force to pull the extrudate out of the nozzle. Fibers were also prepared by melting Compound 1 from a powder at 185° C. and pulling the melted material at different rates to yield fibers of different diameters. Compound 1 was processed into fibrous meshes by electrospinning from the solution state in tetrahydrofuran (FIG. 2E). Micro- and nano-particles were prepared by electrospraying (FIG. 2F) and emulsion (FIG. 2G) from the solution state. Different preparation conditions (solvents, concentrations, surfactants, surfactant concentrations, mixing conditions, etc.) resulted in different particle sizes and distributions.

Figure 3A:
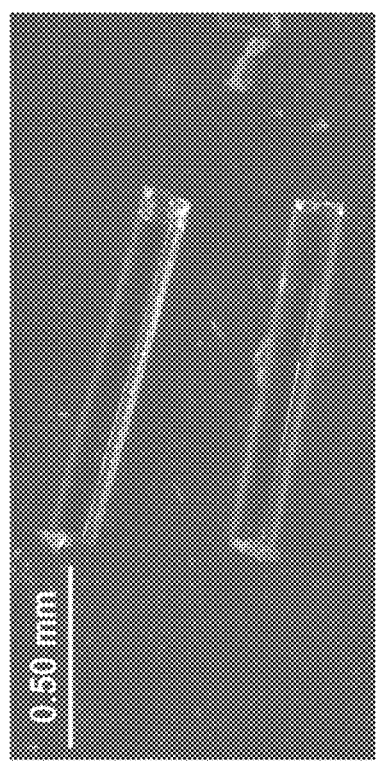
FIG. 3A to FIG. 3F are a series of images and graphs showing Compound 1 formed into heat extruded cylinders (FIGS. 3A-3D), purity of extrudate over time (FIG. 3E), and coating formed from Compound 1 (FIG. 3F).
Figure 3B:
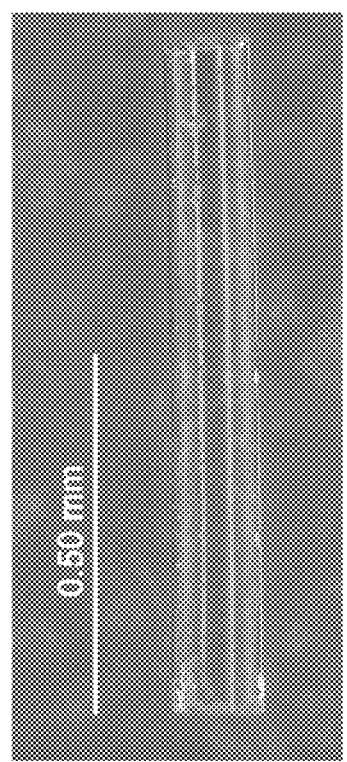
Figure 3C:
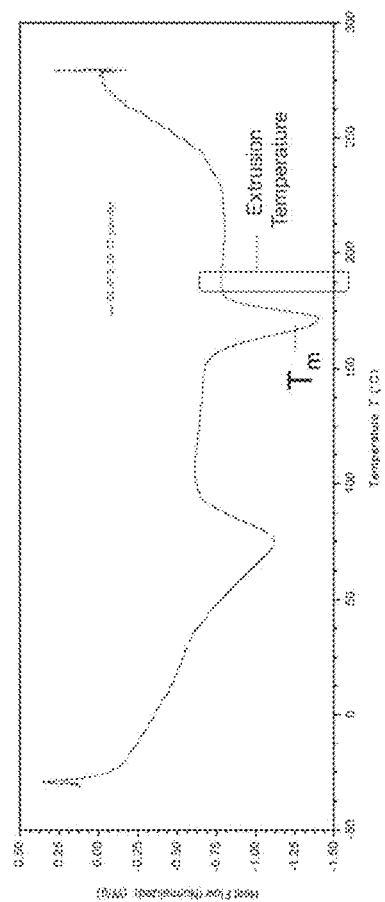
Figure 3D:
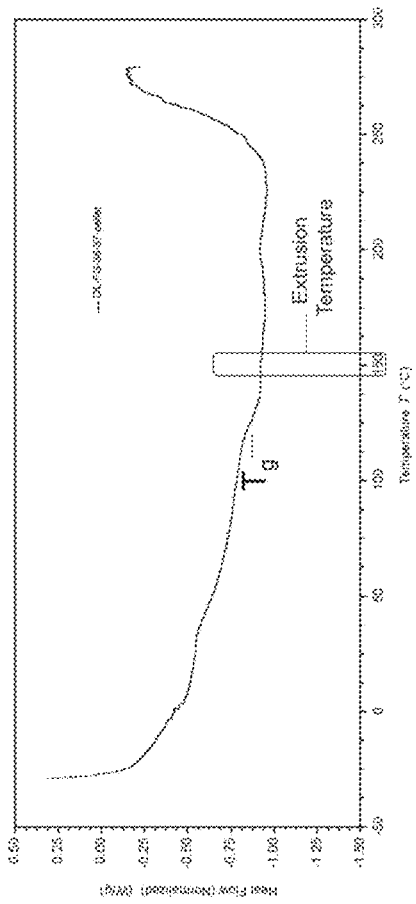
Figure 3F:
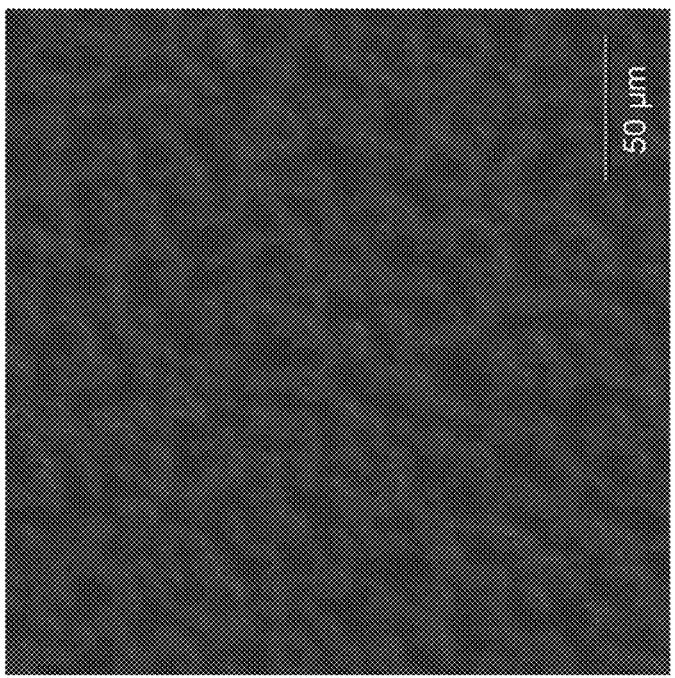
Figure 3E:
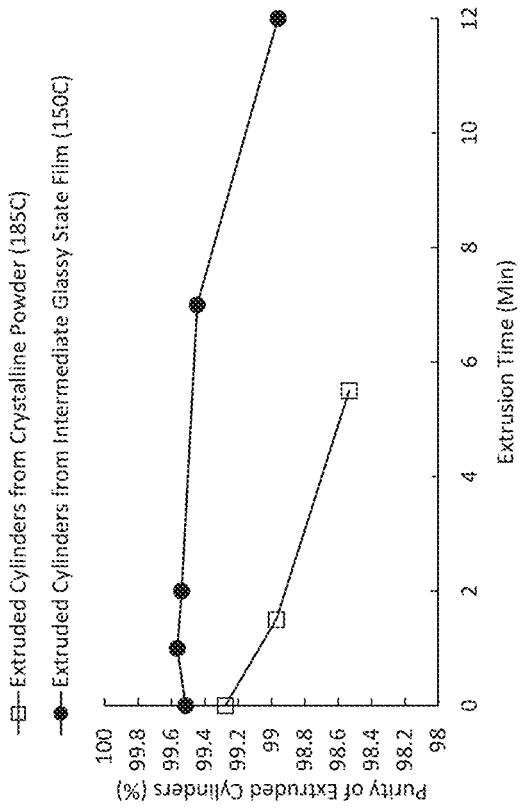

Example 3: Processing Compound 1 (Dex-TEG-Dex) into an Intermediate Glassy State to Manufacture the Final Article Compound 1 (Dex-TEG-Dex) was formed into heat extruded cylinders directly from the crystalline powder by heating above the melting point (185° C.), as shown in FIGS. 3A and 3B, using the methods described above in Example 14. Compound 1 was also formed into heat extruded cylinders by forming an intermediate glassy state form from the melt followed by heat extrusion above the glass transition temperature (150° C.) as shown in FIGS. 3C and 3D. Purity of the extrudate over time is shown in FIG. 3E and demonstrates longer extrusion run times using the intermediate glassy state before Compound 1 drops in purity when compared to extrusion from the melt state.

An intermediate glassy state was also formed from the solution state. Compound 1 was dissolved in acetone and was electrosprayed onto a polymer surface to form glassy state microparticles. The sprayed surface was heated to 150° C. to obtain a coating as shown in FIG. 3F.

Figure 4:
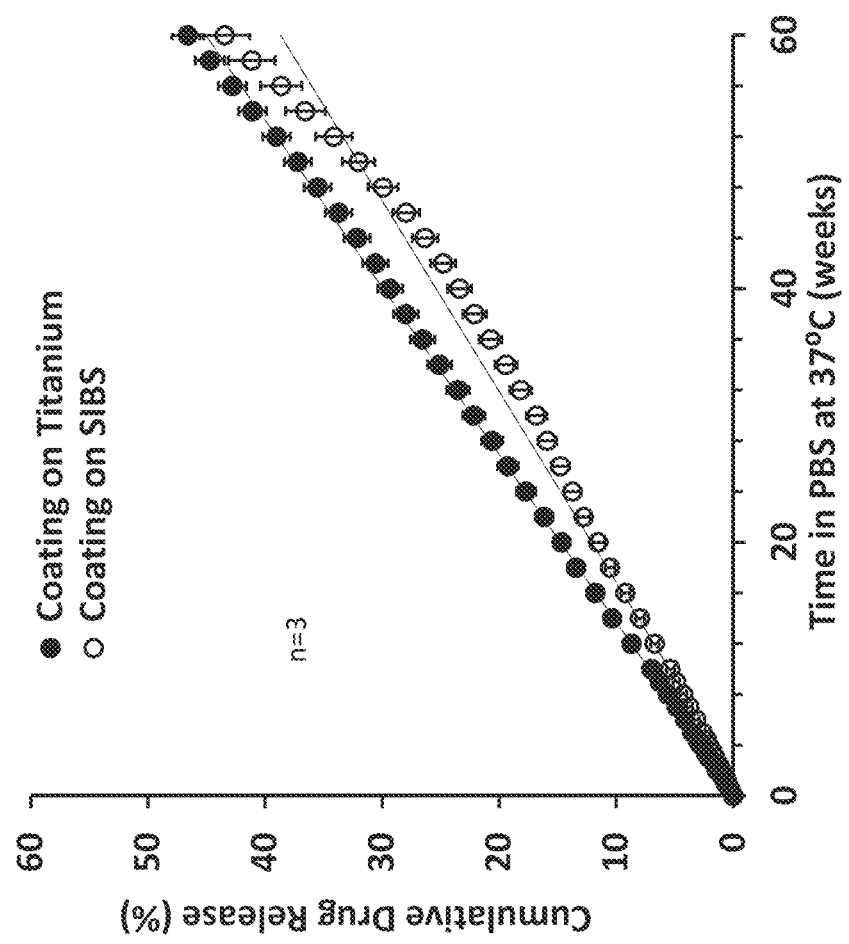
FIG. 4 is a graph showing cumulative drug release from a coating of Compound 1 (Dex-TEG-Dex) from titanium and poly(styrene-block-isobutylene-block-styrene) (SIBS) over time.

Example 4: Drug Release from Compound 1 (Dex-TEG-Dex) Coated on Different Surfaces Compound 1 was coated onto titanium and SIBS as described in Example 3 above. Drug release from the coated material was carried out in PBS as described in Example 1 above. Cumulative drug release was calculated and plotted as a percentage of the total drug in each coated surface released over time (FIG. 4).

Figure 5:
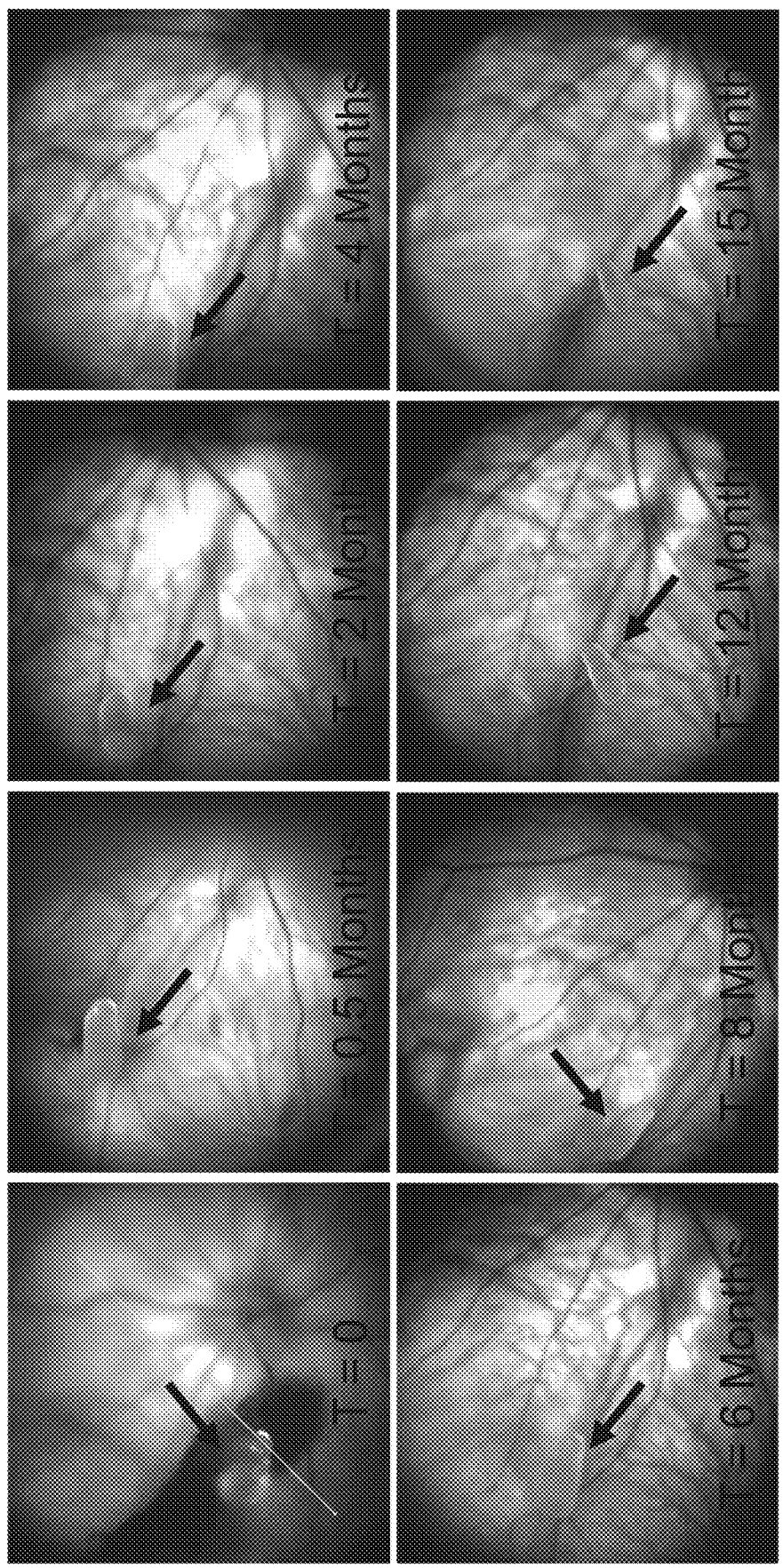
FIG. 5 is a series of images showing surface erosion of an intravitreal implant of Compound 1 (Dex-TEG-Dex) over time.

Example 5: Intravitreal Implants of Compound 1 (Dex-TEG-Dex) Undergo Surface Erosion in the Eye Compound 1 was formed into cylinders by heat molding as described in Example 1. The cylinders were injected intravitreally into rat eyes. Fundus microscopy was used to image the implants non-invasively over time to demonstrate surface erosion of the implant (FIG. 5).

Figure 6B:
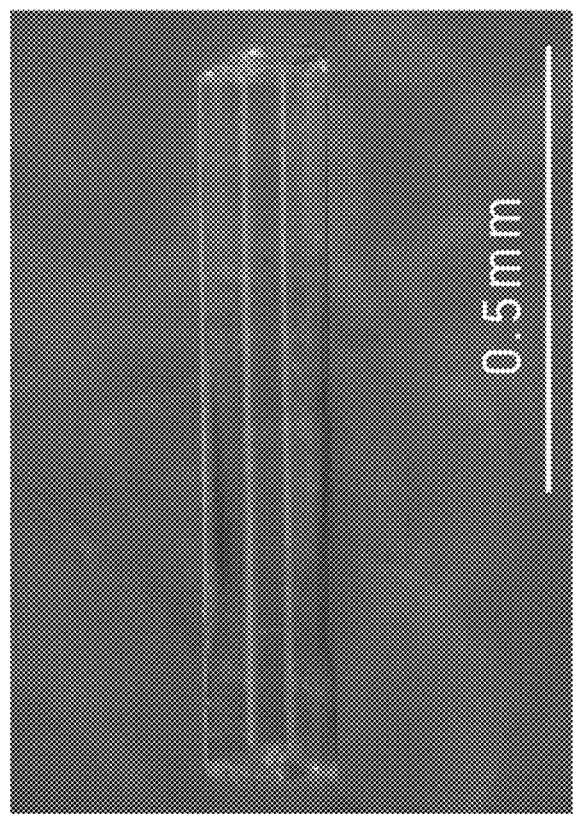
FIG. 6A to FIG. 6I are a series of images and graphs showing intravitreal implants of Compound 1 (Dex-TEG-Dex) formed into cylinders that inhibit inflammation in the eye.
Figure 6A:
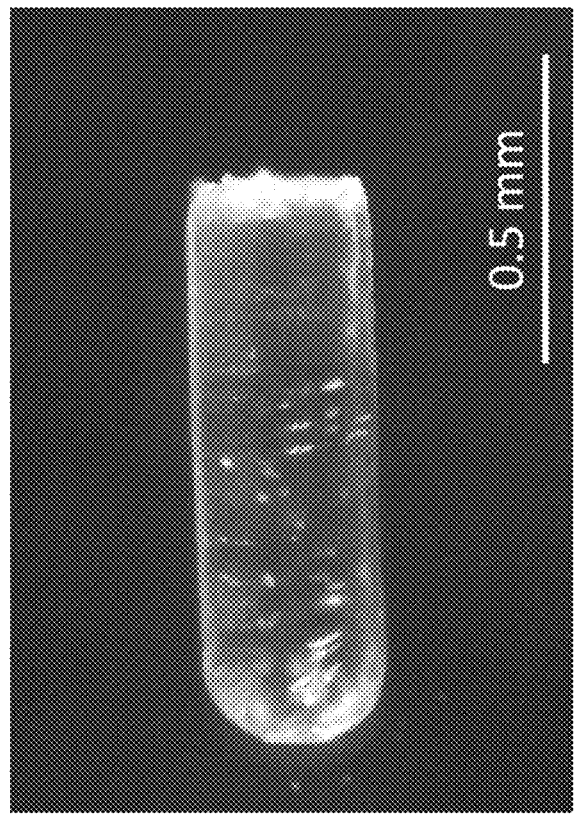
Figure 6D:
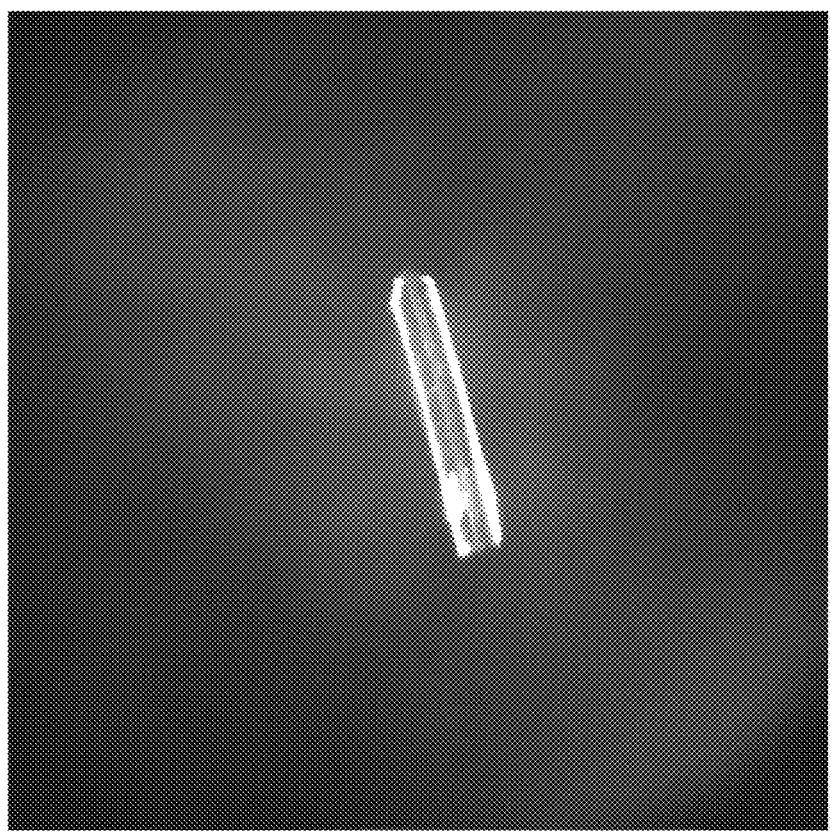
Figure 6C:
Figure 6G:
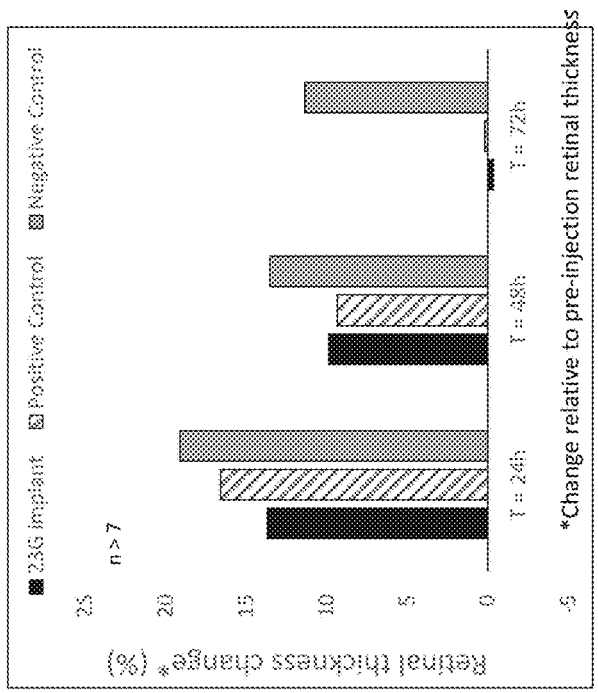
Figure 6F:
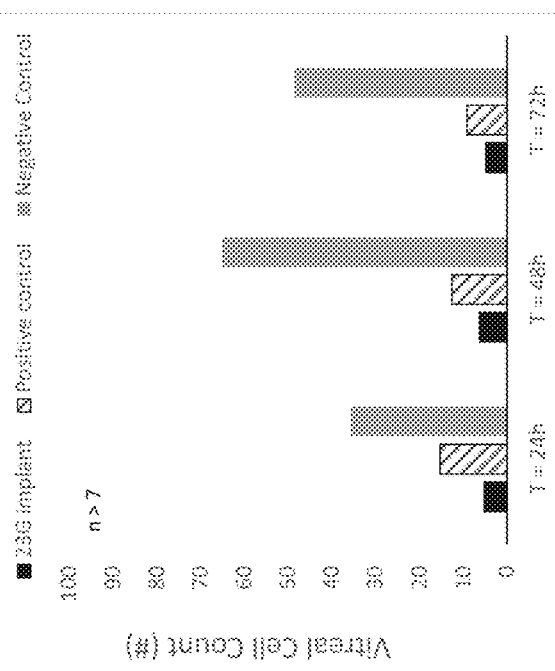
Figure 6E:
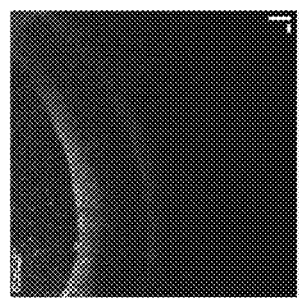
Figure 6I:
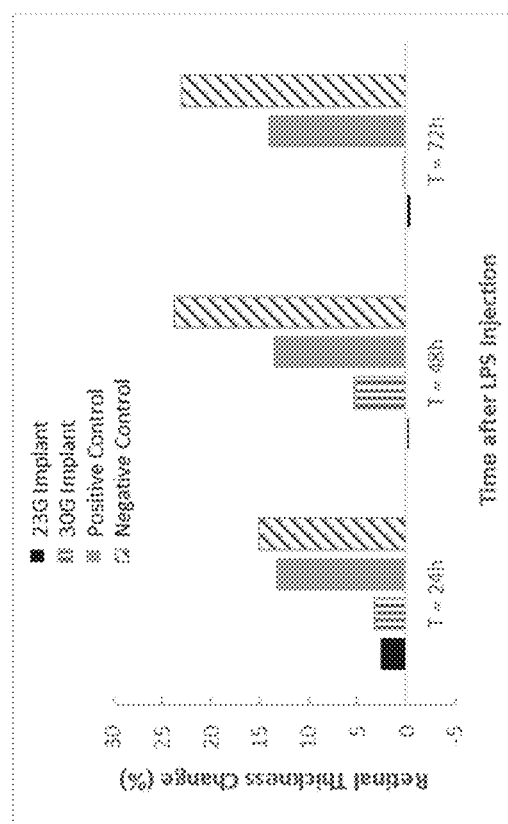
Figure 6H:
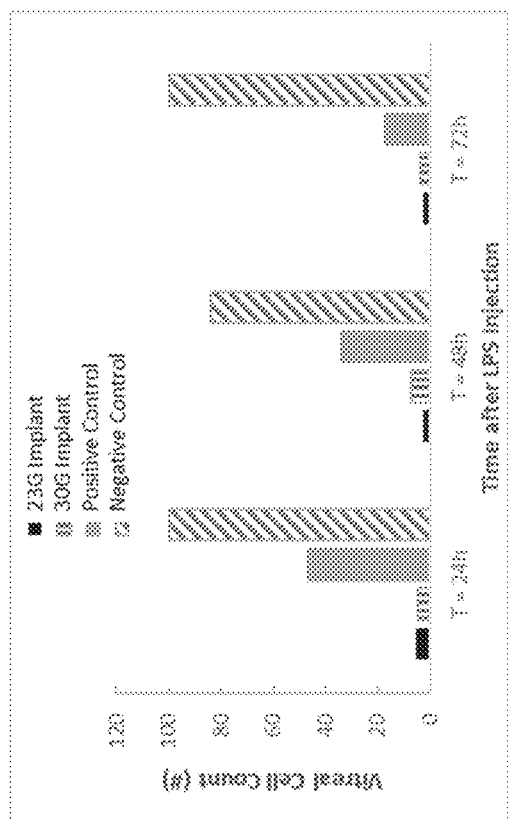

Example 6: Intravitreal Implants of Compound 1 (Dex-TEG-Dex) Release Dexamethasone that Inhibits Endotoxin-Induced Inflammation in the Eye Compound 1 was formed into cylinders by heat molding (~0.34 mm×0.8 mm; FIG. 6A) and heat extrusion from the intermediate glassy state (~0.12 mm×1 mm; FIG. 6B) as described in Examples 1 and 3 above. The implants were loaded into 23 G and 30 G needles respectively and were sterilized by ethylene oxide (ETO) gas. An acute study evaluating only the 23 G heat molded implants was performed and a sub-chronic study evaluating both implants followed. The implants for each study were injected intravitreally into rat eyes and were imaged by fundus microscopy as seen in FIGS. 6C and 6D for the 23 G and 30 G implants, respectively. Inflammation in the eye was induced using an intravitreal injection of the endotoxin lipopolysaccharide (LPS) 1-day post-implantation for the acute study and 60 days post-implantation for the sub-chronic study. Both studies had a negative control arm with eyes receiving a sham 23 G injection and a positive control arm with eyes receiving a sham 23 G injection and dexamethasone eye drops. Optical coherence tomography (OCT) was used to image the eyes (FIG. 6E) and inflammation was assessed by quantifying the number of cells in the vitreous humour and the thickness of the retinal tissue measured from the OCT images. Vitreal cell count and retinal thickness data are shown in FIGS. 6F and 6G, respectively, for the acute study and in FIGS. 6H and 6I, respectively, for the sub-chronic study and demonstrate dexamethasone released from intravitreal implants of Compound 1 inhibit endotoxin-induced inflammation in the eye.

Figure 7A:
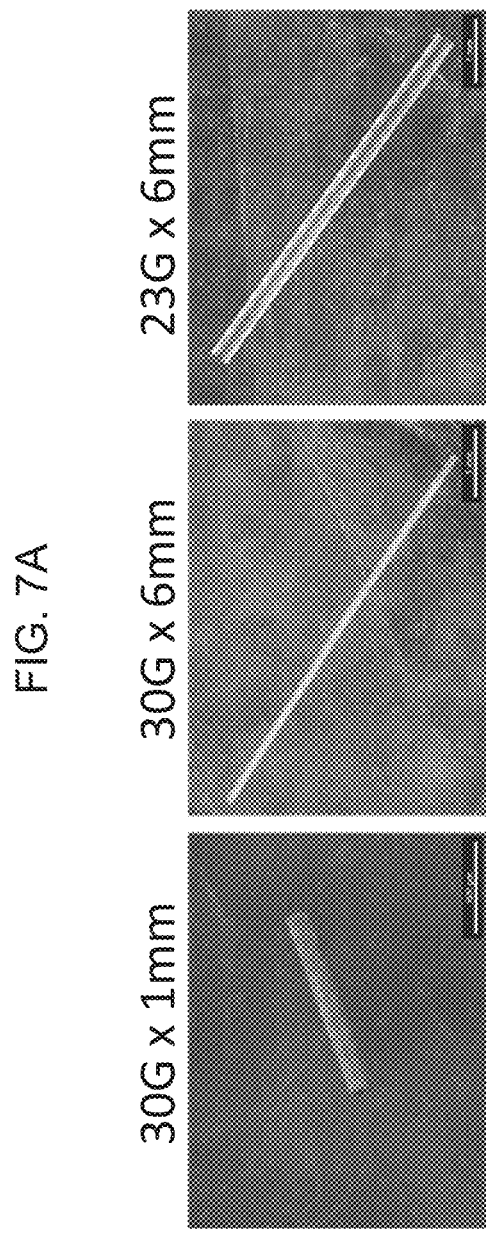
FIG. 7A to FIG. 7D are a series of images and graphs showing intravitreal implants of Compound 1 (Dex-TEG-Dex) and drug release over time.
Figure 7C:
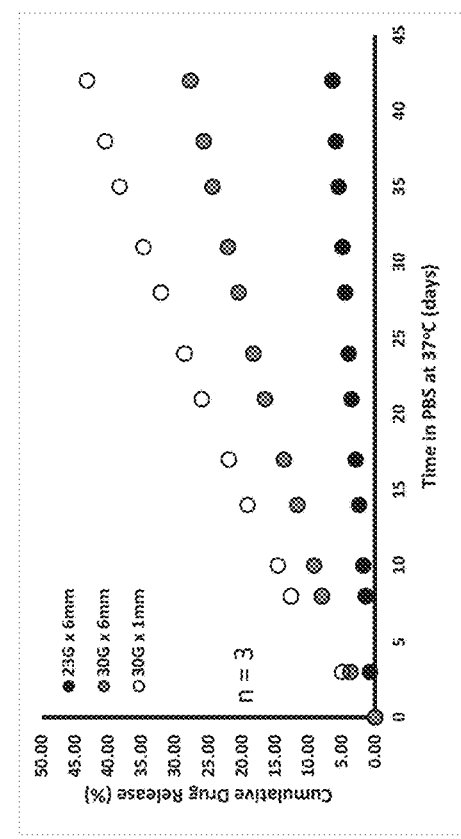
Figure 7B:
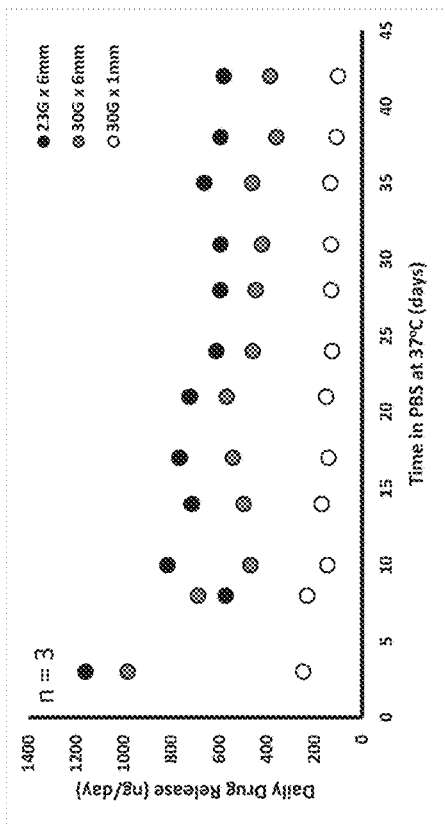
Figure 7D:
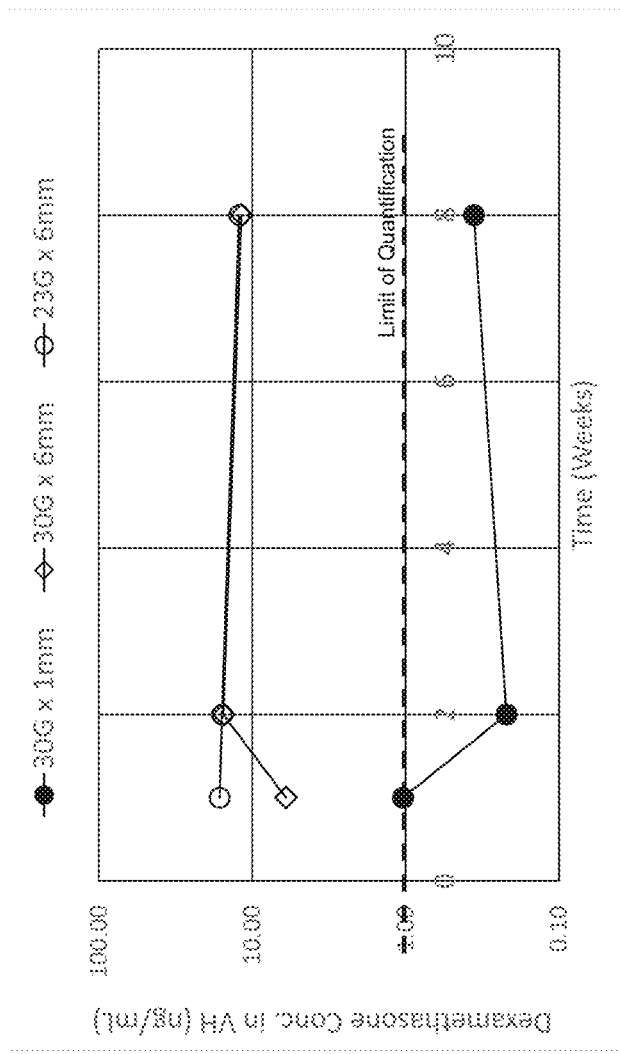

Example 7: Intravitreal Implants of Compound 1 (Dex-TEG-Dex) Release a Consistent Dose of Dexamethasone in the Eye Compound 1 was formed into cylinders by heat extrusion from the intermediate glassy state as described in Example 3. The cylinders were extruded with 23 G and 30 G nozzles. The cylinders were cut to length to form 30 G×1 mm cylinders, 30 G×6 mm cylinders, and 23 G×6 mm cylinders as shown in FIG. 7A. In vitro drug release in PBS was carried out as described in Example 1 with the dose and duration roughly following surface erosion theory as shown in FIGS. 7B and 7C. The cylinders were injected intravitreally into New Zealand white rabbits and dexamethasone was quantified in the vitreous humour at different time points. FIG. 7D plots the drug concentration over time for the different cylinders and shows a consistent dose of dexamethasone is released from the cylinders of Compound 1 in the eye.

Figure 8A:
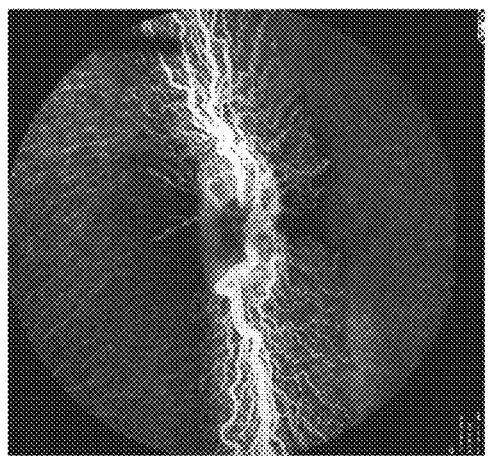
FIG. 8A to FIG. 8D are a series of images showing that intravitreal implants of Compound 1 (Dex-TEG-Dex) inhibit VEGF-induced retinal vascular leakage in the eye.
Figure 8B:
Figure 8C:
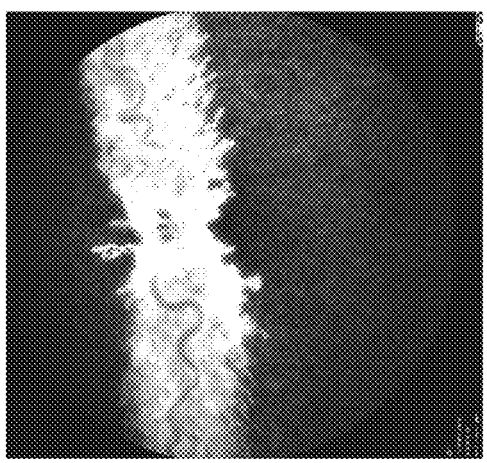
Figure 8D:

Example 8: Intravitreal Implants of Compound 1 (Dex-TEG-Dex) Inhibit Vascular Endothelial Growth Factor (VEGF)-Induced Retinal Vascular Leakage in the Eye Compound 1 was formed into cylinders by heat extrusion from the intermediate glassy state as described in Example 3. The cylinders were extruded with 27 G and 30 G nozzles to get diameters ~0.2 mm and ~0.12 mm respectively. The cylinders were cut to different lengths, ETO gas sterilized, and injected intravitreally into the eyes of Dutch belted rabbits. VEGF was injected intravitreally at 1 week and 10 weeks post-implantation to induce retinal vascular leakage. Sham injection was used as a negative control. Intravitreal implants of Compound 1 provided sustained release of dexamethasone that inhibited VEGF-induced retinal vascular leakage as demonstrated by fundus microscopy (FIG. 8A) and fluorescein angiography (FIG. 8B) compared to negative control (FIGS. 8C and 8D).

Example 9: Intravitreal Implants of Compound 1 (Dex-TEG-Dex) are Used to Treat Inflammatory or Neovascularization Conditions or to Prevent or Reduce Inflammation in the Eye Cylinders of Compound 1 are formed using methods described above. The cylinders are injected into the vitreous humour and release dexamethasone to the surrounding tissues including tissues in the anterior eye, the posterior eye, and surrounding tissues. Dexamethasone released from the cylinder is released by surface erosion over the course of months to years. The intravitreal implants release drug that may be used in subjects with diabetic macular edema, macular edema from retinal vein occlusion, uveitis, cystoid macular edema, post-surgical inflammation (e.g. cataract or glaucoma surgery), age-related macular degeneration, and other ocular conditions.

Example 10: Compound 1 (Dex-TEG-Dex) as a Coating on Minimally Invasive Glaucoma Devices (MIGS)

Coating of Compound 1 is applied onto a MIGS device as described in the methods above. The device is inserted into the eye of a subject to provide fluid flow and reduce intraocular pressure associated with glaucoma. The coating releases dexamethasone into the surrounding tissue to inhibit a tissue response to the device and reduce fibrosis. Drug is released from the device coating into the eye over months to years.

Example 11: Schlemm's Canal Fiber Implant of Compound 1 (Dex-TEG-Dex) are Used to Prevent or Reduce Post-Surgical Inflammation in the Eye A fiber or tube of Compound 1 is formed using the methods described above. The implant is inserted into the Schlemm's canal of a subject having received surgery and releases dexamethasone by surface erosion over weeks to months. The drug released helps to prevent or reduce inflammation associated with the surgical procedure.

Example 12: Intracameral Implants or Wafers of Compound 1 (Dex-TEG-Dex) are Used to Prevent Post-Surgical Inflammation in the Eye Fibers or cylinders are formed from Compound 1 according to the methods described above. The fibers are woven into a mesh and are placed into the eye of a subject having received surgery. Dexamethasone is released from the fiber mesh or cylinder by surface erosion at a steady rate over several months, e.g., three months. Inflammation in the eye is reduced as a result.

Example 13: Micro- or Nanoparticles of Compound 1 (Dex-TEG-Dex) in the Suprachoroidal Space Used to Treat Inflammatory or Neovascularization-Based Conditions or Prevent Inflammation in the Eye Micro- or nanoparticles of Compound 1 are formed using the methods described above. The particles are injected into the suprachoroidal space of a subject with an ocular condition associated with inflammation or neovascularization or as an adjunctive therapy to reduce inflammation associated with ocular surgery. Dexamethasone is released from the particles over months to years and reduces inflammation or neovascularization associated with the condition or surgery.

Example 14: Suprachoroidal Insert of Compound 1 (Dex-TEG-Dex) Reduces Intraocular Pressure A cylinder or tube of Compound 1 is formed using the methods described above. The implant is inserted into the eye of a subject with glaucoma to create a conduit from the anterior chamber into the suprachoroidal space. The conduit allows fluid to flow out of the eye to reduce intraocular pressure. The cylinder or tube undergoes surface erosion to release dexamethasone to modulate the tissue response to the implant and reduce inflammation associated with its placement. The conduit and drug release may last from months to years.

Example 15: Synthesis, Processing, and Drug Release from Heat-Molded Glassy State Pellets of Compounds 2-10 and 17

Compounds 2-10 and 17 were synthesized using standard methods known in the art, similar to the synthesis of Compound 1 in Example 1 above. Details of synthesized Compounds 2 to 10 and 17 are shown in the tables below. Melting points (Tm) and glass transition temperatures (Tg) were determined to establish processing temperatures needed to heat-process the compounds into pellets, fibers, and cylinders for further testing.

TABLE 2

Figure 10B:
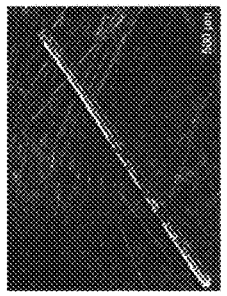
FIG. 10A to FIG. 10E are a series of images and a graph showing Compound 3 (Triamcinolone Acetonide-Triethylene Glycol-Triamcinolone Acetonide, TA-TEG-TA) formed into heat-molded pellets, fibers, and extruded cylinders, as well as drug release over time.
Figure 10C:
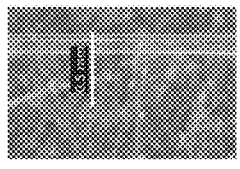
Figure 10D:
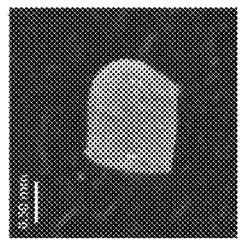
Figure 10E:
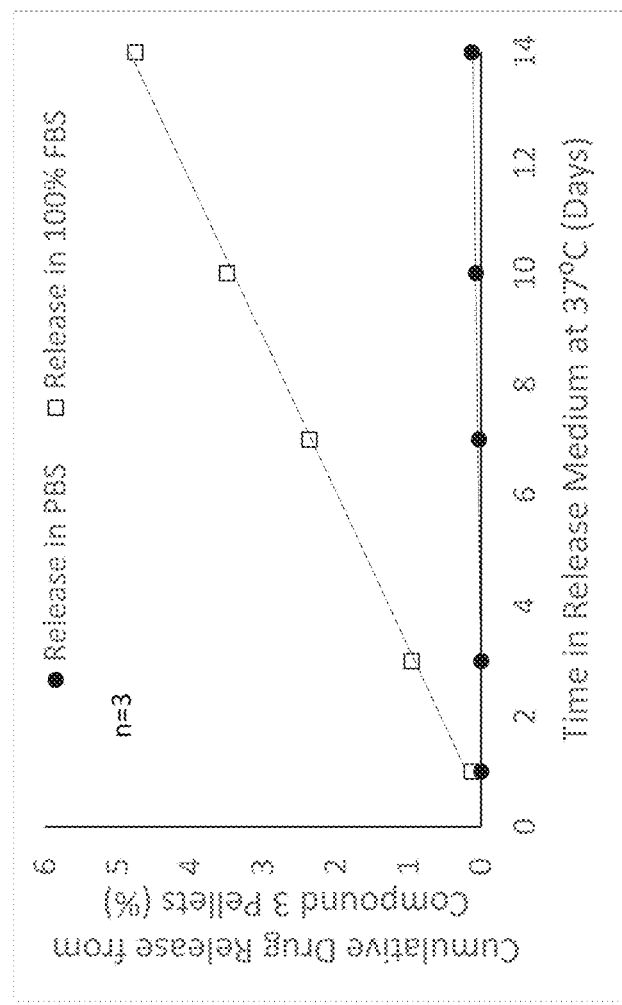
Figure 10A:
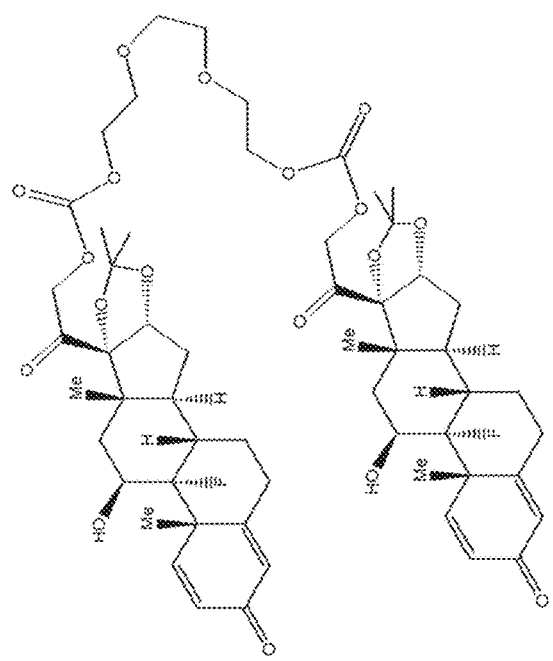
Figure 11C:
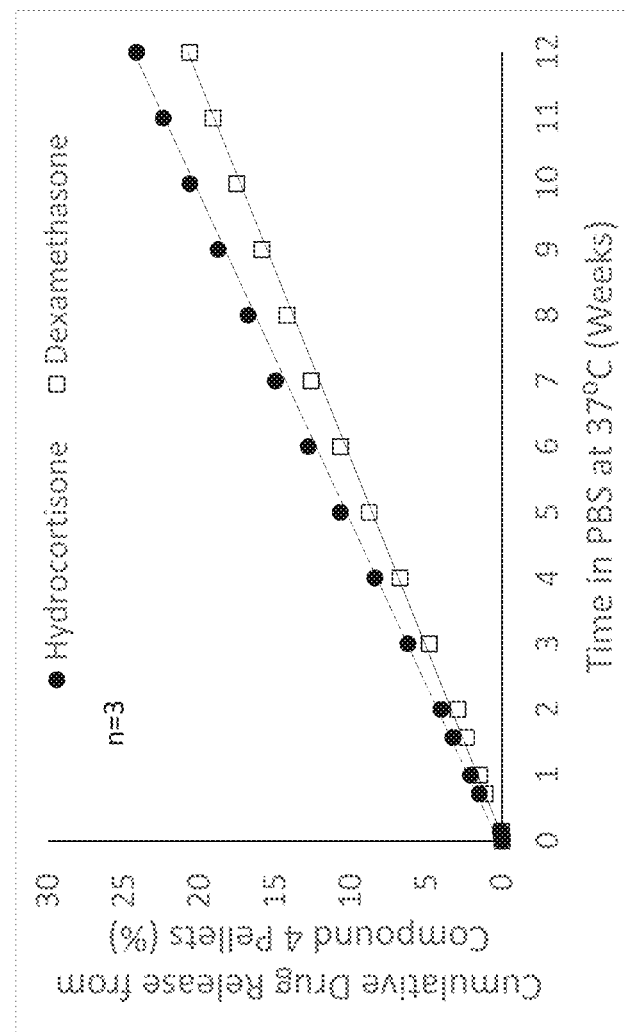
FIG. 11A to FIG. 11C are an image and a graph showing Compound 4 (Dexamethasone-Triethylene Glycol-Hydrocortisone, Dex-TEG-HC) formed into heat-molded pellets and drug release over time.
Figure 11B:
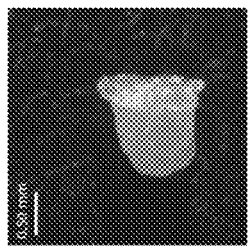
Figure 11A:
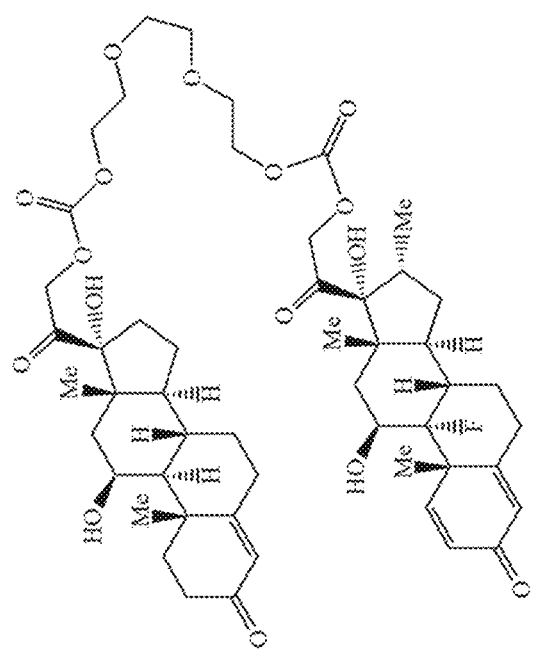

| Structures of Compounds 2-10 | | | | | |
|---|---|---|---|---|---|
| Compound (Abbreviation) | Steroid | Linker | Linking Moiety | Structure | Tm & Tg (° C.) |
| 2 (HC-TEG-HC) | Hydrocortisone | Triethylene Glycol | Carbonate | FIG. 9A | 127 & 113 |
| 3 (TA-TEG-TA) | Triamcinolone Acetonide | Triethylene Glycol | Carbonate | FIG. 10A | 183 & 138 |
| 4 (Dex-TEG-HC) | Dexamethasone & Hydrocortisone | Triethylene Glycol | Carbonate | FIG. 11A | 143 & 120 |
| 5 (Dex-HEX-Dex) | Dexamethasone | Hexane Diol | Carbonate | FIG. 12A | 149 & 146 |
| 6 (HC-SUCC-HC) | Hydrocortisone | Succinic Acid | Ester | FIG. 13A | 157 & 144 |

TABLE 2-continued

Structures of Compounds 2-10

Figure 16B:
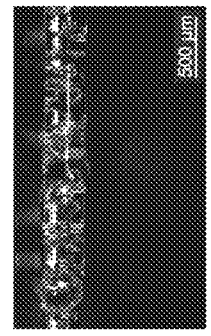
FIG. 16A to FIG. 16E are a series of images and a graph showing Compound 9 (Fusidic Acid-Triethylene Glycol-Fusidic Acid (carbonate ester), FA-TEG-FA (CE)) formed into heat-molded pellets and fibers, as well as drug release over time.
Figure 16C:
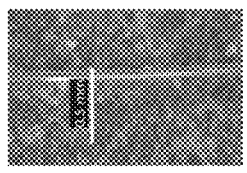
Figure 16D:
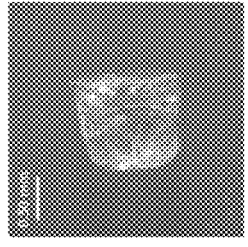
Figure 16E:
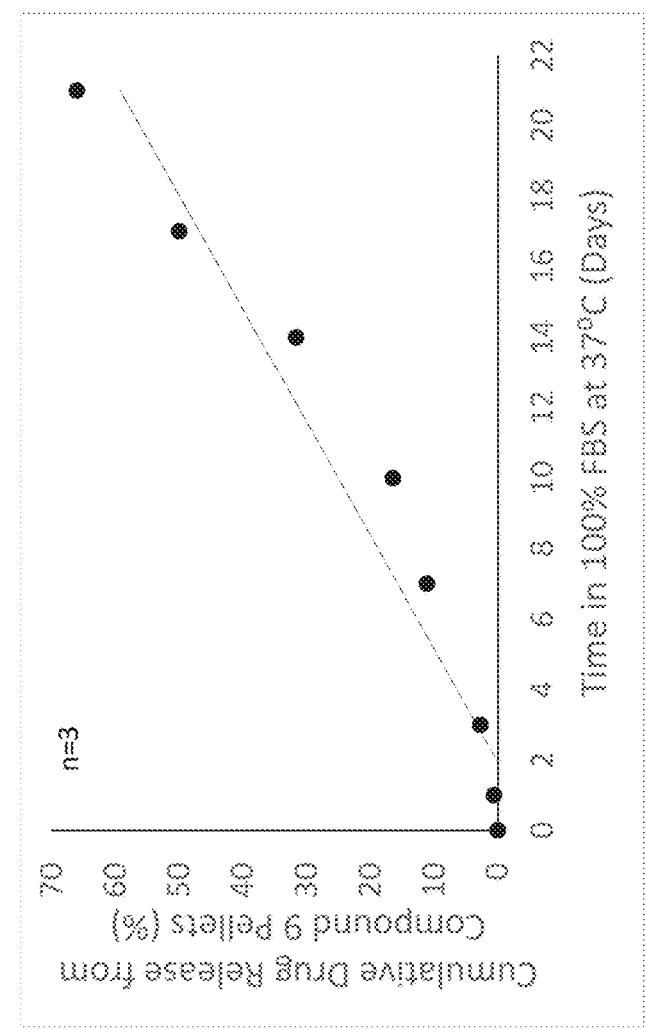
Figure 16A:
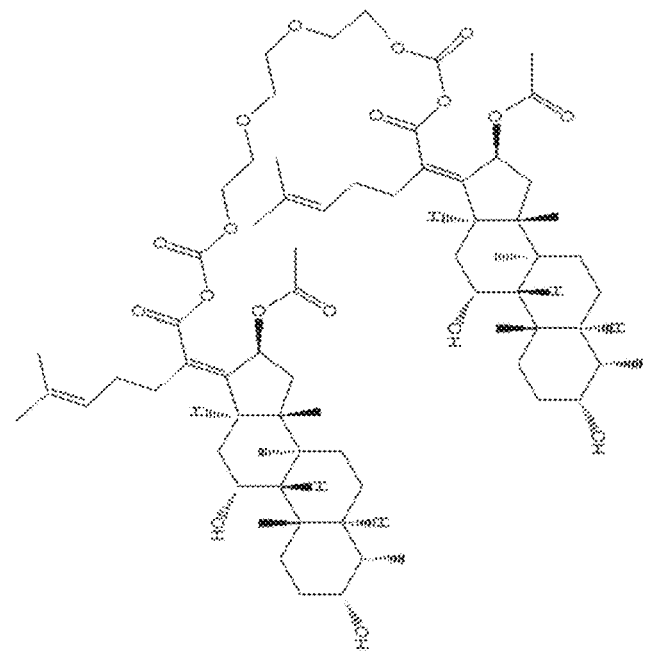
Figure 17B:
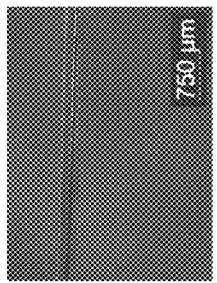
FIG. 17A to FIG. 17D are a series of images and a graph showing Compound 10 (Dexamethasone-Polyethylene Glycol (MW=200)-Dexamethasone, Dex-PEG200-Dex) formed into heat-molded pellets and extruded cylinders, as well as drug release over time.
Figure 17C:
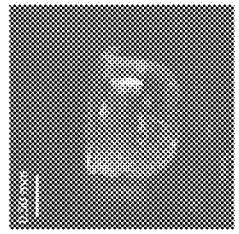
Figure 17D:
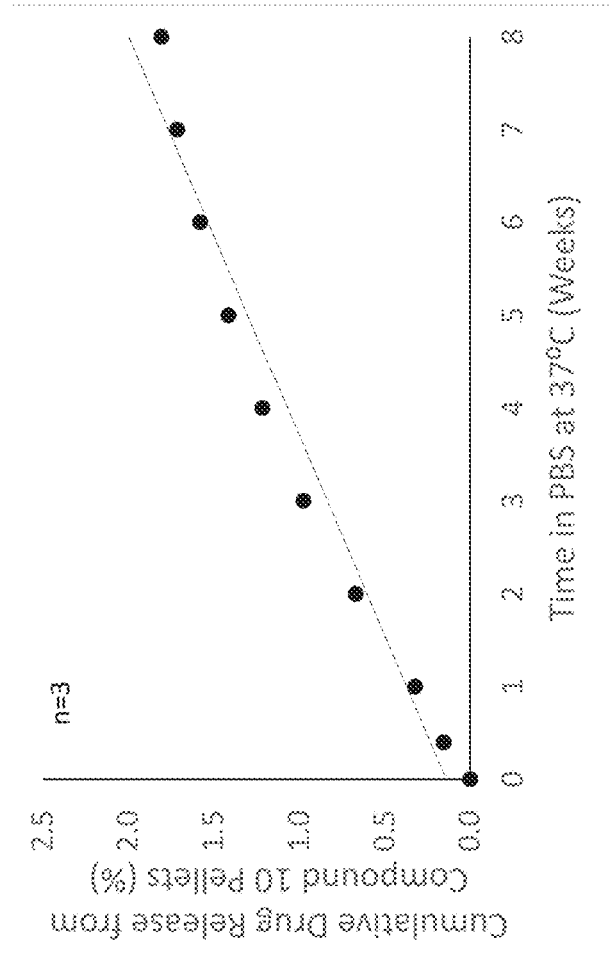
Figure 17A:
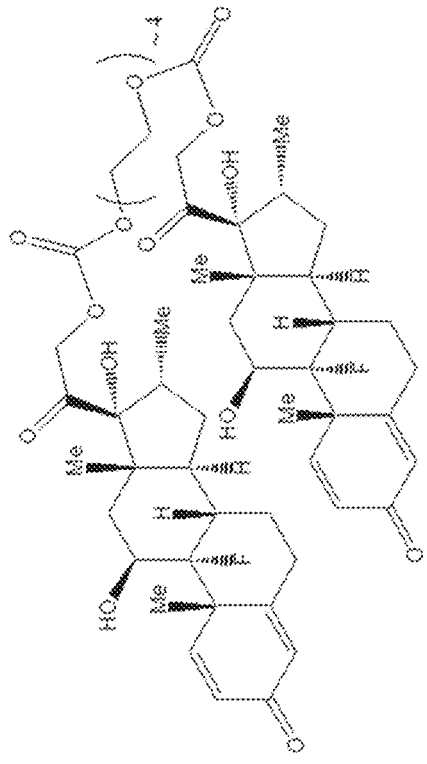
Figures 27A, 27B, 27C:
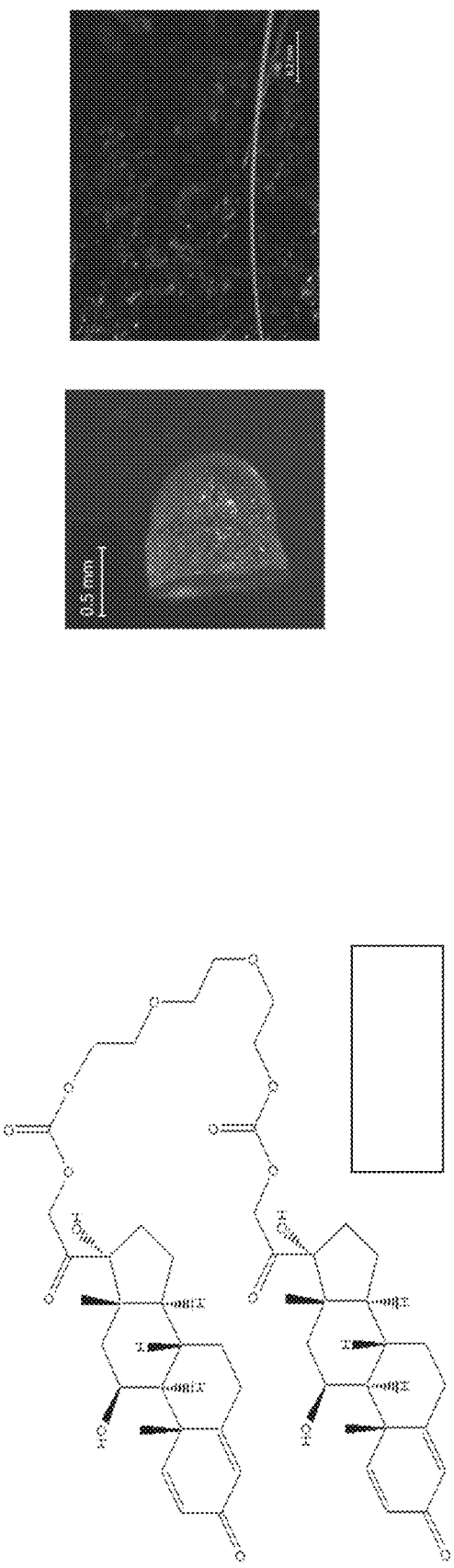
FIG. 27A to FIG. 27C are a series of images showing Compound 17 (Prednisolone-Triethylene Glycol-Prednisolone, Pred-TEG-Pred) formed into heat-molded pellets and fibers.

| Compound (Abbreviation) | Steroid | Linker | Linking Moiety | Structure | Tm & Tg (° C.) |
|---|---|---|---|---|---|
| 7 (Anec-TEG-Anec) | Anecortave | Triethylene Glycol | Carbonate | FIG. 14A | 102 & 100 |
| 8 (Dex-EG5-Dex) | Dexamethasone | Pentaethylene Glycol | Carbonate | FIG. 15A | n.d.* & 66 |
| 9 (FA-TEG-FA(CE)) | Fusidic Acid | Triethylene Glycol | Carbonate Ester | FIG. 16A | 91 & 85 |
| 10 (Dex-PEG200-Dex) | Dexamethasone | Polyethylene Glycol (MW = 200) | Carbonate | FIG. 17A | n.d.* & 96 |
| 17 (Pred-TEG-Pred) | Prednisolone | Triethylene Glycol | Carbonate | FIG. 27A | 128 & 112 |

*n.d. = not determined

Compounds 2-10 and 17 were processed into heat molded pellets (~1 mm×1 mm), fibers from the melt state, and/or heat extruded cylinders from the melt or intermediate glassy state as described in Examples 1-3 above using the appropriate temperature for each compound (i.e. above the Tm or Tg as required). Drug release from the glassy state heat molded pellets was carried out in PBS and/or 100% FBS, as described in Example 1, for different time periods. Cumulative drug release plotted over time demonstrated drug release from different Compounds occurs mostly linearly at different rates from intact pellets in the timeframes tested, similar to Compound 1. Pellets of Compound 4, a heterodimer, released both dexamethasone and hydrocortisone. Figures corresponding to images of the pellets, fibers, and cylinders and drug release curves from pellets are shown in the table below.

TABLE 3

Compounds processed in glassy state

Processed Compounds in Glassy State

| Compound | Heat Molded Pellets | Fibers | Extruded Cylinders | Drug Release |
|---|---|---|---|---|
| 2 (HC-TEG-HC) | FIG. 9B | FIG. 9C | FIG. 9D | FIG. 9E |
| 3 (TA-TEG-TA) | FIG. 10B | FIG. 10C | FIG. 10D | FIG. 10E |
| 4 (Dex-TEG-HC) | FIG. 11B | Not Tested | Not Tested | FIG. 11C |

TABLE 3-continued

Compounds processed in glassy state

Processed Compounds in Glassy State

| Compound | Heat Molded Pellets | Fibers | Extruded Cylinders | Drug Release |
|---|---|---|---|---|
| 5 (Dex-Hex-Dex) | FIG. 12B | FIG. 12C | FIG. 12D | FIG. 12E |
| 6 (HC-SUCC-HC) | FIG. 13B | FIG. 13C | FIG. 13D | FIG. 13E |
| 7 (Anec-TEG-Anec) | FIG. 14B | FIG. 14C | FIG. 14D | FIG. 14E |
| 8 (Dex-EG5-Dex) | FIG. 15B | Not tested | Not tested | FIG. 15C |
| 9 (FA-TEG-FA(CE)) | FIG. 16B | FIG. 16C | FIG. 16D | FIG. 16E |
| 10 (Dex-PEG200-Dex) | FIG. 17B | Not tested | FIG. 17C | FIG. 17D |
| 17 (Pred-TEG-Pred) | FIG. 27B | FIG. 27C | Not tested | Not tested |

Example 16: Synthesis and Processing of Compounds 11-16

Compounds 11-16 were synthesized using standard methods known in the art, similar to the synthesis of Compound 1 in Example 1 above. Details of synthesized Compounds 11-16 are shown in the tables below. Melting points (Tm) and glass transition temperatures (Tg) were determined to establish processing temperatures needed to heat-process the compounds into pellets, fibers, and cylinders for further testing

TABLE 4

Structures of Compounds 11-16

Figure 21A:
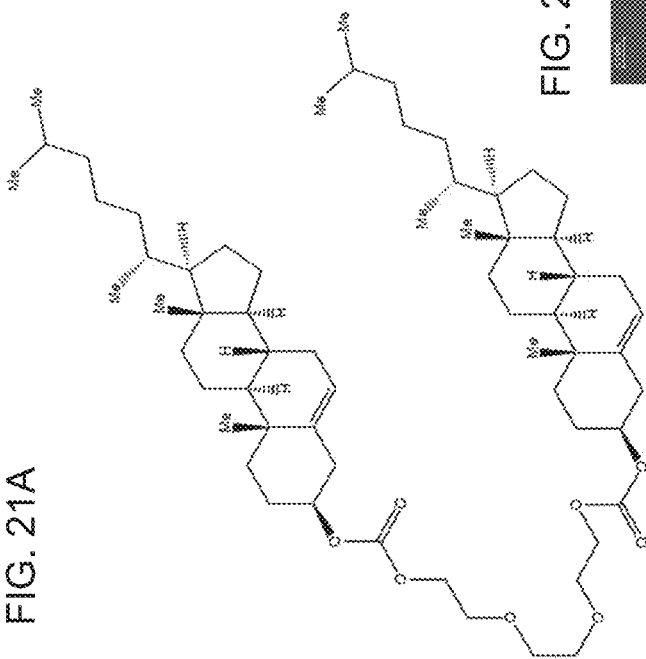
FIG. 21A and FIG. 21B are a series of images showing Compound 14 (Cholesterol-Triethylene Glycol-Cholesterol, CHS-TEG-CHS) formed into heat-molded pellets.
Figure 20A:
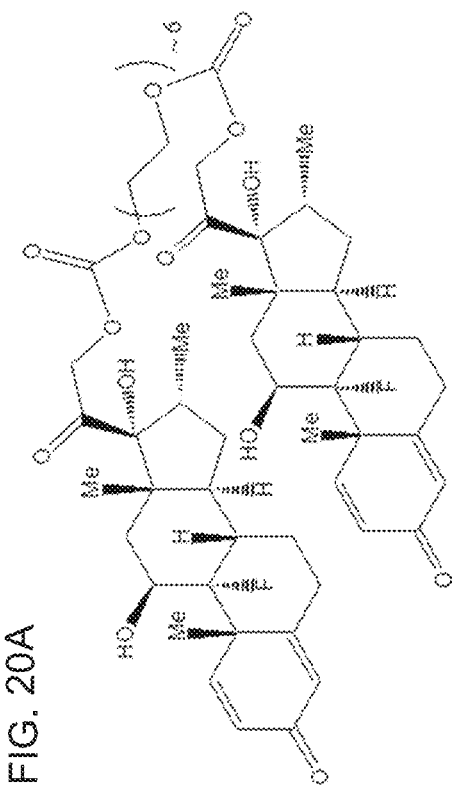
FIG. 20A and FIG. 20B are a series of images showing Compound 13 (Dexamethasone-Polyethylene Glycol (MW=300)-Dexamethasone, Dex-PEG300-Dex) formed into heat-molded pellets.

| Compound (Abbreviation) | Steroid | Linker | Linking Moiety | Structure | Tm & Tg (° C.) |
|---|---|---|---|---|---|
| 11 (Dex-EG7-Dex) | Dexamethasone | Heptaethylene Glycol | Carbonate | FIG. 18A | 51 & 47 |
| 12 (Dex-EG9-Dex) | Dexamethasone | Nonaethylene Glycol | Carbonate | FIG. 19A | 41 & 37 |
| 13 (Dex-PEG300-Dex) | Dexamethasone | Polyethylene Glycol (MW = 300) | Carbonate | FIG. 20A | 77 & 75 |
| 14 (CHS-TEG-CHS) | Cholesterol | Triethylene Glycol | Carbonate | FIG. 21A | 99 & 22 |

TABLE 4-continued

Structures of Compounds 11-16

Figure 22A:
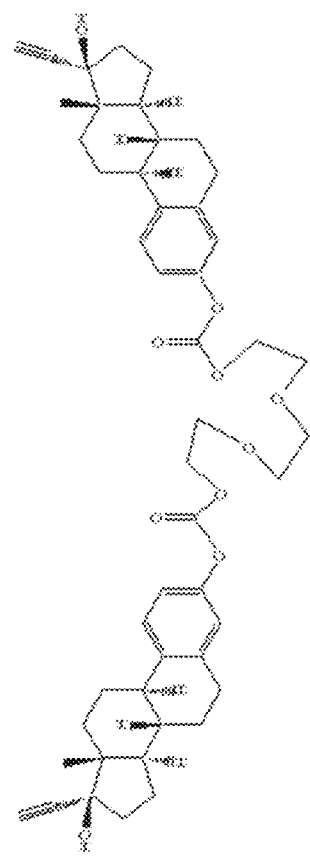
FIG. 22A and FIG. 22B are a series of images showing Compound 15 (Fusidic Acid-Triethylene Glycol-Fusidic Acid (ester), FA-TEG-FA (E)) formed into heat-molded pellets.
Figure 23A:
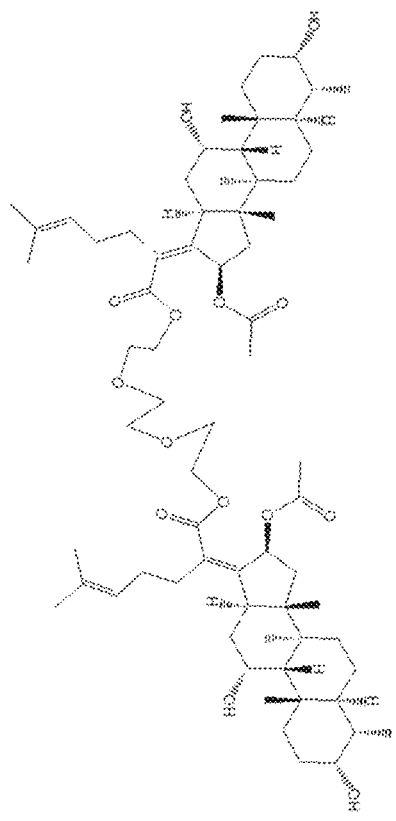
FIG. 23A and FIG. 23B are a series of images showing Compound 16 (Ethinylestradiol-Triethylene Glycol-Ethinylestradiol, Ethin-TEG-Ethin) formed into heat-molded pellets.

| Compound (Abbreviation) | Steroid | Linker | Linking Moiety | Structure | Tm & Tg (° C.) |
|---|---|---|---|---|---|
| 15 (FA-TEG-FA(E)) | Fusidic Acid | Triethylene Glycol | Ester | FIG. 22A | 87 & 84 |
| 16 (Ethin-TEG-Ethin) | Ethinylestradiol | Triethylene Glycol | Carbonate | FIG. 23A | 61 & 53 |

*n.d. = not determined

TABLE 5

Heat-molded pellets formed from Compounds 11-16

Figure 21B:
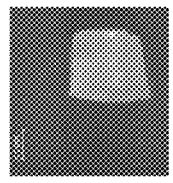
Figure 20B:
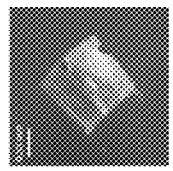
Figure 22B:
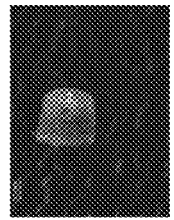
Figure 23B:
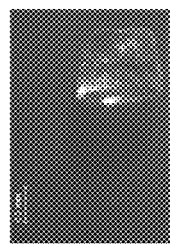

| Compound | Heat Molded Pellets |
|---|---|
| 11 (Dex-EG7-Dex) | FIG. 18B |
| 12 (Dex-EG9-Dex) | FIG. 19B |
| 13 (Dex-PEG300-Dex) | FIG. 20B |
| 14 (CHS-TEG-CHS) | FIG. 21B |
| 15 (FA-TEG-FA(E)) | FIG. 22B |
| 16 (Ethin-TEG-Ethin) | FIG. 23B |

Example 17: Intracameral Implants of Compound 7 (Anec-TEG-Anec) are Used to Lower Intraocular Pressure in the Eye Cylinders, pellets, or fibrous meshes of Compound 7 are formed using the methods described above. The implants are inserted intracamerally into subjects with glaucoma. The implants release anecortave through surface erosion over months to years and lower intraocular pressure in the eye.

Example 18: Suprachoroidal Inserts of Compound 7 (Anec-TEG-Anec) are Used to Lower Intraocular Pressure in the Eye A cylinder or tube of Compound 7 is formed using the methods described above. The implant is inserted into the eye of a subject with glaucoma to create a conduit from the anterior chamber into the suprachoroidal space. The cylinder or tube undergoes surface erosion to release anecortave. Both the conduit and released drug act to reduce intraocular pressure and may last from months to years.

Example 19: Intracameral Implants of Compound 9 (FA-TEG-FA (CE)) are Used to Prevent Post-Surgical Infection in the Eye Cylinders, pellets, or fibrous meshes of Compound 9 are formed using the methods described above. The implants are inserted intracamerally into subjects that are receiving an ocular surgical procedure. The implants release fusidic acid over days to weeks to a few months to prevent infection.

Example 20: Heat-Molded Pellets in the Glassy State can be Formed from Mixtures of Two Dimers and Drugs are Released from Both Compounds of the Intact Pellet Pellets in the glassy state were formed by heat molding a mixture of compounds as shown in the table below. The starting crystalline compounds were mixed together and were heat molded at a temperature above the higher melting point compound. Drug release from the pellets (~1 mm×1 mm and 1 mg of total mixture) was carried out in PBS as described in Example 1. Cumulative drug release was calculated and plotted as a percentage of the total drug released over time. Linear drug release from intact pellets was observed for both compounds in the mixed pellets.

TABLE 6

Heat-molded pellets formed from mixtures of two compounds and drug release

Figure 26A:
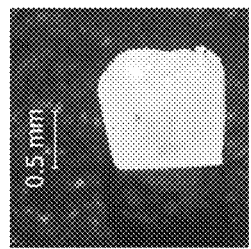
FIG. 26A and FIG. 26B are a series of an image and a graph showing a mixture of Compound 2 (HC-TEG-HC) and Compound 3 (TA-TEG-TA) formed into heat-molded pellets and drug release.
Figure 26B:
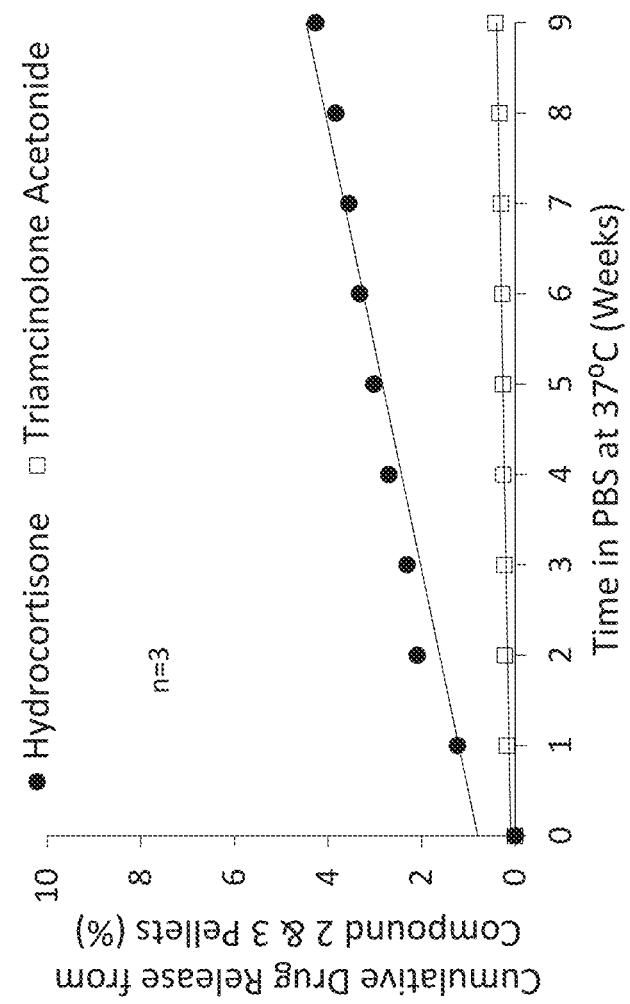

| Mixture | Components of Mixture | Ratio | Heat-Molded Pellet | Drug Release |
|---|---|---|---|---|
| A | Compound 1 (Dex-TEG-Dex) & Compound 2 (HC-TEG-HC) | 1:1 w/w | FIG. 24A | FIG. 24B |
| B | Compound 1 (Dex-TEG-Dex) & Compound 3 (TA-TEG-TA) | 1:1 w/w | FIG. 25A | FIG. 25B |
| C | Compound 2 (HC-TEG-HC) & Compound 3 (TA-TEG-TA) | 1:1 w/w | FIG. 26A | FIG. 26B |

Example 21: Intracameral Implants of Compound 1 (Dex-TEG-Dex) and Compound 9 (FA-TEG-FA (CE)) are Used to Inhibit Post-Surgical Inflammation and Infection Cylinders, pellets, or fibrous meshes of Compound 1 and 9 are formed using the methods described above. The implants are inserted intracamerally into subjects that are receiving an ocular surgical procedure. The implants release dexamethasone and fusidic acid over days to weeks to a few months to reduce inflammation associated with the surgery and prevent infection.

Example 22: Delivery of Schlemm's Canal Insert into Schlemm's Canal

The articles of the disclosure can be inserted into the Schlemm's canal in a surgical procedure that generally includes the steps of creating an incision in the ocular wall that provides access to the anterior chamber of the eye; advancing a cannula of the system through the incision, across a portion of the anterior chamber, to the trabecular meshwork, and piercing the trabecular meshwork; accessing Schlemm's canal with the cannula; and implanting the article (i.e., a Schlemm's canal insert) within the canal. The cannula typically includes a proximal end and a distal curved portion, the distal curved portion having a proximal end and a distal end and a radius of curvature defined between the ends; a body; a distal tip having a bevel, the bevel directly engaging the distal end of the curved portion of the cannula; and a lumen extending from the proximal end through the distal tip. A positioning element slidable within the cannula lumen may be employed during the step of implanting the Schlemm's canal insert within the canal. The Schlemm's canal insert may be implanted to reduce inflammation, reduce intraocular pressure, or to treat a medical condition such as glaucoma, pre-glaucoma, or ocular hypertension.

The method for treating conditions of the eye may include advancing a conduit into Schlemm's canal, where the conduit has been loaded with the Schlemm's canal insert, and delivering the Schlemm's canal insert into Schlemm's canal at a size sufficient to disrupt the trabeculocanalicular tissues to reduce intraocular pressure.

The method can be performed in conjunction with cataract surgery to insert the anti-inflammatory steroids for the purpose of reducing the risk of post-surgical complications.

Some embodiments of the disclosure provided herein can be defined according to the following numbered items:

1. A method of treating an ocular condition in an eye of a subject in need thereof, said method comprising contacting the eye with an article formed from a compound of formula (A-I):

D1-L-D2    (A-I), or a pharmaceutically acceptable salt thereof, wherein each of D1 and D2 is, independently, a radical formed from a steroid selected from an antibiotic steroid, a glucocorticoid steroid, an anti-angiogenic steroid, an intraocular pressure (TOP) lowering steroid, and a corticosteroid; and L is a linker covalently linking D1 to D2.

2. The method of item 1, wherein L is covalently linked to D1 and to D2 via one or more ester, carbonate, carbonate ester, or anhydride linkages.

3. The method of item 2, wherein L is covalently linked to D1 and to D2 via one or more carbonate linkages.

4. The method of any one of items 1-3, wherein L comprises the radical —(C(O)—(R$^A$)—C(O)— or —O—(R$^A$)—O—;

R$^A$ is a radical of a polyol and includes at least one free hydroxyl group or R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and q, r, and s are integers from 1 to 10.

5. The method of any one of items 1-4, wherein D1 and D2 are formed from the same steroid and the compound is further described by one of formulas (II-a)-(II-r).

6. The method of any one of items 1-5, wherein D1 and D2 are formed from different steroids and each of D1 and D2 are, independently, further described by one of formulas (I-a)-(I-r).

7. The method of any one of items 1-6, wherein at least 70% (w/w) of the article is the compound of formula (A-I).

8. The method of item 7, wherein at least 90% (w/w) of the article is the compound of formula (A-I).

9. The method of any one of items 1-8, wherein the compound, D1, or D2 are released from the article through surface erosion.

10. The method of item 9, wherein the surface erosion releases less than 10% of D1 or D2, as a percentage of the total drug, D1 or D2, present in the article in prodrug form, at 37° C. in 100% bovine serum over 5 days; or the surface erosion releases less than 2% of D1 or D2, as a percentage of the total drug, D1 or D2, present in the article in prodrug form, at 37° C. in PBS over 5 days; or the surface erosion releases greater than 20% of D1 or D2, as a percentage of the total drug, D1 or D2, present in the article in prodrug form, at 37° C. in 100% bovine serum over not fewer than 6 days; or the surface erosion releases greater than 5.0% of D1 or D2, as a percentage of the total drug, D1 or D2, present in the article in prodrug form, at 37° C. in PBS over not fewer than 6 days; or D1 and/or D2 is released from the article at a rate such that $t_{10}$ is greater than or equal to $\frac{1}{10}$ of $t_{50}$.

11. The method of any one of items 1-10, wherein the article further comprises from 0.1% to 10% (w/w) of one or more additives, wherein the one or more additives are selected from plasticizers, antioxidants, binders, lubricants, dyes, and mixtures thereof.

12. The method of any one of items 1-11, wherein the article is a fiber, fiber mesh, woven fabric, non-woven fabric, pellet, cylinder, microparticle, nanoparticle, or shaped article.

13. The method of any one of items 1-11, wherein the article is in the form of a punctal plug, a stent, or a tube.

14. The method of any one of items 1-11, wherein the article is a fiber, a cylinder, a stent, or a tube.

15. The method of any one of items 1-11, wherein the article is a cylinder and the method further comprises intravitreally, subretinally, or suprachoroidally injecting the article into the eye.

16. The method of any one of items 1-15, wherein the ocular condition is an inflammatory condition.

17. The method of item 16, wherein the inflammatory condition is macular edema from retinal vein occlusion, diabetic macular edema, uveitis, diabetic retinopathy, or age-related macular degeneration (AMD).

18. The method of item 16, wherein upon hydrolysis, D1 and D2 form a corticosteroid or a glucocorticoid steroid.

19. The method of item 18, wherein said compound is further described by the formula (III):

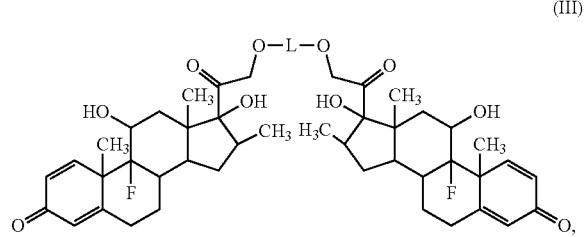

(III)

or a pharmaceutically acceptable salt thereof, wherein
L is —C(O)O—(R$^A$)—OC(O)—, —C(O)—OC(O)—(R$^A$)—C(O)O—C(O)—; R$^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

20. The method of any one of items 1-15, wherein the ocular condition is a bacterial infection.

21. The method of any one of items 1-15, wherein the ocular condition is conjunctivitis, keratitis, trachoma, or endophthalmitis.

22. The method of item 20, wherein upon hydrolysis, D1 and D2 form fusidic acid.

23. The method of any one of items 1-15, wherein upon hydrolysis D1 and D2 form an anti-angiogenic steroid or an intraocular pressure (TOP) lowering steroid.

24. The method of item 23, wherein upon hydrolysis D1 and D2 form anecortave acetate, anecortave, 11-epicortisol, 17α-hydroxyprogesterone, tetrahydrocortexolone, or tetrahydrocortisol.

25. The method of item 23 or 24, wherein the compound of formula (A-I) is administered intravitreally to the eye of the subject.

26. The method of item 23 or 24, wherein the compound of formula (A-I) is administered to the suprachoroidal space of an eye of the subject.

27. The method of any one of items 23-26, wherein the subject has age related macular degeneration, and upon hydrolysis D1 and D2 form an anti-angiogenic steroid, a corticosteroid, or a glucocorticosteroid.

28. The method of any one of items 23-26, wherein the subject has glaucoma, and upon hydrolysis D1 and D2 form an intraocular pressure (TOP) lowering steroid.

29. The method of any one of items 1-28, wherein the article is formed by a process comprising the steps of:
(a) heating the compound, or a pharmaceutically acceptable salt thereof, to form a melt; and
(b) heat molding the melt to form the article.

30. The method of any one of items 1-28, wherein the article is formed by a process comprising the steps of:
(a) heating the compound, or a pharmaceutically acceptable salt thereof, to form a melt; and
(b) injection molding the melt to form the article.

31. The method of any one of items 1-28, wherein the article is formed by a process comprising the steps of:
(a) heating the compound, or a pharmaceutically acceptable salt thereof, to form a melt; and
(b) blow molding the melt to form the article.

32. The method of any one of items 1-28, wherein the article is formed by a process comprising the steps of:
(a) dissolving the compound, or a pharmaceutically acceptable salt thereof, to form a solution; and
(b) evaporating the solvent to form the article.

33. The method of any one of items 1-28, wherein the article is formed by a process comprising the steps of:
(a) dissolving the compound, or a pharmaceutically acceptable salt thereof, to form a solution; and
(b) electrospinning, dry spinning, wet spinning, gel spinning, or electrospraying the solution to form the article.

34. The method of any one of items 1-28, wherein the article is formed by a process comprising the steps of:
(a) heating the compound, or a pharmaceutically acceptable salt thereof, to form a melt; and
(b) electrospinning or electrospraying the melt to form the article.

35. The method of any one of items 1-28, wherein the article is formed by a process comprising the steps of:
(a) heating the compound, or a pharmaceutically acceptable salt thereof, to form a melt; and
(b) extruding the melt to form the article.

36. A method of forming of any one of items 29-35, wherein the article is formed by a process comprising:
(a) heating the compound, or a pharmaceutically acceptable salt thereof, to form a melt;
(b) cooling the melt to form a glassy state composition; and
(c) heating the glassy state composition to a temperature above the glass transition temperature of the glassy state composition and shaping the glassy state composition to form a shaped article.

37. A method of forming of any one of items 29-35, wherein the article is formed by a process comprising:
(a) dissolving the compound, or a pharmaceutically acceptable salt thereof, in a solvent to form a solution;
(b) evaporating the solvent to form a glassy state composition; and
(c) heating the glassy state composition to a temperature above the glass transition temperature of the glassy state composition and shaping the glassy state composition to form a shaped article.

38. The method of item 36 or 37, wherein step (c) comprises extruding, molding, blow molding, heat spinning, electrospinning or electrospraying the glassy state composition to form the shaped article.

39. A method of forming of any one of items 29-35, wherein the article is formed by a process comprising:
(a) dissolving the compound, or a pharmaceutically acceptable salt thereof, in a solvent to form a solution;
(b) electrospraying or electrospinning the solution to form a glassy state composition; and
(c) heating the glassy state composition to a temperature above the glass transition temperature of the glassy state composition and shaping the glassy state composition to form a coating.

40. The method of any one of items 1-39, wherein the article is free of controlled release excipient.

41. The method of any one of items 1-39, wherein the article is free of a crystallization inhibiting excipient.

42. The method of any one of items 1-39, wherein the article is free of a mechanical integrity enhancing excipient.

43. The method of any one of items 1-39, wherein the article is free of a binding excipient.

44. The method of any one of items 1-43, wherein the article optionally has a glassy state.

45. A compound of formula (II-n):

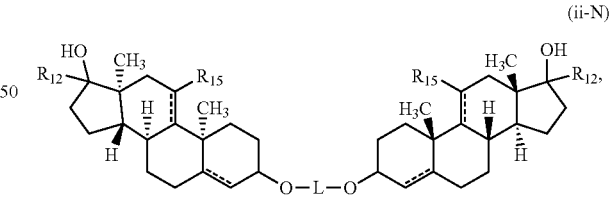

(ii-N)

wherein $R_{12}$ represents —C(=O)CH$_2$OC(=O)CH$_3$, —C(=O)CH$_2$OH, or —C(=O)CH$_3$;

$R_{15}$ represents H or OH;

L is —C(O)O—(R$^A$)—OC(O)— or —C(O)—OC(O)—(R$^A$)—C(O)O—C(O)—, $R^A$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—(R$^A$)—O is a radical of a polyol and includes at least one free hydroxyl group or O—(R$^A$)—O is selected from:

—O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

46. The compound of item 45, wherein the compound is formed from anecortave acetate, anecortave, 11-epicortisol, 17α-hydroxyprogesterone, tetrahydrocortexolone, or tetrahydrocortisol.

47. A compound of formula (II-o):

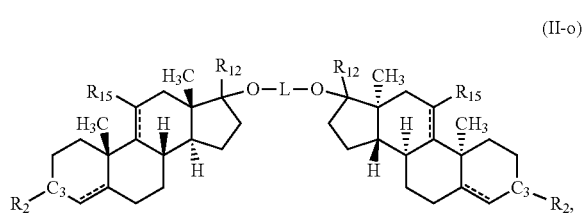

(II-o)

wherein
the bond between C$_3$ and R$_2$ is a single or a double bond;
R$_2$ represents OH or =O;
R$_{12}$ represents —C(=O)CH$_2$OC(=O)CH$_3$, —C(=O)CH$_2$OH, or —C(=O)CH$_3$;
R$_{15}$ represents H or OH;
L is —C(O)O—(R$^A$)—OC(O)— or —C(O)—OC(O)—(R$^A$)—C(O)O—C(O)—, R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from:
—O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

48. The compound of item 47, wherein the compound is formed from anecortave acetate, anecortave, 11-epicortisol, 17α-hydroxyprogesterone, tetrahydrocortexolone, or tetrahydrocortisol.

49. A compound of formula (II-p):

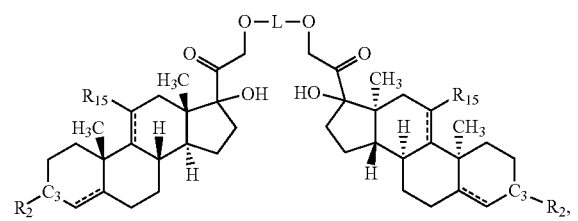

(II-p)

wherein
the bond between C$_3$ and R$_2$ is a single or a double bond;
R$_2$ represents OH or =O; R$_{15}$ represents H or OH;
L is —C(O)O—(R$^A$)—OC(O)— or —C(O)—OC(O)—(R$^A$)—C(O)O—C(O)—;

R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

50. The compound of item 49, wherein the compound is formed from anecortave, 11-epicortisol, tetrahydrocortexolone, or tetrahydrocortisol.

51. A compound of formula (II-r):

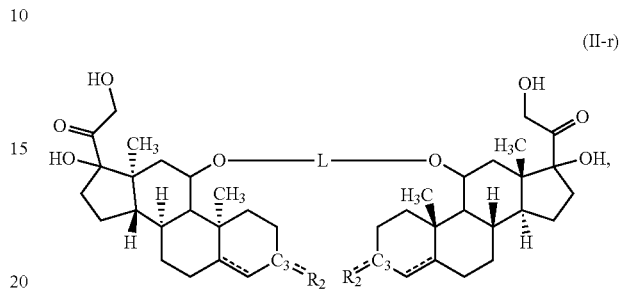

(II-r)

wherein
the bond between C$_3$ and R$_2$ is a single or a double bond;
R$_2$ represents OH or =O; and
L is —C(O)O—(R$^A$)—OC(O)— or —C(O)—OC(O)—(R$^A$)—C(O)O—C(O)—; and R$^A$ is selected from C$_{1-20}$ alkylene, a linear or branched heteroalkylene of 1 to 20 atoms, a linear or branched C$_{2-20}$ alkenylene, a linear or branched C$_{2-20}$ alkynylene, a C$_{5-10}$ arylene, a cyclic system of 3 to 10 atoms, or O—(R$^A$)—O is a radical of a polyol and includes at least one free hydroxyl group or O—(R$^A$)—O is selected from:
—O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

52. The compound of item 50, wherein the compound is formed from 11-epicortisol or tetrahydrocortisol.

53. A method of treating an eye of a subject in need thereof, said method comprising:

(i) providing an article formed from a compound of formula (A-I):

D1-L-D2 or a pharmaceutically acceptable salt thereof, wherein each of D1 and D2 is, independently, a radical formed from a steroid selected from an antibiotic steroid, a glucocorticoid steroid, an IOP lowering steroid, and a corticosteroid; and L is a linker covalently linking D1 to D2, wherein the article is a fiber, a cylinder, a stent, or a tube; and (ii) inserting the article into a Schlemm's canal in the eye of the subject without blocking the fluid passage, wherein the article is free of controlled release polymer, free of a crystallization inhibiting excipient, free of a binding excipient, and/or free of a mechanical integrity enhancing excipient; or wherein the article optionally has a glassy state.

54. A method of reducing intraocular pressure in an eye of a subject in need thereof, said method comprising:

(i) providing an article formed from a compound of formula (A-I):

D1-L-D2 or a pharmaceutically acceptable salt thereof, wherein each of D1 and D2 is, independently, a radical formed from a steroid selected from an antibiotic steroid, a glucocorticoid steroid, an IOP lowering steroid, and a corticosteroid; and L is a linker covalently linking D1 to D2, wherein the article is sized to provide a fluid passageway between the suprachoroidal space and the anterior chamber thereby reducing intraocular pressure in the eye; and (ii) inserting the article into a suprachoroidal space of the eye, wherein the article is positioned to extend from the suprachoroidal space to the anterior chamber of the eye to provide the fluid passageway, wherein the article is free of controlled release polymer, free of a crystallization inhibiting excipient, free of a binding excipient, and/or free of a mechanical integrity enhancing excipient; or wherein the article optionally has a glassy state.

55. The method of item 53 or 54, wherein L is covalently linked to D1 and to D2 via one or more ester, carbonate, carbonate ester, or anhydride linkages.

56. The method of any one of items 53-55, wherein
L comprises the radical —C(O)—($R^4$)—C(O)— or —O—($R^4$)—O—;
$R^4$ is a radical of a polyol and includes at least one free hydroxyl group or $R^4$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, —(CH$_2$CH$_2$O)$_q$CH$_2$CH$_2$—, —(CH$_2$CH$_2$CH$_2$CH$_2$O)$_r$CH$_2$CH$_2$CH$_2$CH$_2$—, or —(CH$_2$CH(CH$_3$)O)$_s$CH$_2$CH(CH$_3$)—; and
q, r, and s are integers from 1 to 10.

57. The method of any one of items 53-56, wherein D1 and D2 are formed from the same steroid and the compound is further described by one of formulas (II-a)-(II-m).

58. The method of any one of items 53-57, wherein D1 and D2 are formed from different steroids and each of D1 and D2 are, independently, further described by one of formulas (I-a)-(I-k).

59. The method of any one of items 53-58, wherein at least 70% (w/w) of the article is a compound of formula (A-I).

60. The method of item 59, wherein at least 90% (w/w) of the article is a compound of formula (A-I).

61. The method of any one of items 53-60, wherein the compound, D1, or D2 are released from the article through surface erosion.

62. The method of item 61, wherein the surface erosion releases less than 10% of D1 or D2, as a percentage of the total drug, D1 or D2, present in the article in prodrug form, at 37° C. in 100% bovine serum over 5 days; or the surface erosion releases less than 2% of D1 or D2, as a percentage of the total drug, D1 or D2, present in the article in prodrug form, at 37° C. in PBS over 5 days; or the surface erosion releases greater than 20% of D1 or D2, as a percentage of the total drug, D1 or D2, present in the article in prodrug form, at 37° C. in 100% bovine serum over not fewer than 6 days; or the surface erosion releases greater than 5.0% of D1 or D2, as a percentage of the total drug, D1 or D2, present in the article in prodrug form, at 37° C. in PBS over not fewer than 6 days; or D1 and/or D2 is released from the article at a rate such that $t_{10}$ is greater than or equal to $\frac{1}{10}$ of $t_{50}$.

63. The method of any one of items 53-62, wherein the article further comprises from 0.1% to 10% (w/w) of one or more additives, wherein the one or more additives are selected from plasticizers, antioxidants, binders, lubricants, dyes, and mixtures thereof.

64. The method of any one of items 53-63, wherein the article is a fiber or cylinder.

65. The method of any one of items 53-63, wherein the article is in the form of a stent, or a tube.

66. The method of any one of items 53 or 55-65, wherein the article is positioned and sized to support the Schlemm's canal and keep the Schlemm's canal open.

67. The method of any one of items 53-66, wherein the ocular condition is an inflammatory condition.

68. The method of item 67, wherein the inflammatory condition is inflammation associated with cataract surgery.

69. The method of item 67, wherein the inflammatory condition is inflammation associated with glaucoma surgery.

70. The method of any one of items 67-69, wherein upon hydrolysis, D1 and D2 form a corticosteroid or a glucocorticoid steroid.

71. The method of item 70, wherein said compound is further described by the formula (III):

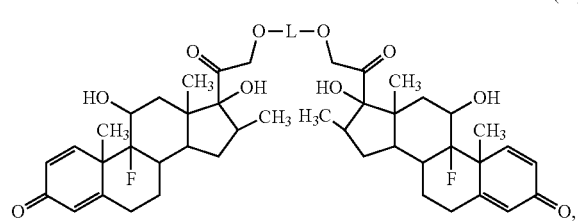

(III)

or a pharmaceutically acceptable salt thereof, wherein
L is —C(O)O—($R^4$)—OC(O)—, —C(O)—OC(O)—($R^4$)—C(O)O—C(O)—; $R^4$ is selected from $C_{1-20}$ alkylene, a linear or branched heteroalkylene of 1 to 20 atoms, a linear or branched $C_{2-20}$ alkenylene, a linear or branched $C_{2-20}$ alkynylene, a $C_{5-10}$ arylene, a cyclic system of 3 to 10 atoms, or O—($R^4$)—O is a radical of a polyol and includes at least one free hydroxyl group or O—($R^4$)—O is selected from: —O(CH$_2$CH$_2$O)$_n$CH$_2$CH$_2$O—, —O(CH$_2$CH$_2$CH$_2$CH$_2$O)$_m$CH$_2$CH$_2$CH$_2$CH$_2$O—, or —O(CH$_2$CH(CH$_3$)O)$_p$CH$_2$CH(CH$_3$)O—; and n, m, and p are integers from 1 to 10.

72. The method of any one of items 53 or 55-66, wherein the ocular condition is a bacterial infection.

73. The method of any one of items 53 or 55-66, wherein the ocular condition is conjunctivitis, keratitis, trachoma, or endophthalmitis.

74. The method of item 73, wherein upon hydrolysis, D1 and D2 form fusidic acid.

75. The method of any one of items 53-74, wherein the article is formed by a process comprising the steps of:
(a) heating the compound, or a pharmaceutically acceptable salt thereof, to form a melt; and
(b) heat molding the melt to form the article.

76. The method of any one of items 53-74, wherein the article is formed by a process comprising the steps of:
(a) heating the compound, or a pharmaceutically acceptable salt thereof, to form a melt; and
(b) injection molding the melt to form the article.

77. The method of any one of items 53-74, wherein the article is formed by a process comprising the steps of:
(a) heating the compound, or a pharmaceutically acceptable salt thereof, to form a melt; and
(b) blow molding the melt to form the article.

78. The method of any one of items 53-74, wherein the article is formed by a process comprising the steps of:
(a) dissolving the compound, or a pharmaceutically acceptable salt thereof, to form a solution; and
(b) evaporating the solvent to form the article.

79. The method of any one of items 53-74, wherein the article is formed by a process comprising the steps of:
(a) dissolving the compound, or a pharmaceutically acceptable salt thereof, to form a solution; and
(b) electrospinning, dry spinning, wet spinning, gel spinning, or electrospraying the solution to form the article.

80. The method of any one of items 53-74, wherein the article is formed by a process comprising the steps of:
(a) heating the compound, or a pharmaceutically acceptable salt thereof, to form a melt; and
(b) electrospinning or electrospraying the melt to form the article.

81. The method of any one of items 53-74, wherein the article is formed by a process comprising the steps of:
(a) heating the compound, or a pharmaceutically acceptable salt thereof, to form a melt;
(b) extruding the melt to form the article.

82. A method of forming of any one of items 75-81, wherein the article is formed by a process comprising:
(a) heating the compound, or a pharmaceutically acceptable salt thereof, to form a melt;
(b) cooling the melt to form a glassy state composition; and
(c) heating the glassy state composition to a temperature above the glass transition temperature of the glassy state composition and shaping the glassy state composition to form a shaped article.

83. A method of forming of any one of items 75-81, wherein the article is formed by a process comprising:
(a) dissolving the compound, or a pharmaceutically acceptable salt thereof, in a solvent to form a solution;
(b) evaporating the solvent to form a glassy state composition; and
(c) heating the glassy state composition to a temperature above the glass transition temperature of the glassy state composition and shaping the glassy state composition to form a shaped article.

84. The method of item 82 or 83, wherein step (c) comprises molding, extruding, blow molding, heat spinning, electrospinning or electrospraying the glassy state composition to form the shaped article.

85. A method of forming of any one of items 75-81, wherein the article is formed by a process comprising:
(a) dissolving the compound, or a pharmaceutically acceptable salt thereof, in a solvent to form a solution;
(b) electrospraying or electrospinning the solution to form a glassy state composition; and
(c) heating the glassy state composition to a temperature above the glass transition temperature of the glassy state composition and shaping the glassy state composition to form a coating.

86. The method of any one of items 53-85, wherein the article comprises less than 5% (w/w) of polymeric material of greater than 5 kDa.

87. The method of any one of items 53-85, wherein the article is free of controlled release polymer.

88. The method of any one of items 53-85, wherein the article is free of a crystallization inhibiting excipient 89. The method of any one of items 53-85, wherein the article is free of a mechanical integrity enhancing excipient.

90. The method of any one of items 53-85, wherein the article is free of a binding excipient.

91. The method of any one of items 53-74, wherein the article is a glassy state composition.

92. The method of any one of items 53-74, wherein drug release from the article exhibits a $t_{10}$ that is equal to or greater than $\frac{1}{10}$ of $t_{50}$ when the drug release from the article is measured at 37° C. in phosphate buffered saline or in bovine serum.

What is claimed is:

1. A method of treating a posterior ocular disorder or condition of an eye of a subject in need thereof, the method comprising intravitreally administering to the eye of the subject in need thereof an intravitreal implant comprising a steroidal compound represented by the structure:

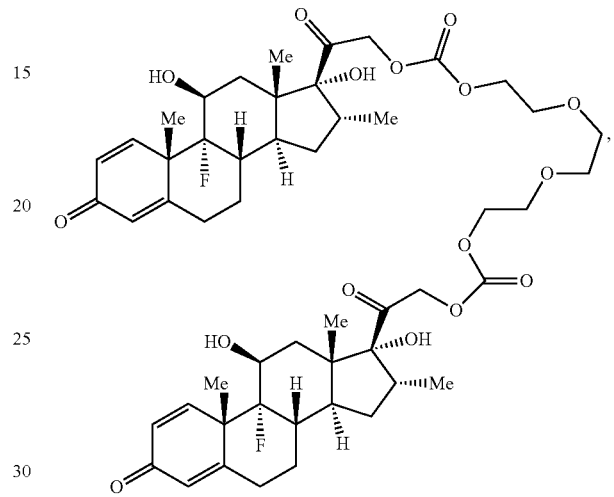

the implant comprising the steroidal compound in an amount of at least 95% (w/w), thereby treating the posterior ocular disorder or condition of the eye of the subject in need thereof, the posterior ocular disorder or condition of the eye being macular edema or uveitis.

2. The method of claim 1, wherein the implant comprises the steroidal compound in an amount of at least 98% (w/w).

3. The method of claim 1, wherein the implant is a fiber, fiber mesh, woven fabric, non-woven fabric, pellet, cylinder, hollow tube, microparticle, nanoparticle, or shaped article.

4. The method of claim 3, wherein the implant is a cylinder.

5. The method of claim 1, wherein the implant releases the steroidal compound or dexamethasone in its free form in an amount sufficient to treat the posterior ocular disorder or condition of the eye of the subject in need thereof.

6. The method of claim 1, wherein the implant releases the steroidal compound or dexamethasone in its free form over a period of at least a day.

7. The method of claim 6, wherein the implant releases the steroidal compound or dexamethasone in its free form over a period of a least a month.

8. The method of claim 7, wherein the implant releases the steroidal compound or dexamethasone in its free form over a period of at least a year.

9. The method of claim 1, wherein the posterior ocular disorder or condition is macular edema.

10. The method of claim 9, wherein the macular edema is diabetic macular edema (DME).

11. The method of claim 9, wherein the macular edema is macular edema from a retinal disorder.

12. The method of claim 11, wherein the retinal disorder is a retinal vein occlusion (RVO).

13. The method of claim 12, wherein the retinal vein occlusion is a central RVO.

14. The method of claim 1, wherein the posterior ocular disorder or condition is uveitis.

15. The method of claim 1, wherein the eye of the subject is substantially free of infection.

* * * * *